US011185605B2

(12) United States Patent
Jin et al.

(10) Patent No.: US 11,185,605 B2
(45) Date of Patent: Nov. 30, 2021

(54) DEVICE AND RELATED COMPOSITIONS AND METHODS FOR USE IN SURFACE DECONTAMINATION

(71) Applicant: Kinnos Inc., Brooklyn, NY (US)

(72) Inventors: Katherine Jin, New York, NY (US); Kevin Tyan, New York, NY (US); Jason Kang, New York, NY (US); David R. Schiff, Highland Park, NJ (US); Jeremy M. Ridley, Phelps, NY (US); Donald A. Muntner, Hoschton, GA (US); Noah Mcneely, Grayson, GA (US); Joseph W. Pruitt, Athens, GA (US); Reile M. Slattery, New York, NY (US)

(73) Assignee: Kinnos Inc., Brooklyn, NY (US)

( * ) Notice: Subject to any disclaimer, the term of this patent is extended or adjusted under 35 U.S.C. 154(b) by 351 days.

(21) Appl. No.: 16/320,401

(22) PCT Filed: Jul. 25, 2017

(86) PCT No.: PCT/US2017/043733
§ 371 (c)(1),
(2) Date: Jan. 24, 2019

(87) PCT Pub. No.: WO2018/022621
PCT Pub. Date: Feb. 1, 2018

(65) Prior Publication Data
US 2019/0343974 A1    Nov. 14, 2019

Related U.S. Application Data

(60) Provisional application No. 62/366,158, filed on Jul. 25, 2016.

(51) Int. Cl.
*A61L 2/24* (2006.01)
*A61L 2/22* (2006.01)
(Continued)

(52) U.S. Cl.
CPC .................. *A61L 2/24* (2013.01);
*A61L 2/28* (2013.01); *C11D 3/48* (2013.01);
*C11D 17/041* (2013.01); *C11D 17/049* (2013.01)

(58) Field of Classification Search
CPC . A61L 2/22; A61L 2/24; C11D 17/049; C11D 17/04; C11D 17/041
See application file for complete search history.

(56) References Cited

U.S. PATENT DOCUMENTS 2,058,489 A    10/1936    Murch et al.
3,609,075 A    9/1971    Barbera
(Continued)

FOREIGN PATENT DOCUMENTS

CA    2320536 A1    3/2001
CA    2665432 A1    5/2008
(Continued)

OTHER PUBLICATIONS

International Search Report dated Nov. 27, 2017 for International Application No. PCT/US2017/043733, filed Jul. 25, 2017.
(Continued)

*Primary Examiner* — Kevin Joyner
(74) *Attorney, Agent, or Firm* — Elmore Patent Law Group, P.C.; Joseph Zucchero; Carolyn Elmore

(57) ABSTRACT

Devices are provided for applying an indicator composition and, optionally, a disinfectant composition to an article being dispensed through the device. The device includes a housing at least partially surrounding an interior volume and having a wall defining a dispensing aperture extending through the wall, a reservoir having at least one chamber sized to contain an indicator composition, and an application mechanism positioned within the housing relative to the dispensing aperture. The reservoir optionally has a second chamber sized to contain a disinfectant composition. The (Continued)

application mechanism is configured to be in fluid communication with the reservoir to apply an amount of the indicator composition and the optional disinfectant composition from the reservoir to an article dispensed through the dispensing aperture. Related compositions, articles, and methods are provided.

38 Claims, 28 Drawing Sheets

(51) Int. Cl.
*A47K 10/32* (2006.01)
*C11D 17/04* (2006.01)
*A61L 2/28* (2006.01)
*C11D 3/48* (2006.01)

(56) References Cited

U.S. PATENT DOCUMENTS

| | | |
|---|---|---|
| 4,071,463 A | 1/1978 | Steinhauer |
| 4,229,410 A | 10/1980 | Kosti |
| 4,249,274 A | 2/1981 | Kitko |
| 4,308,625 A | 1/1982 | Kitko |
| 4,346,120 A | 8/1982 | Morley et al. |
| 4,353,866 A | 10/1982 | Wong |
| 4,390,342 A | 6/1983 | Bruttel |
| 4,420,412 A | 12/1983 | Wong |
| 4,474,677 A | 10/1984 | Foxlee |
| 4,605,534 A | 8/1986 | Meloy |
| 4,623,476 A | 11/1986 | Nayar et al. |
| 4,639,326 A | 1/1987 | Czempik et al. |
| 4,678,658 A | 7/1987 | Casey et al. |
| 4,822,854 A | 4/1989 | Ciolino |
| 4,898,681 A | 2/1990 | Burton |
| 5,034,150 A | 7/1991 | Smith |
| 5,064,635 A | 11/1991 | Casey |
| 5,110,492 A | 5/1992 | Casey |
| 5,257,711 A | 11/1993 | Wirtz-odenthal |
| 5,358,653 A | 10/1994 | Gladfelter et al. |
| 5,547,662 A | 8/1996 | Khan |
| 5,556,835 A | 9/1996 | Inaoka et al. |
| 5,670,469 A | 9/1997 | Dingus |
| 6,213,424 B1 * | 4/2001 | Helfer-Grand ......... A47K 10/34 222/192 |
| 6,362,156 B1 | 3/2002 | Hsu et al. |
| 6,447,757 B1 | 9/2002 | Orlowski et al. |
| 6,503,877 B2 | 1/2003 | Grande et al. |
| 6,525,237 B1 | 2/2003 | Purdon et al. |
| 6,677,287 B1 | 1/2004 | Willman et al. |
| 6,814,816 B2 | 11/2004 | Achar et al. |
| 6,900,167 B2 | 5/2005 | Griese et al. |
| 7,179,779 B1 | 2/2007 | Hauser et al. |
| 7,271,137 B2 | 9/2007 | Tucker |
| 7,276,468 B1 | 10/2007 | Tucker |
| 7,750,199 B1 | 7/2010 | Tucker |
| 8,389,463 B2 | 3/2013 | Mohs et al. |
| 9,101,134 B2 | 8/2015 | Huang |
| 9,155,310 B2 | 10/2015 | Agrawal et al. |
| 9,458,414 B2 | 10/2016 | Rieth et al. |
| 9,717,669 B2 | 8/2017 | Cozean et al. |
| 10,052,398 B2 | 8/2018 | Kang et al. |
| 10,246,671 B2 | 4/2019 | Kang et al. |
| 10,329,520 B2 | 4/2019 | Kang et al. |
| 10,344,251 B2 | 6/2019 | Kang et al. |
| 2001/0051567 A1 | 12/2001 | Schaschke |
| 2003/0059483 A1 | 3/2003 | Sowle |
| 2003/0100101 A1 | 5/2003 | Huth et al. |
| 2003/0168489 A1 | 9/2003 | Formon et al. |
| 2004/0251375 A1 | 12/2004 | Denen et al. |
| 2005/0019090 A1 | 1/2005 | Youichi |
| 2006/0147482 A1 | 7/2006 | Chang |
| 2008/0067470 A1 | 3/2008 | Thangaraj et al. |
| 2008/0193650 A1 | 8/2008 | Lyon |
| 2008/0202953 A1 | 8/2008 | Mueller et al. |
| 2009/0032636 A1 | 2/2009 | Orlandi et al. |
| 2009/0099054 A1 | 4/2009 | Smith |
| 2010/0032443 A1 | 2/2010 | Mueller et al. |
| 2010/0069274 A1 | 3/2010 | Ebine et al. |
| 2010/0134296 A1 | 6/2010 | Hwang |
| 2012/0021068 A1 | 1/2012 | Barness et al. |
| 2013/0058867 A1 | 3/2013 | Moro et al. |
| 2013/0071488 A1 | 3/2013 | Suekuni et al. |
| 2013/0100101 A1 | 4/2013 | Li et al. |
| 2014/0057987 A1 | 2/2014 | Vinson et al. |
| 2014/0100153 A1 | 4/2014 | Martinez-Crowley |
| 2015/0044144 A1 | 2/2015 | Lin |
| 2015/0093425 A1 | 4/2015 | Moore |
| 2015/0366416 A1 | 12/2015 | Hoefte et al. |
| 2017/0336372 A1 | 11/2017 | Kang et al. |
| 2017/0336373 A1 | 11/2017 | Kang et al. |
| 2018/0010080 A1 | 1/2018 | Kang et al. |
| 2019/0001010 A1 | 1/2019 | Kang et al. |

FOREIGN PATENT DOCUMENTS

| | | |
|---|---|---|
| CA | 2865682 A1 | 3/2015 |
| CN | 1817972 A | 8/2006 |
| CN | 1817972 A | 8/2006 |
| CN | 101222871 A | 7/2008 |
| CN | 102065696 A | 5/2011 |
| CN | 102450381 A | 5/2012 |
| CN | 103766402 A | 5/2014 |
| CN | 104054750 A | 9/2014 |
| CN | 105593149 A | 5/2016 |
| DE | 10318009 A1 | 11/2004 |
| EP | 0018344 A1 | 10/1980 |
| EP | 1290121 A2 | 3/2003 |
| EP | 1457529 B1 | 9/2004 |
| EP | 1846111 A2 | 10/2007 |
| EP | 1926808 A1 | 6/2008 |
| EP | 2170149 B1 | 10/2015 |
| FR | 2988731 A1 | 10/2013 |
| GB | 1032151 A | 6/1966 |
| GB | 2326340 A | 12/1998 |
| RU | 2458706 C1 | 8/2012 |
| WO | 8201319 A1 | 4/1982 |
| WO | 0078911 A1 | 12/2000 |
| WO | 0123510 A2 | 4/2001 |
| WO | 03001931 A1 | 1/2003 |
| WO | 2004091356 A2 | 10/2004 |
| WO | 2005055963 A2 | 6/2005 |
| WO | 2005065509 A1 | 7/2005 |
| WO | 2007010562 A1 | 1/2007 |
| WO | 2008060778 A2 | 5/2008 |
| WO | WO-2008/147904 A2 | 12/2008 |
| WO | WO 2008/147904 A2 | 12/2008 |
| WO | 2009007924 A2 | 1/2009 |
| WO | 2013134327 A1 | 9/2013 |
| WO | 2015106044 A1 | 7/2015 |
| WO | WO-2016/093882 A1 | 6/2016 |
| WO | WO 2016/093882 A1 | 6/2016 |
| WO | WO-2017/139670 A1 | 8/2017 |
| WO | 2018022621 A1 | 2/2018 |

OTHER PUBLICATIONS

International Preliminary Report on Patentability dated Feb. 7, 2019 for International Application PCT/US2017/043733 filed Jul. 25, 2017.
International Search Report dated Apr. 13, 2017 for International Application No. PCT/US2017/017509, filed Feb. 10, 2017. 3 pages.
Written Opinion of the International Searching Authority dated Apr. 13, 2017 for International Application PCT/US2017/017509, filed Feb. 10, 2017. 13 pages.
Extended European Search Report dated Aug. 1, 2019 for European Application No. 1750892.6 filed on Feb. 10, 2017. 10 pages.
International Search Report dated Sep. 10, 2015 for International Application No. PCT/US2015/032325, filed May 23, 2015.

(56) References Cited

OTHER PUBLICATIONS

International Preliminary Report on Patentability dated Jun. 22, 2017 for International Application PCT/US2015/032325 filed May 23, 2015.
Transcript of "Kinnos Co-Founder Jason Kang Reveals the Story Behind a Life-Saving Product", by GoDaddy, Apr. 21, 2020.
Transcript of Kevin Tyan's TedMed Talk "What if we could highlight invisible threats for our lifesavers?" Mar. 22, 2017.
Transcript of NPR interview "Innovation In The Battle Against Ebola" aired on Nov. 3, 2014.
Transcript of PBS Newshour interview "Helping student inventors turn big ideas into the next big thing" aired on Aug. 31, 2016.
Transcript of UN Web TV interview "International Day of Women and Girls in Science", Feb. 10, 2017.
Transcript of "Jason Kang: Ebola Design Challenge, Highlight Bleach Project," by Columbia Engineering, Apr. 1, 2015.
Transcript of "Celebrate Invention 2017," by AAAS-Lemelson Invention Ambassador Program,, Aug. 7, 2017.
Transcript of "TRANS Conference 2017 Press Room Interview with Katherine Jin, Coo and Co-Founder of Kinnos," by H. Spectrum, Dec. 13, 2017.
Transcript of "Katherine Jin Explains the Evolution of Highlight," by Lemelson-MIT,, Jul. 13, 2016.
Transcript of "Kinnos: E-Team Program Gives you a Chance to Think About the Business," by VentureWell, Jul. 19, 2016.
Transcript of "Jason Kang, CEO of Kinnos," featured on Cheddar, Mar. 9, 2017.
Transcript of "ScIQ Interviews: Katherine Jin and Keith Comito, Challenges in American Innovation," by ScIQ, Sep. 2, 2017.
Transcript of "Kinnos Colorized Disinfectant," Disrupt SF 2017, by TechCrunch, Sep. 24, 2017.
Brickman, "All Hands on Deck", The New Yorker, Oct. 27, 2014.
Burns, "STEM Student Spotlight: Jason Kang", Scientific American Blog Network, Mar. 15, 2016.
Cooper, , "Blue dye could help keep Ebola doctors safe", Engadget.com article, Oct. 13, 2016.
Farmer, M. A., "Columbia Confronts the Ebola Crisis", article published on Columbia University Fu Foundation School of Engineering and Applied Science website, Oct. 17, 2014.
Kanno-Youngs, Z., "Student Invention Helps Safeguard Health-Care Workers Treating Ebola", Columbia students develop a powder that turns bleach blue to ensure fully sterilized suits, Wall Street Journal, (https://www.wsj.com/articles/student-invention-helps-safeguard-health-care-workers-treating-ebola-1464300345?cb=logged0.13334920427976615#)., May 26, 2016.

\* cited by examiner

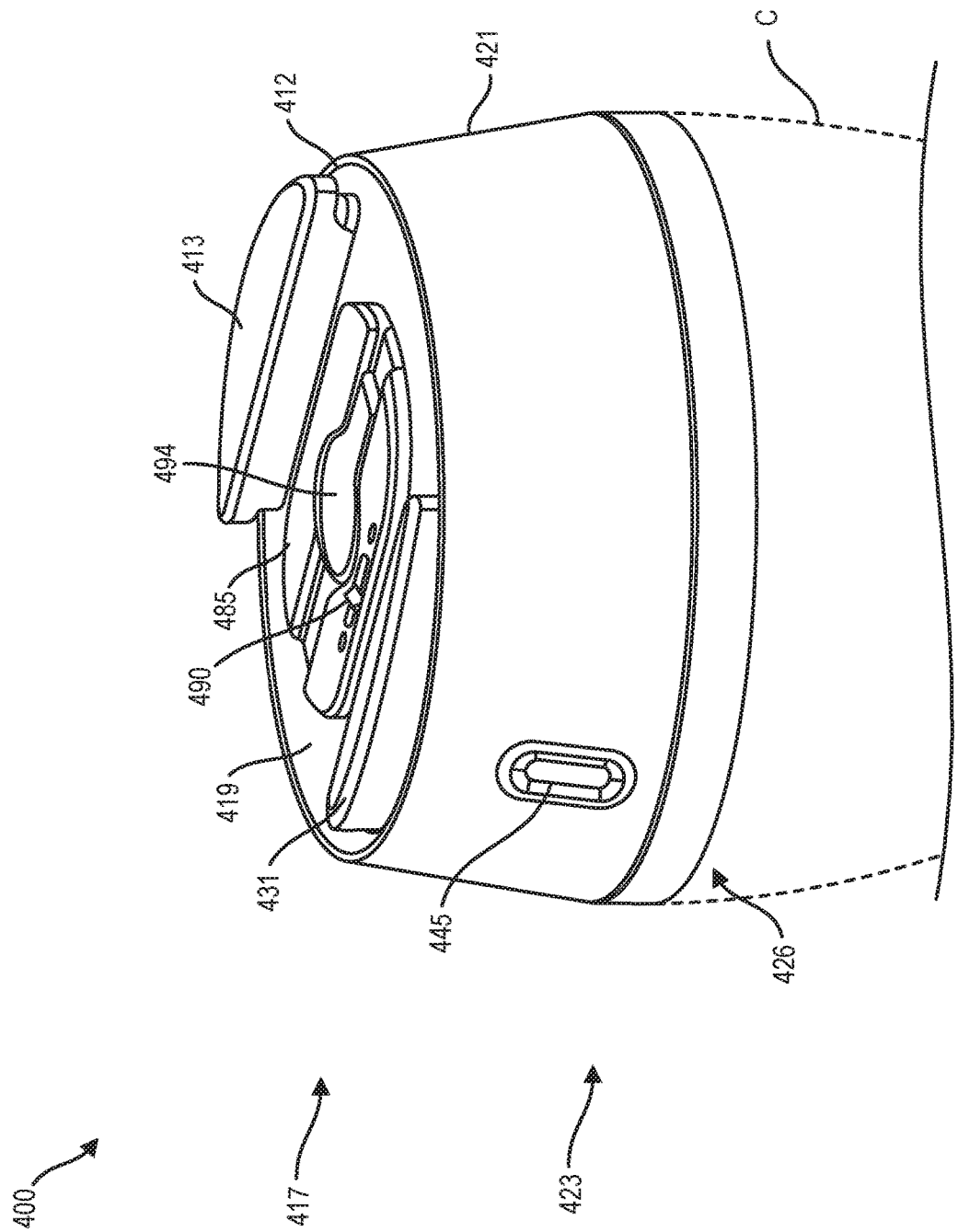

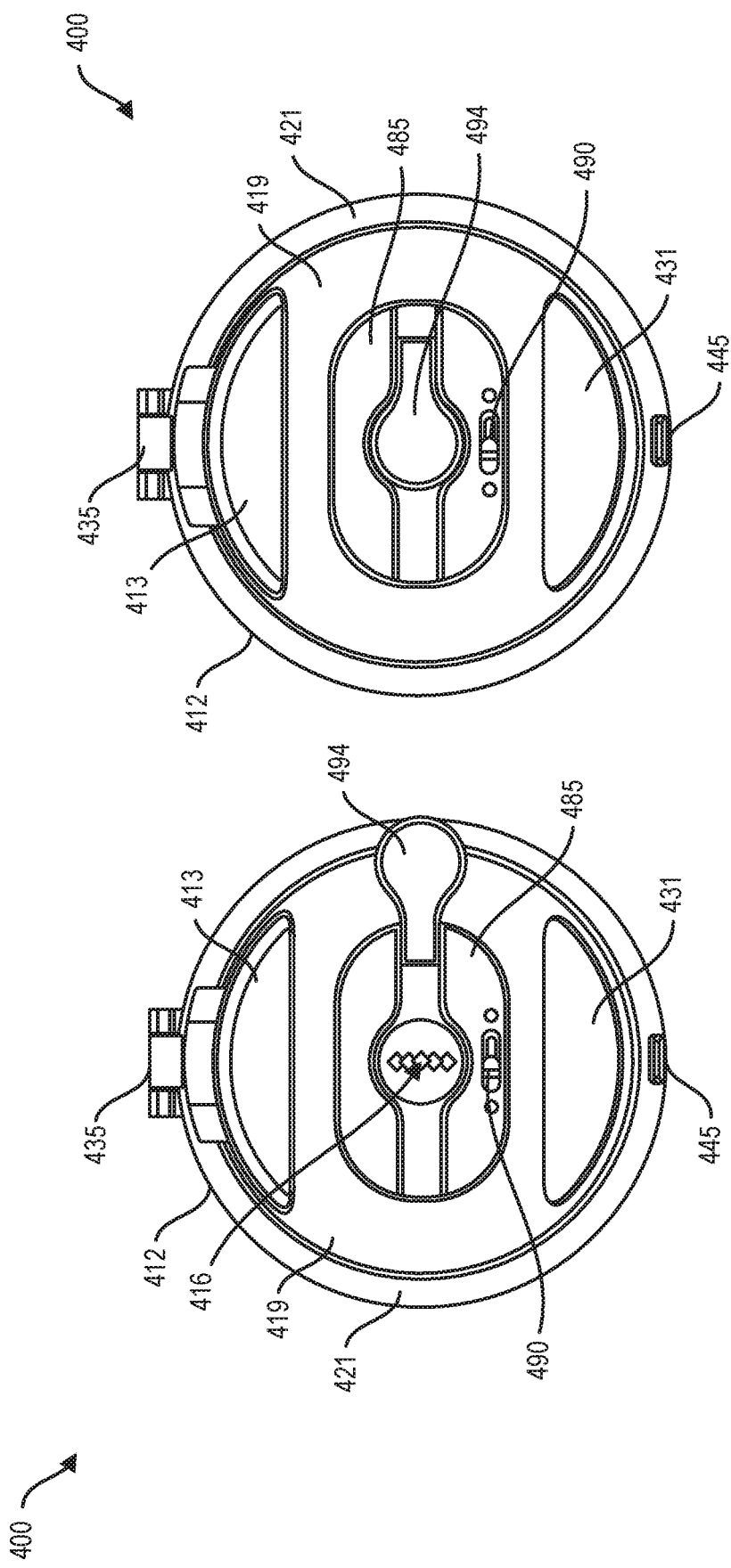

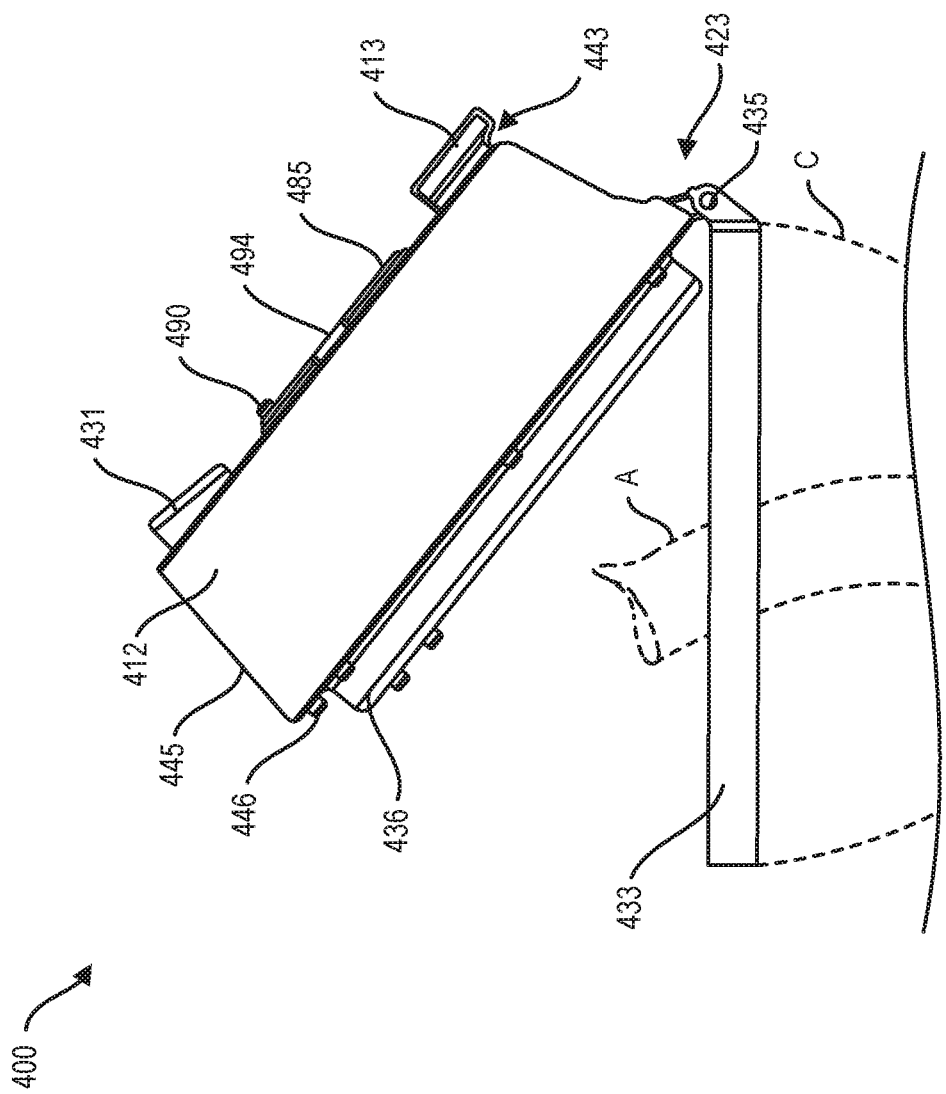

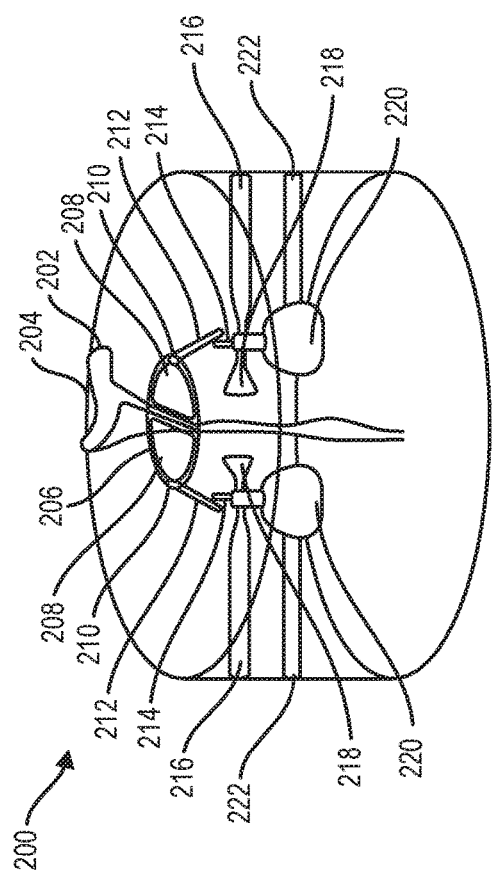
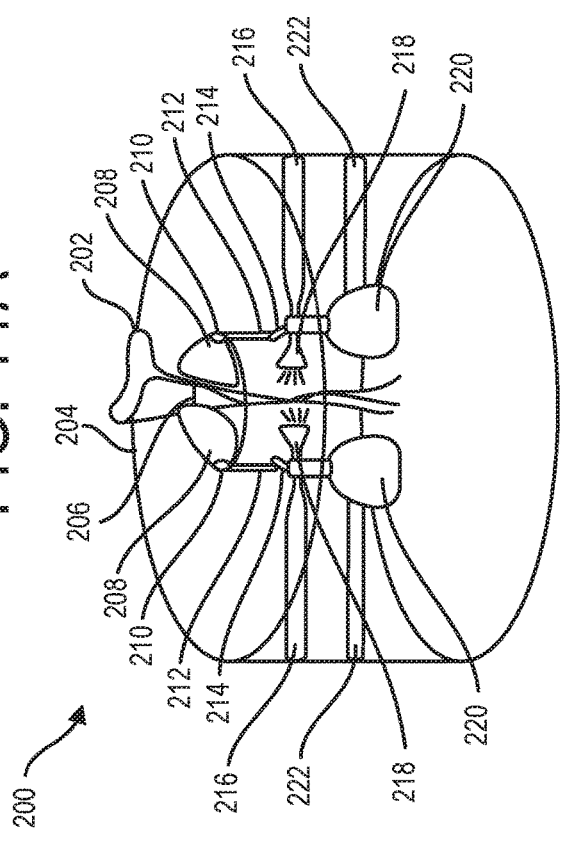

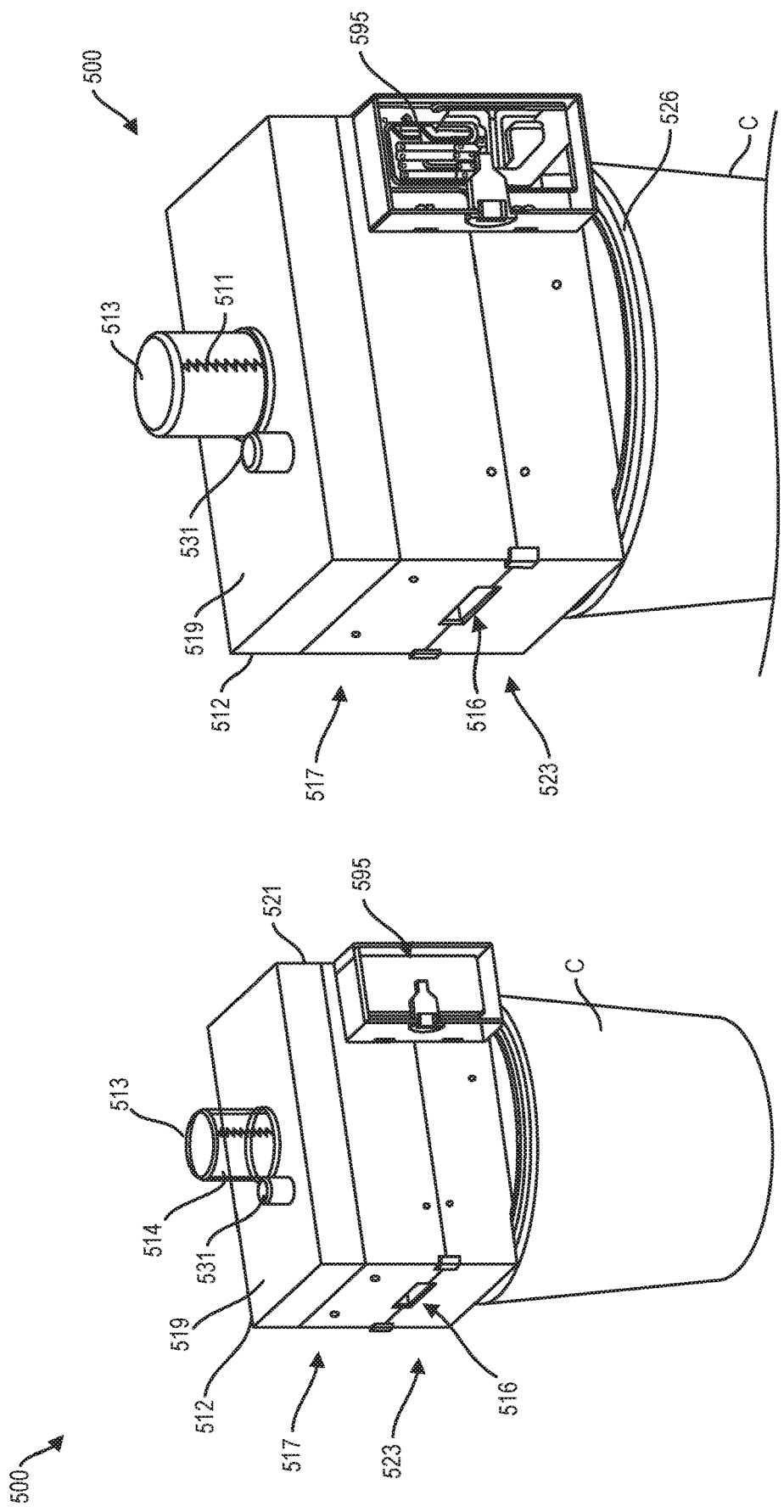

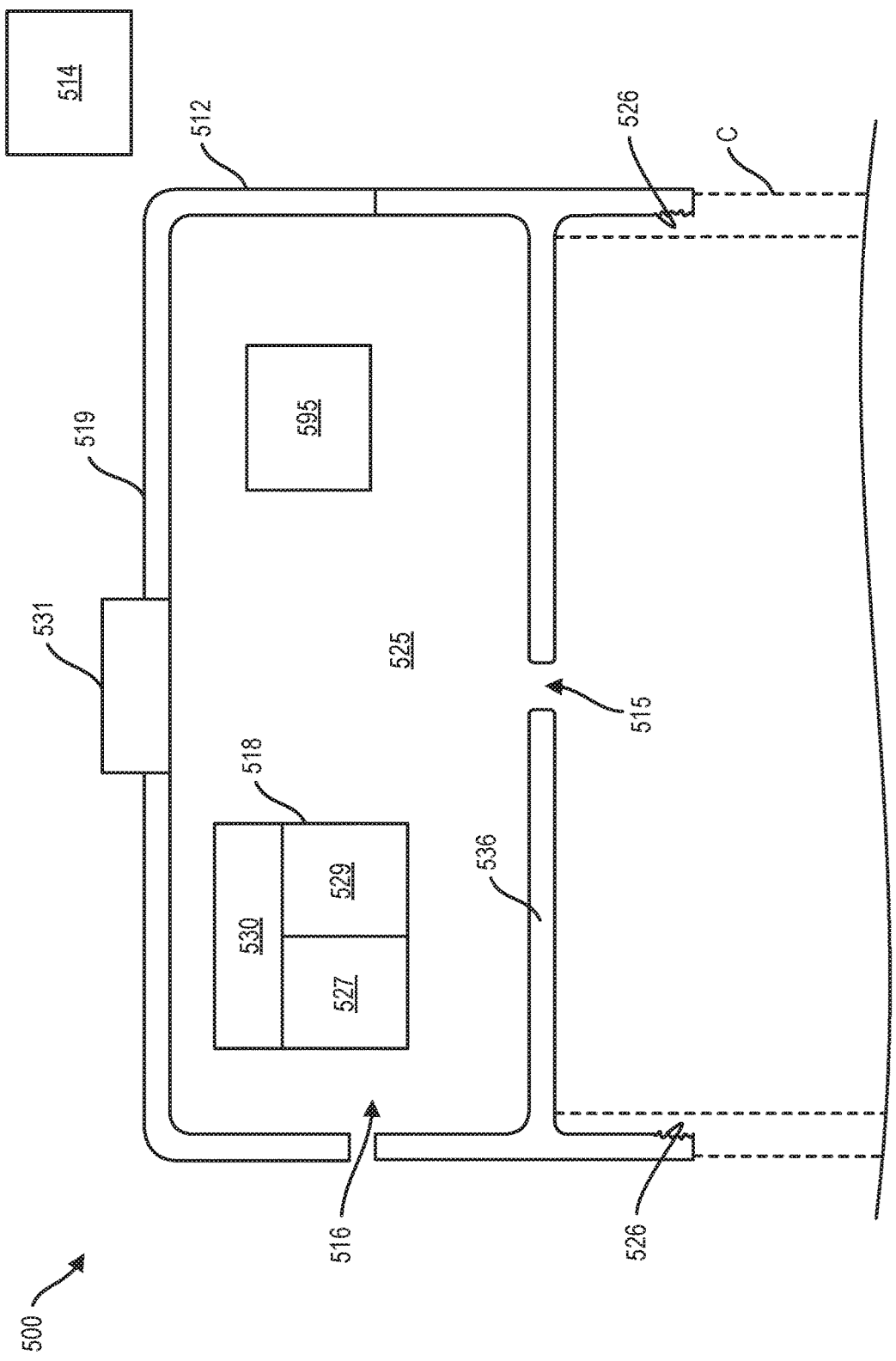

DEVICE AND RELATED COMPOSITIONS AND METHODS FOR USE IN SURFACE DECONTAMINATION

CROSS-REFERENCES TO RELATED APPLICATIONS

This application is a national stage entry, filed under 35 U.S.C. § 371, of International Application No. PCT/US2017/043733, filed on Jul. 25, 2017, which claims the benefit of priority from U.S. Provisional Application Ser. No. 62/366,158, filed on Jul. 25, 2016, the entire contents of which are incorporated herein by reference in their entirety.

TECHNICAL FIELD OF THE INVENTION

The invention generally relates to devices, compositions and methods for visualizing disinfectant agents and monitoring disinfectant efficacy.

BACKGROUND OF THE INVENTION

A recent report published in *JAMA Internal Medicine* found that contamination of skin and clothing occurs during glove and gown removal in 60% of cases (ME Tomas, et al. (2015). Contamination of Health Care Personnel During Removal of Personal Protective Equipment. *JAMA Intern Med.* 175(12):1904-10.) When using educational intervention and visual feedback, the study found that the rate of contamination fell to 18.9%. However, providing training on proper personal protective equipment removal is not always feasible, especially in resource-limited settings or during epidemics, and many commonly used disinfectants do not provide visual feedback. Thus, there exists a need for improved methods and techniques to visually ensure proper disinfection to reduce the rate of contamination.

Commercially available products such as Glo Germ™ have demonstrated the importance of visualizing disinfection. For instance, Glo Germ™ has been used in the Mount Sinai Health System to ensure that surfaces are completely disinfected (*The Wall Street Journal*. (2015, Nov. 2)). However, Glo Germ™ requires the use of an ultraviolet light for visualization, which may not be readily available in the field, and requires a power source. In addition, the need to apply Glo Germ™ before every disinfection and to carry around or install an ultraviolet light source can be tedious and infeasible for checking all disinfected surfaces in a fast-paced hospital setting.

Further studies have also demonstrated that improving compliance with decontamination protocols, include waiting sufficient contact time for a disinfectant to inactivate a pathogen can reduce the rate of hospital-acquired infections by more than 80% (R Orenstein, et al. (2011). *Infect Control Hosp. Epidemiol.* 32(11):1137-9.) This strongly suggests that a method for improving compliance with contact time is urgently needed to reduce the rate of infection in hospitals, as well as for consumer use.

The inclusion of coloring agents in aqueous bleach solutions has previously been described. Due to the strong tendency of bleach solution to oxidize dyes, many have disclosed methods for the incorporation of coloring agents that are stable in bleach. U.S. Pat. No. 4,623,476 to Nayar teaches a method and composition for the stable suspension of pigments in aqueous hypochlorite bleach solutions, using a bleach-stable pigment (Ultramarine Blue), an optical brightener, and a surfactant. U.S. Pat. No. 6,503,877 to Grande teaches a liquid colored thickened bleach composition that includes Ultramarine Blue as a colorant and a viscosifying surfactant that helps provide stable coloration and viscosity upon prolonged periods of storage. U.S. Pat. No. 4,474,677 to Foxlee describes halogenated copper phthalocyanine pigments for forming blue or green aqueous bleaching solutions. These and similar patents solve the problem of rapid bleaching of dyes by strong oxidants by providing more color-stable compositions that retain their color even after prolonged contact with the oxidant.

Oxidizable dyes have been described in the use of cleaning formulations. U.S. Pat. No. 4,308,625 to Kitko discloses the use of bleach-sensitive dyes in combination with hypochlorite sanitizing agents. Kitko describes a toilet bowl sanitizer in which the oxidizable dye and bleach solution are dispensed upon flushing such that the subsequent fading of the color indicates bleaching action. U.S. Pat. No. 6,447,757 to Orlowski discloses the inclusion of FD&C Blue 1 pigment as a component of a bleach-based teeth-whitening mixture. The decolorization of the dye allows the patient to monitor the occurrence and completion of teeth bleaching activity.

U.S. Pat. No. 4,822,854 to Ciolino describes the use of acidifying agents, such as oxalic acid for preventing impurities within the glycol ether-based disinfectant from reacting with and decolorizing the dye at a pH range of 2 to 6.5. The aim is to prevent unwanted impurities within a disinfectant from reacting with the dye.

U.S. Pat. No. 5,110,492 to Casey discloses the combination of a cleaning composition with a disappearing pH dye that must be sealed in an airtight container. Operating under a similar method, U.S. 2014/0057987 by Vinson discloses the composition of a disinfectant with a pH indicator dye and an alkaline substance. The pH dye initially expresses color upon spraying but rapidly fades to colorless upon exposure to the sprayed surface and the air.

Premoistened disinfectant articles have been described previously. U.S. Pat. No. 4,998,984 to McClendon describes a prepackaged single use disposable wiper pad or towelette that is saturated with a disinfecting liquid. U.S. Pat. No. 5,087,450 to Lister describes virucidal wipes that include a gauze pad impregnated with a 10% sodium hypochlorite solution and a hand-held flexible non-porous plastic barrier firmly attached thereto to protect the user from viral contamination and the sodium hypochlorite.

U.S. Pat. No. 8,772,184 to Farrugia relates to a disinfectant wipe made of a fabric coated with a reversible color-changing ink formulation. The wipe is impregnated with a quaternary ammonium sanitizer, and upon depletion of the sanitizer the wipe material undergoes a color change.

U.S. 2006/0222675 by Sabnis describes a disinfectant composition comprising an acid-base indicator and methods for the placement of a thin layer of the disinfectant. The acid-base indicator is described as disappearing or changing color upon use.

U.S. Pat. No. 6,554,156 to Chong describes resealable dispensing caps with an orifice that allows for the dispensing of individual wipes from a roll that primes the next wipe for dispensing while also allowing sealing of the cap to close the container.

U.S. 2015/0305579 by Azelton describes wipe dispensers for dispensing interconnected wipes. An exemplary wipes dispenser is described as including a container body and a removable lid forming an interior region into which a plurality of interconnected wipes may be disposed.

U.S. 2005/0025668 A1 by Katsigras describes a disinfecting article, a sealable housing system for disinfecting articles, and a disinfecting composition comprising a hypohalite composition and a surfactant, for cleaning and disinfecting surfaces, with improved stability and extended efficacy for cleaning and disinfecting surfaces with residues such as foods, dirt, microorganisms, and many other common contaminates.

Spray devices for dispensing liquids are described, for example, in WO 2006/101730 that describes a battery operated spray pump including a piston pump wherein the axis of the pump is arranged at an angle relative to the axis of the spray discharge and the fluid inlet. Valves with actuator assists for use in spray devices are described, for example in WO 2009/085175 and U.S. Pat. No. 8,602,386. Reservoirs for use with cleaning devices are described, for example in U.S. Pat. No. 6,386,392. Related technology is also described, for example a safety valve for an inverted liquid-filled canister, described in U.S. Pat. No. 5,842,504, a non-leaking, non-venting liquid filled canister quick disconnect system, described in U.S. Pat. No. 5,842,682, a consumer safe fitment for connecting a reservoir to a dispensing appliance, described in U.S. Pat. No. 6,321,941, a reclosable fitment for connecting a reservoir to a dispensing appliance, described in U.S. Pat. No. 6,971,589, and integrated vent and fluid transfer fitments described in U.S. Pat. Nos. 6,206,058, 6,491,069, and 6,612,344.

There remains a need for new compositions and methods to ensure the thorough and efficient disinfection of surfaces. The present invention addresses this need by providing articles for conveniently and efficiently applying an indicator solution to a towel or wipe that is dry or pre-moistened with a disinfectant solution.

BRIEF DESCRIPTION OF THE FIGURES

In the drawings,

FIG. 4A is a perspective view of an implementation of a device incorporating a direct contact applicator positioned on a canister of disinfectant articles;

FIG. 4B is a top plan view of the device of FIG. 4A showing the dispensing aperture exposed;

FIG. 4C is a top plan view of the device of FIG. 4A showing the dispensing aperture covered;

FIG. 4F is a side view of the device of FIG. 4A showing the housing in an articulated position;

FIG. 11A is a schematic of an implementation of a device incorporating a non-contact applicator in a first configuration;

FIG. 11B is the device of FIG. 11A where the applicator is in a second configuration;

FIG. 12A is a perspective view of an implementation of a device incorporating a non-contact applicator positioned on a canister of disinfectant articles;

FIG. 12B is a perspective view of the device of FIG. 12A;

FIG. 12H is a schematic view of the device of FIG. 12A.

Figure 1:
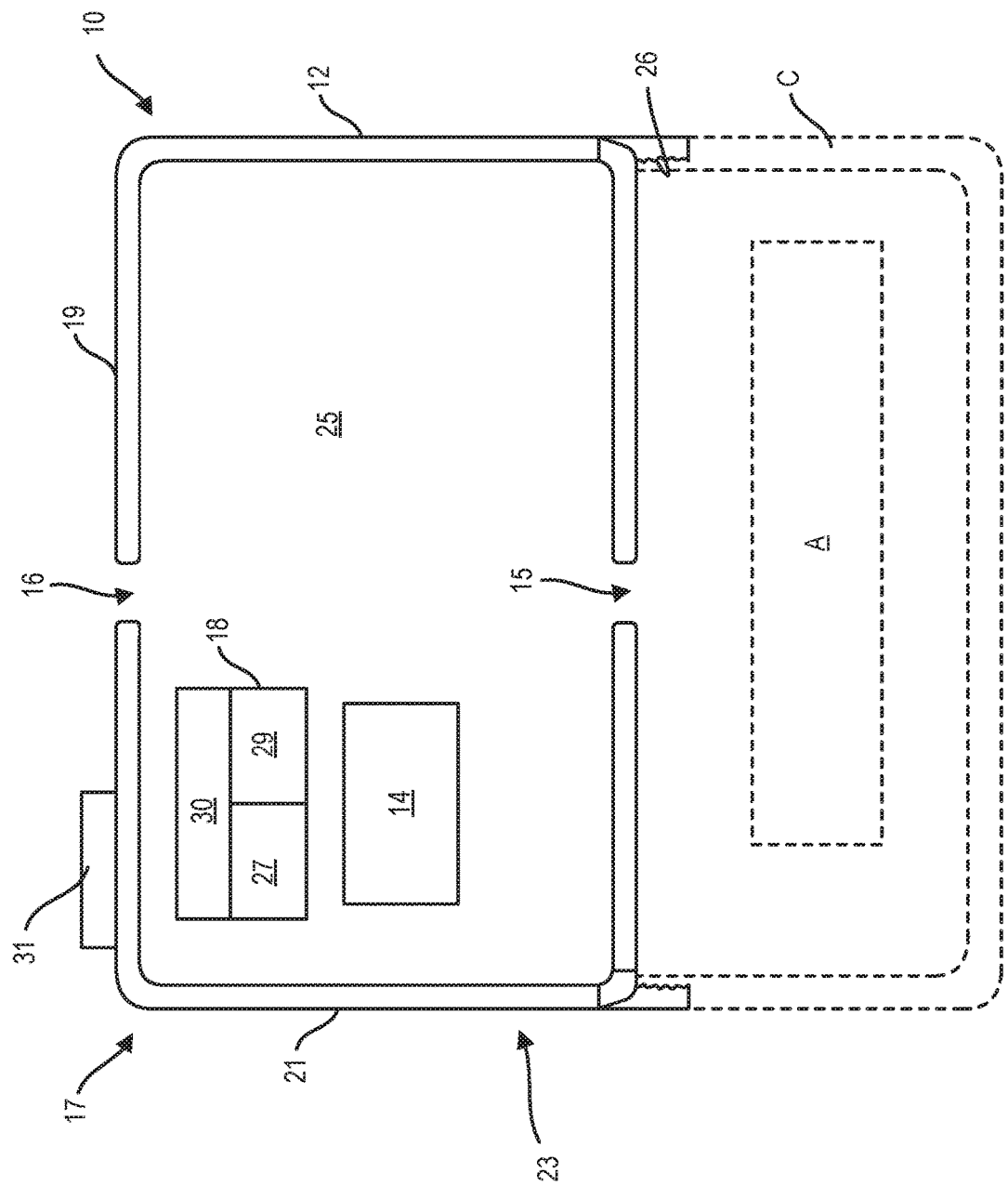
FIG. 1 is a schematic of an implementation of a device configured to apply an indicator solution to a disinfectant article.

Generally speaking, the figures are not to scale in absolute terms or comparatively but are intended to be illustrative. Also, relative placement of features and elements may be modified for the purpose of illustrative clarity.

SUMMARY OF THE INVENTION

The present disclosure relates to devices, compositions and methods for use in the disinfection and decontamination of surfaces. The disclosure provides devices for conveniently and efficiently applying an indicator composition to a solid absorbent substrate such as a cloth, towel, or wipe, which may be referred to herein as a "disinfectant article". In embodiments, the disinfectant article is pre-moistened with a disinfectant composition. In embodiments, a disinfectant composition is applied to the disinfectant article along with the indicator composition by the device described here. The disclosure also provides exemplary formulations of indicator compositions, which are adapted to impart a transient color to the disinfectant article such that the disinfectant can be clearly visualized when applied to a surface, e.g., via application of the towel or wipe to the surface, thereby providing a visual indication of surface coverage. The indicator composition is further adapted to fade to colorless within a predetermined period of time after its application to a surface, thereby providing a visual indication of contact time of the disinfectant with the surface which is advantageous in ensuring adequate decontamination of the surface. Typical disinfectant compositions compatible with the indicator compositions described here include aqueous solutions of common disinfecting agents, for example, sodium hypochlorite, calcium hypochlorite, sodium dichloroisocyanurate, hydrogen peroxide, chlorine dioxide, peracetic acid, quaternary ammonium chloride, and alcohols, such as ethanol and isopropyl alcohol. The devices, compositions and methods described here are suitable for use in both hospital and field settings, as well as for consumer use.

In an aspect, described is a device for applying an indicator composition and, optionally, a disinfectant composition to an article being dispensed through the device. The device includes a housing at least partially surrounding an interior volume and having a wall defining a dispensing aperture extending through the wall. The device includes a reservoir having at least one chamber sized to contain an indicator composition. The reservoir optionally has a second chamber sized to contain a disinfectant composition. The device includes an application mechanism positioned within the housing relative to the dispensing aperture. The application mechanism is configured to be in fluid communication with the reservoir to apply an amount of the indicator composition and an amount of the optional disinfectant composition from the reservoir to an article dispensed through the dispensing aperture. In embodiments, the amount of the indicator composition applied to the disinfectant article is in the range of from 0.0001-0.1 ml per square centimeter ($cm^2$) of the disinfectant article, preferably from 0.0015-0.023 $ml/cm^2$ of disinfectant article. In embodiments, the amount of the optional disinfectant composition applied to the disinfectant article is in the range of from 0.01-0.1 $ml/cm^2$ of the disinfectant article, preferably from 0.02-0.035 $ml/cm^2$ of disinfectant article.

A lower end region of the housing can be sized couple to a canister holding the article. The lower end region can be an opening through which the article is drawn from the canister into the interior volume of the housing. The device can include one or more connecting features on the lower end region of the housing. The one or more connecting features can be configured to removably couple the device to the canister containing the article. When the device is removably coupled to the canister, an interior of the canister can be in fluid communication with the interior volume of the housing through the opening. The device can form a removable lid for the canister. The wall of the housing through which the dispensing aperture extends can form an upper surface of the device or a side surface of the device. The dispensing aperture can have a shape that is rectangular, cross, x, flower petal, or zig-zag. The application mechanism can include a transfer element and at least one applicator. The transfer element can transfer the amount of the indicator composition from the reservoir towards the at least one applicator. The transfer element can create a pressure differential relative to an interior of the reservoir to transfer the amount. The transfer element can create the pressure differential by applying a negative pressure or by applying a positive pressure. The transfer element can include a pumping mechanism that is manually actuated or electrically powered.

The device can further include at least one actuator. The actuator can simultaneously activate the transfer element and the at least one applicator. The device can further include an automatic dispensing mechanism having a motor and a plurality of gear rollers. The plurality of gear rollers can be configured to capture and direct the article through the interior volume of the housing towards the dispensing aperture. The actuator can activate the motor. The device can further include a removable cover positioned over the dispensing aperture. The actuator can open the cover exposing the dispensing aperture. The device can further include one or more grippers configured to engage the article during dispensing allowing for easy removal of the article from the device. The actuator can activate the one or more grippers. The actuator can activate one or more of the transfer element, the at least one applicator, the motor, the cover, and the grippers simultaneously. The device can include one or more actuators that activate the one or more of the transfer element, the at least one applicator, the motor, the cover, and/or the grippers.

The transfer element can include a pumping element that is manually actuated upon actuation of the actuator to create a pressure differential relative to an interior of the reservoir. The transfer element can include a pumping element that is powered by an electric motor upon actuation of the actuator to create a pressure differential relative to an interior of the reservoir. The electric motor can be powered by a battery coupled to the reservoir or the cartridge containing the reservoir. The pumping element can be a positive displacement pump, reciprocating pump, rotary pump, piston pump, diaphragm pump, peristaltic pump, dynamic pump, centrifugal pump, or hydraulic pump. The at least one applicator can be configured to apply the amount of indicator composition to the article by directly contacting the article. The at least one applicator can include a roller, brush, or ball-bearing device. The at least one applicator can include a roller surrounding an inner shaft through which a conduit extends leading to one or more outlets. The roller can include a material having wicking and transfer properties. The roller can include one or more of melamine-, polyester-, polyurethane-, polyimide-, polyethylene-, vinyl-, and polyolefin-based materials. The roller can include ethylene propylene diene monomer (EPDM) foam rubber. The roller can have a hydrophilic coating. The roller can have an inner core of absorbent material surrounded by a material having a higher coefficient of friction than a coefficient of friction of the article.

The at least one applicator can be configured to apply the amount of indicator composition to the article without directly contacting the article. The at least one applicator can include a sprayer. The sprayer can include an outlet and a spray diverter positioned across from the outlet. The spray diverter can include a surface shaped to re-direct the amount of indicator composition exiting the outlet onto a surface of the article being dispensed through the dispensing aperture. The surface of the spray diverter can re-direct the indicator composition at an angle that is between 30 degrees to 150 degrees, preferably 45 degrees to 90 degrees, relative to an axis of a spray discharge from the outlet. The re-directed indicator composition can drip down along a curve of the surface onto an upper surface of the article.

The application mechanism can provide for one-sided or two-sided application of the amount of the indicator composition to the article. The reservoir can be refillable. The reservoir can be contained within a cartridge that is removably coupled to the housing. The reservoir can be pre-filled (and/or refillable) with the indicator composition, or the optional disinfectant composition.

The indicator composition can be a solution including (i) a water-soluble pigment and one or more of a surfactant, an alkaline builder, and a rheology modifier; (ii) a water-soluble pigment and either an oxidizing agent or a reducing agent, and an optional catalyst; or (iii) a pH-dependent pigment and an alkaline builder. The indicator composition can include a water-soluble pigment, preferably FD&C Blue 1 or Acid Green 50, preferably in an amount of from 0.1-5 wt %, and optionally 0.05-5% w/w SXS, preferably about 0.75% w/w SXS. The SXS can be present either alone or in combination with either 0.1-3% w/w SDS, preferably about 0.3% w/w SDS, or in combination with 0.05-5% w/w lambda carrageenan, preferably about 0.4% w/w lambda carrageenan. The fade time of the indicator composition following its application to a surface via a disinfectant article can be from about 2-5 minutes. The indicator composition can include a pigment selected from thymolphthalein, methylene blue, and 3,3-bis-(4-hydroxy-3-ethylphenyl)-1-(3H)-isobenzonfuranone in a solution of ethanol or isopropyl alcohol. The indicator composition can include a pigment and a catalyst selected from hexadecyltrimethylammonium bromide (HTAB), ferrous sulfate, copper (II) sulfate, or copper (II) sulfide caved superstructures, in combination with peracetic acid or hydrogen peroxide. The pigment can be methylene blue, malachite green, indigo carmine, Acid Green 25, Acid Green 50, FD&C Blue 1, pinacyanol chloride, rhodamine B, alpha naphthol orange, azo violet, or thymolphthalein.

In an interrelated aspect, described is an article of manufacture containing an indicator composition in the form of an aqueous solution. The article of manufacture can include a cartridge within which the reservoir is contained and that is removably coupled to the housing of the device. The reservoir can be a single chamber holding the indicator composition or divided into two separated chambers, the two separate chambers either each holding a different composition which when mixed together form the indicator composition or each holding a different composition selected from the indicator composition and a disinfectant composition.

The indicator composition can be an aqueous solution including FD&C Blue 1 or Acid Green 50 in an amount of from 0.1-5 wt %, and optionally 0.05-5% w/w SXS, preferably about 0.75 w/w SXS. The SXS can be present either alone or in combination with either 0.1-3% w/w SDS, preferably about 0.3% w/w SDS, or in combination with 0.05-5% w/w lambda carrageenan, preferably about 0.4% w/w lambda carrageenan. The fade time of the indicator solution following its application to a surface via a disinfectant article can be from about 2-5 minutes. The indicator composition can include from about 0.1-10% w/w, preferably about 0.5% w/w, thymolphthalein in a solution of either 70% ethanol or 63% isopropyl alcohol and provide a fade time of from about 5-30 seconds or from 15-60 seconds, respectively. The indicator composition can include from about 0.1-20% w/w, or preferably about 0.5% w/w 3,3-bis-(4-hydroxy-3-ethylphenyl)-1-(3H)-isobenzonfuranone in a solution of either 70% ethanol or 63% isopropyl alcohol and the composition provides a fade time of from about 0.5-5 minutes. The indicator composition can include from about 0.25-1% w/w, or preferably about 0.5% w/w methylene blue and from about 10-33%, or preferably about 27% sodium sulfite, with the remainder being deionized water, and the composition provides a fade time of from about 15-120 seconds.

In an aspect, the reservoir is divided into two separated chambers and a first of the two separate chambers of the reservoir can hold solution A and a second of the two separate chambers can hold solution B which when mixed together form the indicator composition. Solution A can include a pigment and an optional catalyst and solution B can include a decolorizing agent selected from an oxidizing agent and a reducing agent. Solution A can include 0.1-3 w/w methylene blue in deionized water and solution B can include one or more of ascorbic acid, sodium sulfite, sodium carbonate, sodium perchlorate, and sodium hydroxide. Solution A can include 0.5-2.5 w/w malachite green and solution B can include 0.5-2.5 w/w of an alkaline builder. Solution A can include 0.1-5 w/w of a pigment selected from indigo carmine, Acid Green 50, methylene blue, Acid Green 25, FD&C Blue 1, and pinacyanol chloride, an optional catalyst, such as ferrous sulfate, HTAB, copper (II) sulfate, or copper (II) sulfide caved superstructures, and an optional surfactant, such as sodium dodecyl sulfate; and solution B can include a 35% aqueous solution of hydrogen peroxide or peracetic acid. Solution A can include 0.1-5% w/w rhodamine B, alpha naphthol orange, or azo violet in deionized water and solution B can include bismuth silver oxide or sodium sulfite.

DETAILED DESCRIPTION OF THE INVENTION

The present disclosure provides devices, indicator compositions, and methods for using same to visualize the decontamination and/or disinfection of a surface. The indicator compositions described here are generally in the form of a solution or gel comprising at least one water soluble oxidizable pigment and one or more optional ingredients, as described in more detail infra. The disclosure also provides an article of manufacture comprising an indicator composition as described herein, which is suitable for use with the devices described here. The article of manufacture is adapted for use with the devices described here, is removable therefrom, and comprises a reservoir, as described infra. In embodiments, the disclosure provides a removable device adapted to replace an existing lid or cover of a container holding multiple disinfectant articles. The disinfectant articles may be in the form of woven or non-woven fabrics or sponges which are optionally saturated with a disinfecting composition. In embodiments, the multiple disinfectant articles within a container are formed into a continuous sheet having partial tears or perforations for ease of separation into smaller sheets, e.g., in the form of perforated cloths, towels, or wipes.

Described herein are devices configured to apply an indicator composition as described herein onto an article that is optionally pre-saturated with a disinfectant composition, including for example articles such as disposable wipes or towelettes.

In certain embodiments, provided is a lid that is used to replace the existing lids on disinfectant article canisters, e.g., Clorox Healthcare Bleach Germicidal Wipes and PDI Sani-Cloth Bleach Wipes. An embodiment of the lid includes an adjustable lid that can be formatted to fit atop containers of variable sizes. In certain embodiments, provided is a lid that is configured to or that contains mechanisms that imbue color onto disinfectant articles (i.e. towelette or disposable wipes) as they are dispensed out of the canister. Preferably, the colorant is applied uniformly onto the disinfectant articles as they are dispensed. Any suitable methods or components allowing application of the colorant to the disinfectant articles may be used.

The devices described herein can apply the indicator composition as the disinfectant article is dispensed from its canister. For example, pre-saturated disinfectant wipes can be housed within a canister that allows the wipes to be dispensed from the canister, such as through a region of the lid by a pull-through mechanism. The devices described herein can be coupled to the canister such that the device applies the indicator composition to the wipe as the pre-saturated disinfectant wipe is dispensed from its canister. Alternatively in embodiments where the wipe is not pre-saturated with disinfectant, or where it is desirable to apply additional disinfectant or a different disinfectant to the wipe along with the indicator composition, the device is configured to apply both disinfectant and the indicator composition to the disinfectant article.

FIG. 1 is a schematic of an implementation of a device configured to apply an indicator composition either alone or in combination with a disinfectant composition, to a disinfectant article as the article is dispensed from its canister. The device 10 can include a housing 12 having a dispensing aperture 16, a reservoir 14, and an application mechanism 18 configured to be in fluid communication with the reservoir 14. Each of the components will be described in more detail below. The housing 12 can at least partially surround an interior volume 25 and have a wall defining the dispensing aperture 16 extending through a wall of the housing 12. The location of the dispensing aperture 16 can vary. For example, the dispensing aperture 16 can extend through an upper surface 19 or a side surface 21 of the housing 12 near an upper end region 17 of the housing 12.

Figure 2C:
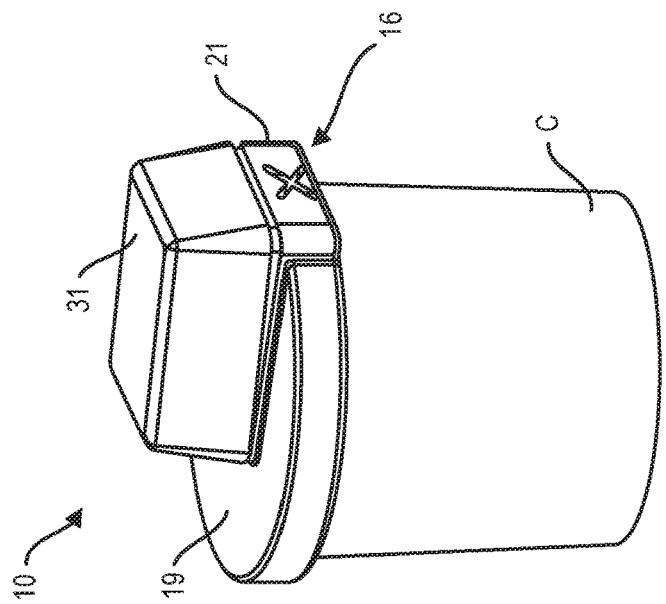
FIG. 2C is a perspective view of an implementation of a device configured to apply an indicator solution to a disinfectant article.
Figure 2B:
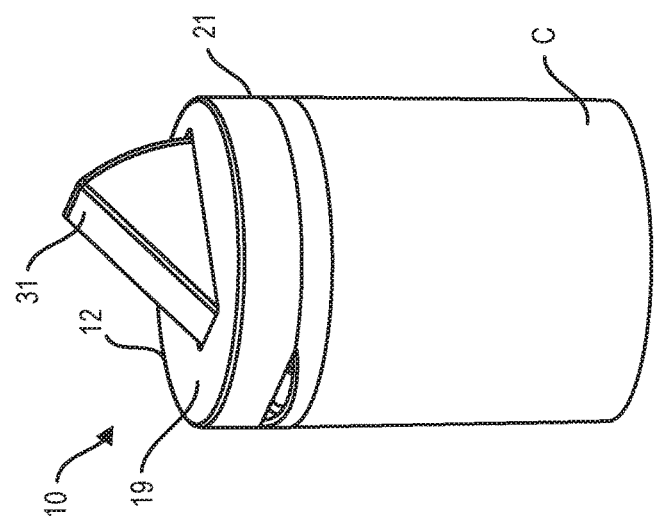
FIG. 2B is a perspective view of an implementation of a device configured to apply an indicator solution to a disinfectant article.

A lower end region 23 of the housing 12 can define an internal aperture or opening 15 such that when the housing 12 is coupled to a region of the canister C of disinfectant articles A, such as an upper end of the canister C, the article A can be drawn into the interior 25 of the housing 12 through the opening 15. When the device 10 is coupled to the canister C of disinfectant articles A, an interior of the canister C can communicate with or be placed in communication with the interior 25 of the housing 12 through the opening 15. The disinfectant article A stored within the interior of the canister C can enter the interior 25 of the housing 12 from the lower end region 23 through the opening 15 and fed towards the dispensing aperture 16 in the upper end region 17. The dispensing aperture 16 need not be in the upper end region 17 and can also be found near a lower end region 23 of the housing (see FIG. 2C).

The lower end region 23 of the housing 12 can incorporate one or more connecting features 26 configured to removably or detachably couple the device 10 to the canister C of disinfectant articles A. The connecting feature 26 can include a thread corresponding to a thread of the canister C, a snap-fit connection, fitting, fastener, or coupling feature sized to fit a region of the canister C. In some implementations, the device 10 is configured to connect to the canister C such that the device 10 functions as a lid on an open end of the canister C. The device 10 can be used to replace an existing lid on the canister C. As such, the connecting feature 26 can be designed according to dimensional standards for container closures. The connecting feature 26 also can be adjustable such that it can fit variable sizes of canisters. In other implementations, the device 10 is configured to connect to the canister C already enclosed with a lid having a dispensing aperture. In this implementation, the device 10 can function as an auxiliary attachment to the already enclosed canister C. The device 10 need not be removable from the canister C and can be a single-use device affixed to a canister C of disinfectant articles A.

Figure 2A:
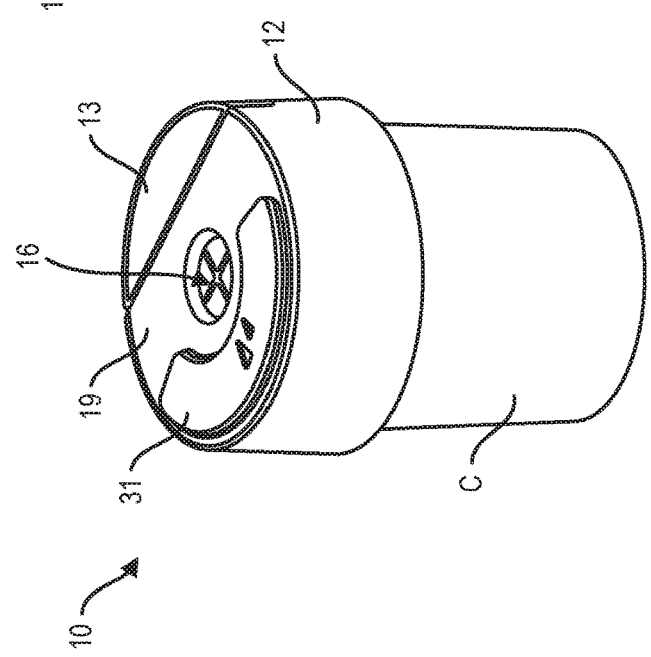
FIG. 2A is a perspective view of an implementation of a device configured to apply an indicator solution to a disinfectant article.

Still with respect to FIG. 1, the reservoir 14 can have at least one reservoir chamber sized to contain an amount of the indicator composition. The device can include more than one reservoir 14 or a single reservoir 14 divided into two or more separate chambers sized to hold volumes of different compositions. In embodiments where the device includes at least two reservoirs 14 or a single reservoir 14 divided into at least two separate chambers, the different compositions may include, for example, two solutions which, when applied to the disinfectant article by actuation of the device, form the indicator composition in situ, on the disinfectant article. Examples of such two-part indicator compositions are described in more detail below. In other embodiments, the different compositions which are held either in two or more reservoirs 14 or in a single reservoir 14 divided into at least two separate chambers may include an indicator composition and a disinfectant composition which are both applied simultaneously to the disinfectant article by actuation of the device. The disinfectant composition is preferably a solution comprising a suitable amount of a disinfectant material, for example including, but not limited to, an aqueous or non-aqueous solution of sodium hypochlorite, calcium hypochlorite, sodium dichloroisocyanurate, hydrogen peroxide, chlorine dioxide, peracetic acid, quaternary ammonium chloride, and alcohols, such as ethanol and isopropyl alcohol. In embodiments, the amount of disinfectant composition applied to the disinfectant article is in the range of from 0.01-0.1 ml per square centimeter ($cm^2$) of the disinfectant article, preferably from 0.02-0.035 ml/$cm^2$ of disinfectant article. Accordingly, where the reservoir is referred to herein as a single reservoir it should be appreciated that the reservoir can be configured to hold more than a single composition. Where the indicator is referred to herein as a composition, solution, fluid or liquid, it should be appreciated that different indicator formulations are considered herein. The indicator composition can be formulated as a liquid solution, a gel, a powder, or other formulation. Preferably, the indicator composition is formulated as a liquid or gel. The reservoir 14 can be located at least partially within the housing 12. The reservoir 14 can be refillable and/or removable from the housing 12. In some implementations, the reservoir 14 can be contained within a cartridge 13 having a housing configured to removably couple to a region of the housing 12 (see FIG. 2A), which will be described in more detail below.

Figure 12C:
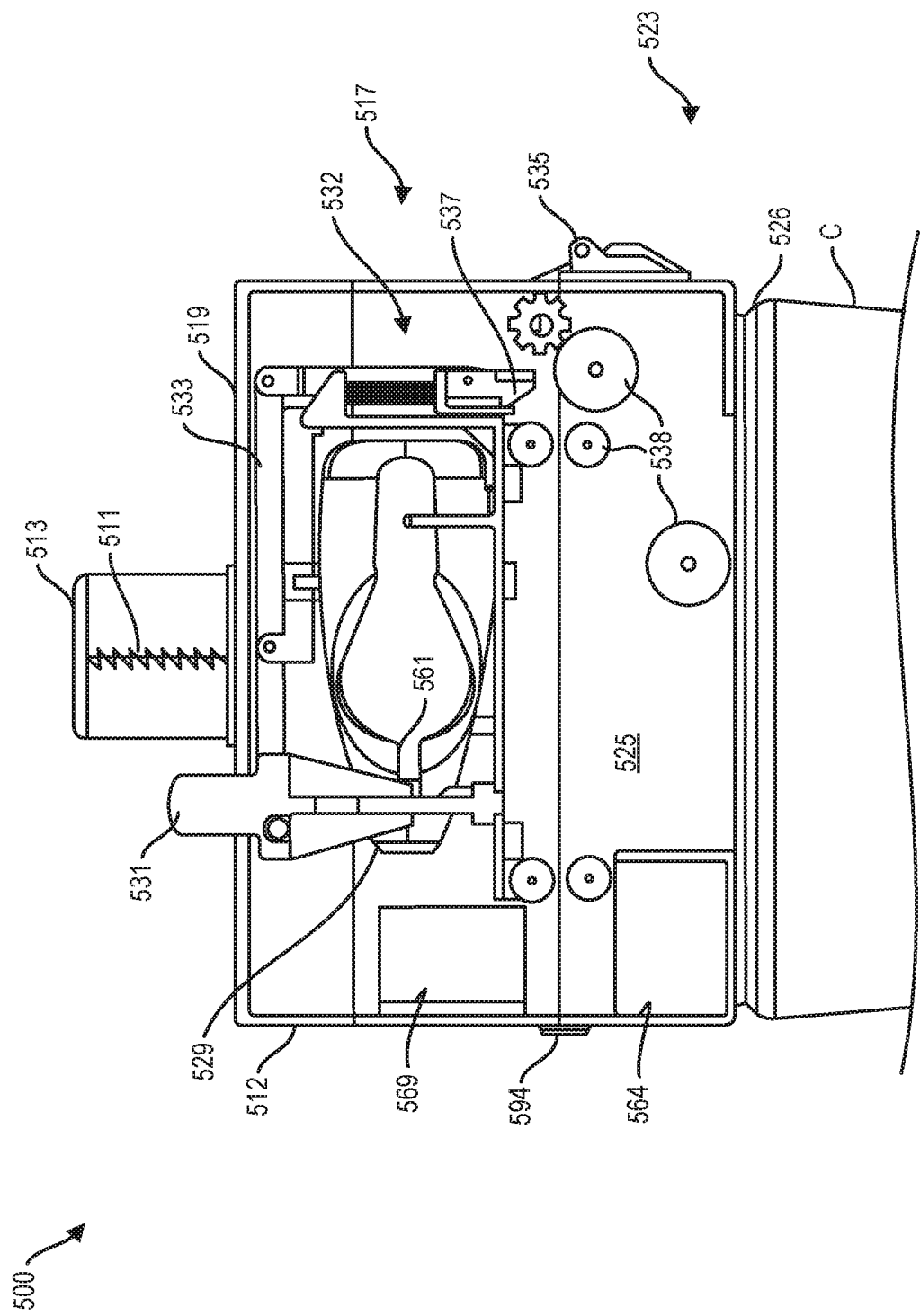
FIG. 12C is a side, cut-away view of the device of FIG. 12A.
Figure 12D:
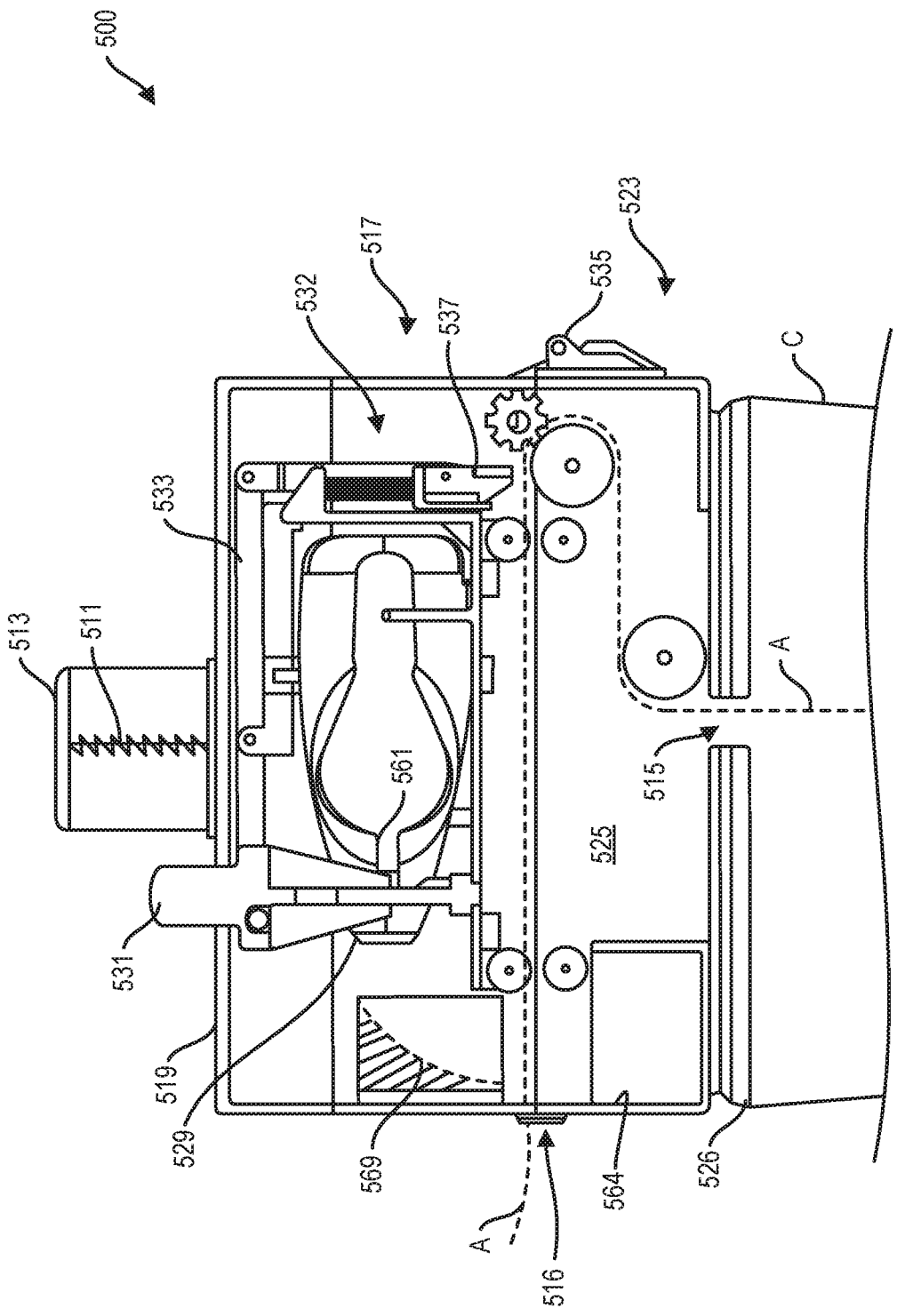
FIG. 12D is a side, cut-away view of the device of FIG. 12A showing the path of a disinfectant article through the interior.
Figure 12E:
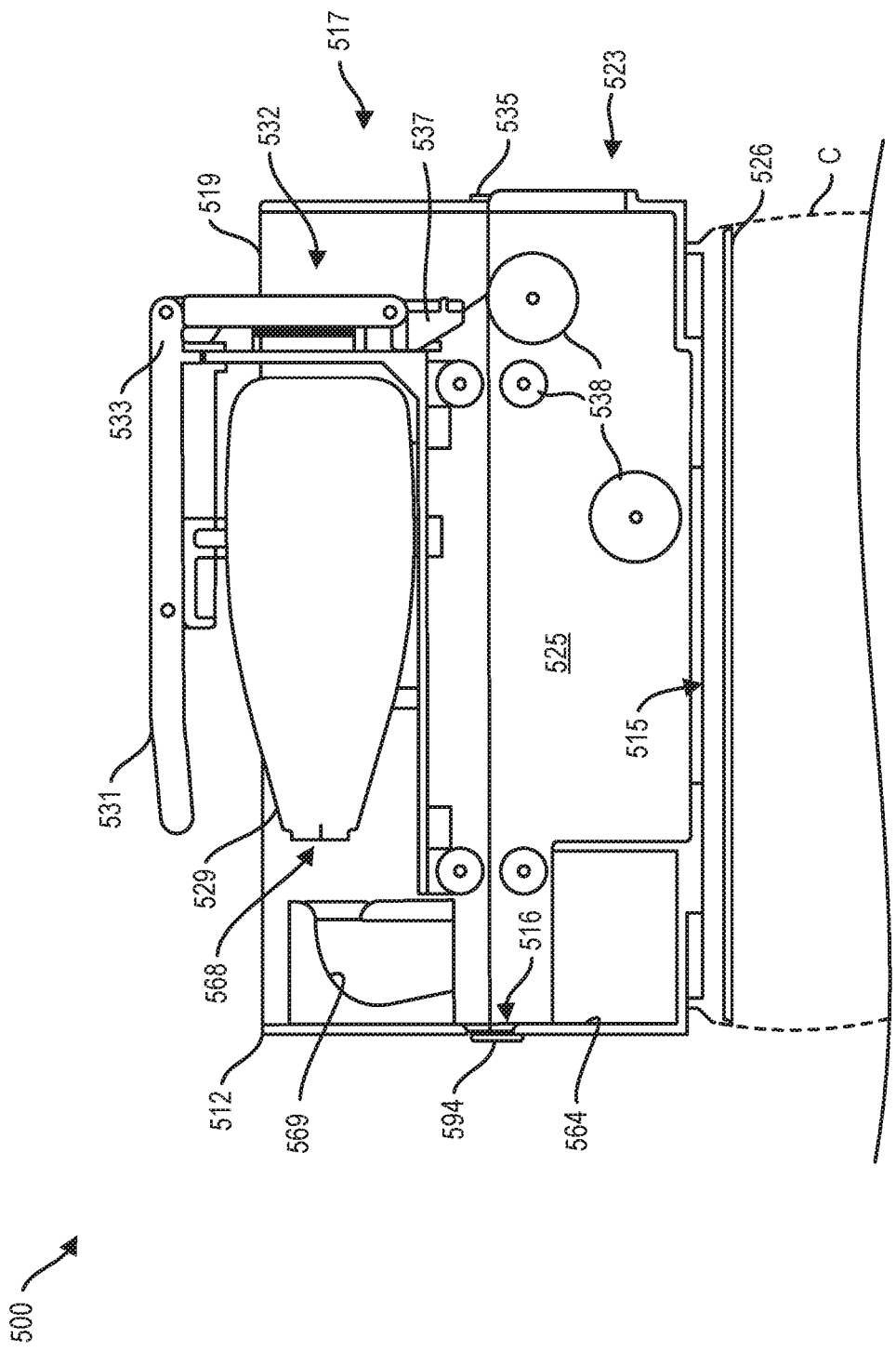
FIG. 12E is a side, cut-away view of the device of FIG. 12A incorporating an alternative actuator.
Figure 12G:
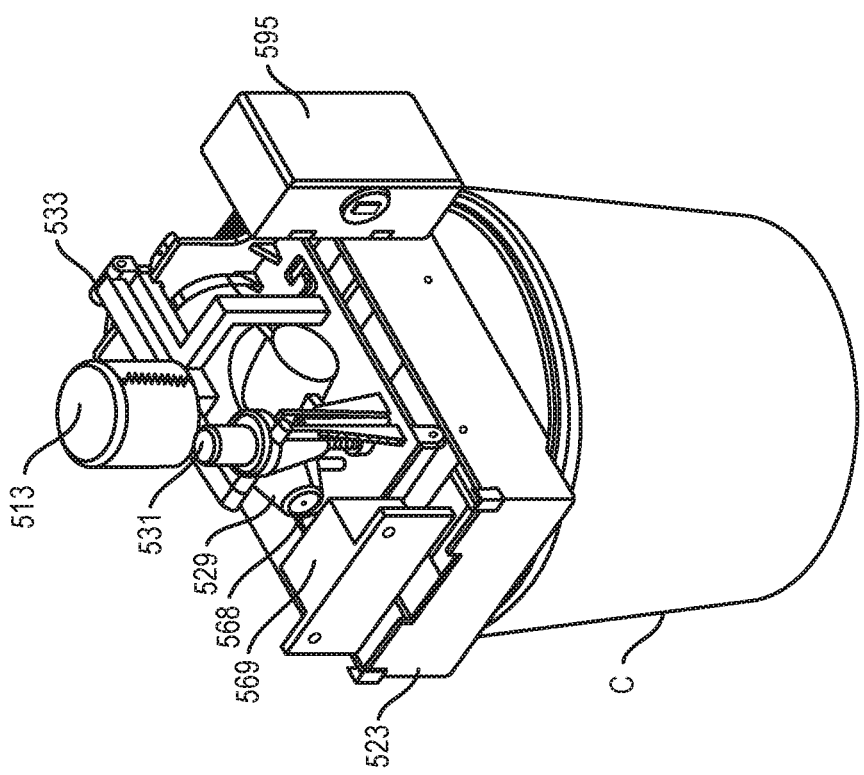
FIG. 12G is a perspective, partial view of the device of FIG. 12A.
Figure 12F:
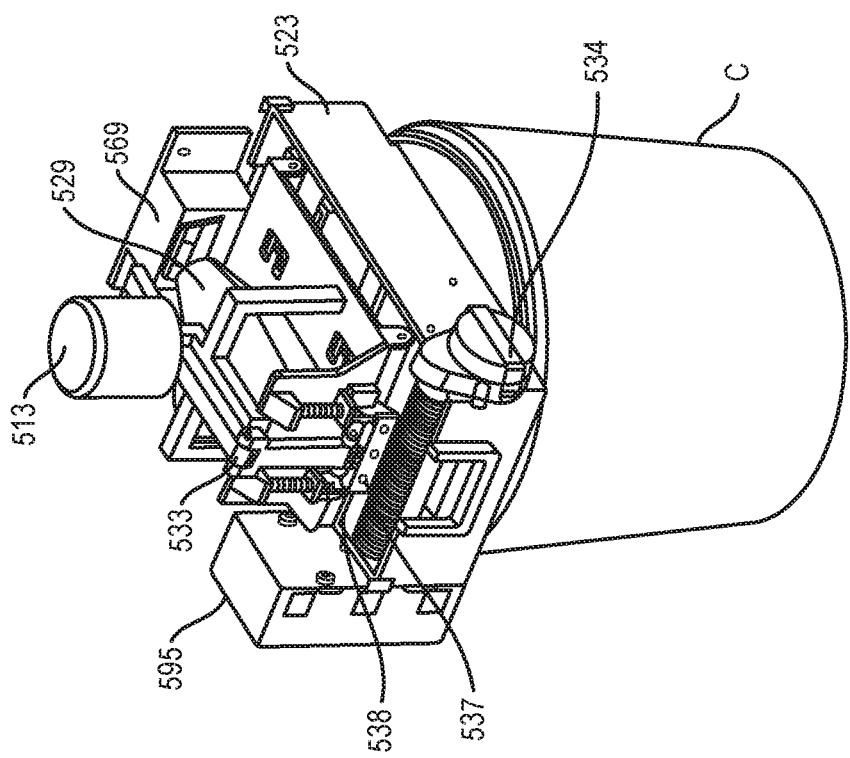
FIG. 12F is a perspective, partial view of the device of FIG. 12A.

The reservoir 14 and the application mechanism 18 can be arranged to work in concert to apply an amount of the disinfectant composition and/or the indicator composition stored within the reservoir 14 to a disinfectant article A as it is dispensed from its canister C through the dispensing aperture 16 of the device 10. The dispensing aperture 16 can be configured to allow single or multiple articles A to be dispensed through it. The dispensing aperture 16 can be a slit having a rectangular, cross, x, flower petal, or zig-zag shape. The shape of the dispensing aperture 16 can vary depending on whether the device 10 is configured for manual dispensing or automated dispensing, which will be described in more detail below. The size and shape of the dispensing aperture 16 can be selected to assist in separating the articles A from one another. Disinfectant articles A can be packaged such that they are stacked in interlocking folds or are arranged such that each sheet is connected to the other and separated by perforations. Depending on the overall configuration of the dispensing aperture 16, a plurality of flaps can be formed that are configured to compress the article A as it extends through the dispensing aperture 16. This can provide more or less volume of indicator composition to be applied to the article A, or leave more or less volume of disinfectant composition impregnated on article A, as it is dispensed through the device 10. The larger the space between the flaps of the dispensing aperture 16, the greater the volume of indicator composition and disinfectant composition maintained on the article A and vice versa. The device 10 can optionally include a dispensing mechanism 30 configured to arrange the article A in a manner that encourages uniform application of the indicator composition to the article A as the article A is fed through the interior 25 of the housing 12 towards the dispensing aperture 16. The device 10 can optionally include a mechanism that aids in separating sheets of articles A from one another. For example, a pincher mechanism can be included that pivots towards the articles A as they extend through the interior of the device 10 to capture the sheets of articles A and allow for easier separation. In some implementations, the article A is dispensed through the device 10 manually such as by a user pulling the article A through the dispensing aperture 16 (e.g. through a top surface 19 shown in FIG. 2A or a side surface 21 shown in FIG. 2C). In some implementations, the article A is dispensed through the device 10 by a dispensing mechanism 30 that is an automatic feed system including a powered motor (FIG. 12E). The dispensing mechanisms 30 will be described in more detail below. Regardless of the mechanism by which the article A is dispensed through the device 10, the article A that is dispensed has indicator composition applied.

Still with respect to FIG. 1, the application mechanism 18 of the device 10 can include a transfer element 27 and at least one applicator 29. The transfer element 27 is configured to transfer an amount of the indicator composition from the reservoir 14 to the applicator 29, which in turn is configured to apply the amount of indicator composition to the disinfectant article A dispensed through the dispensing aperture 16 of the device 10. The transfer element 27 thus drives the amount of indicator composition in a direction towards the applicator 29. The transfer element 27 can create a pressure differential between the inside of the reservoir 14 where the indicator composition is being stored and a region outside the reservoir 14. The pressure differential can be created by the transfer element 27 due to creation of a positive pressure within the reservoir 14 pushing the amount of indicator composition towards the applicator 29. The pressure differential can be created by the transfer element 27 due to creation of a negative pressure outside of the reservoir 14 pulling the amount of indicator composition towards the applicator 29. In some implementations, the transfer element 27 creates a positive pressure within the reservoir 14 by pressing on a region of the reservoir 14 or the fluid inside the reservoir 14 and causing displacement of the volume from the reservoir 14 through an outlet. The transfer element 27 can shrink the chamber volume of the reservoir 14 forcing a volume of indicator composition from the reservoir 14. The transfer element 27 can also expand a chamber volume outside the reservoir 14 causing a volume of indicator composition from the reservoir 14 to flow towards the expanded chamber. The transfer element 27 creates the pressure differential by a pumping action, either a manual pumping action or by an electric- or battery-powered motor to create the pumping action. In some implementations, a battery can be coupled to the reservoir 14 to drive the motor to create the pumping action. In the case of a manually-created pumping action, the transfer element 27 can include a trigger, button, or other actuator 31 that creates the pressure differential relative to the interior of the reservoir chamber 14 directly when pressed or squeezed or otherwise manually actuated. In the case of an electrically-powered pumping action, the transfer element 27 can include a motor powered mechanism to create the pressure differential relative to the interior of the reservoir chamber 14 upon actuation such as by a trigger, button, or other actuator 31. The transfer element 27 can also use gravity to transfer an amount of indicator composition towards the applicator 29 and need not incorporate pumping action.

As mentioned above, the applicator 29 is configured to apply the amount of indicator composition transferred by the transfer element 27 to the disinfectant article A dispensed through the device 10. The configuration of the at least one applicator 29 of the application mechanism 18 can vary. In some implementations, the applicator 29 applies indicator composition to the disinfectant article A by directly contacting the disinfectant article A such as with one or more rollers, brushes, ball-bearing devices, or other contact elements known in the art. FIGS. 3A-3B and FIGS. 4A-4N show implementations of devices incorporating direct contact style applicators. In other implementations, the applicator 29 applies indicator composition to the disinfectant article A without the applicator 29 making direct contact with the disinfectant article A, such as a sprayer, drip, atomizer, or other indirect application mechanism. FIGS. 11A-11B and FIGS. 12A-12H show implementations of devices incorporating non-contact style applicators. Each of the implementations will be described in more detail below.

As mentioned above, in certain implementations the device may include at least two reservoirs 14 or a single reservoir 14 divided into at least two separate chambers which hold volumes of different compositions which may include, for example, two solutions which when applied to the disinfectant article by actuation of the device form the indicator composition in situ on the disinfectant article; or an indicator composition and a disinfectant composition which are both applied simultaneously to the disinfectant article by actuation of the device. In accordance with these implementations, the applicator 29 may be configured to apply an amount of at least two different compositions to the disinfectant article. For example, the direct contact style applicator may be in the form of at least two rollers, brushes, ball-bearing devices, or other contact elements known in the art, such that each contact element is adapted to deliver an amount of a different composition to the disinfectant article. Preferably, the applicator 29 is in the form of two rollers. Similarly, the non-contact style applicator may include at least two sprayers, drips, atomizers, or other indirect application mechanisms configured to apply an amount of at least two different compositions to the disinfectant article.

Certain features that are described in this specification in the context of separate embodiments and implementations can also be implemented in combination in a single embodiment. Conversely, various features that are described in the context of a single embodiment can also be implemented in multiple embodiments separately or in any suitable subcombination. Moreover, although features may be described as acting in certain combinations and even initially claimed as such, one or more features from a claimed combination can in some cases be excised from the combination, and the claimed combination may be directed to a sub-combination or a variation of a sub-combination.

Direct Contact Applicators

Figure 3A:
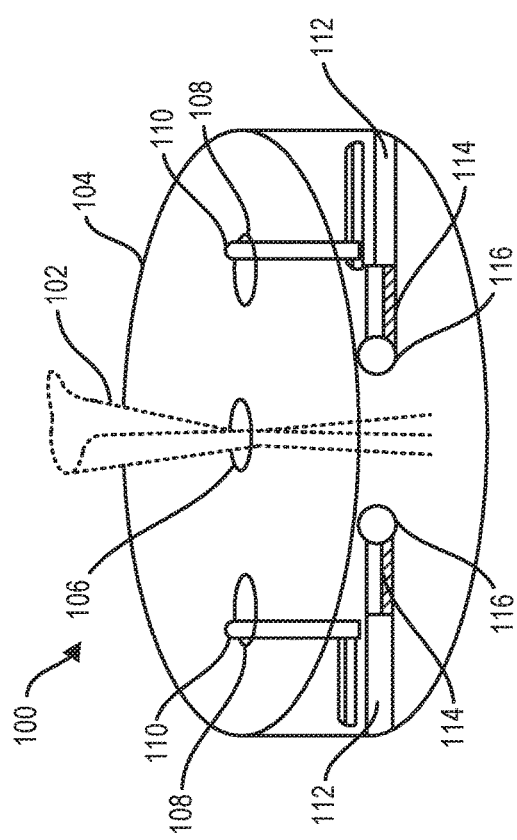
FIG. 3A is a schematic of an implementation of a device incorporating a direct contact applicator in a first configuration.
Figure 3B:
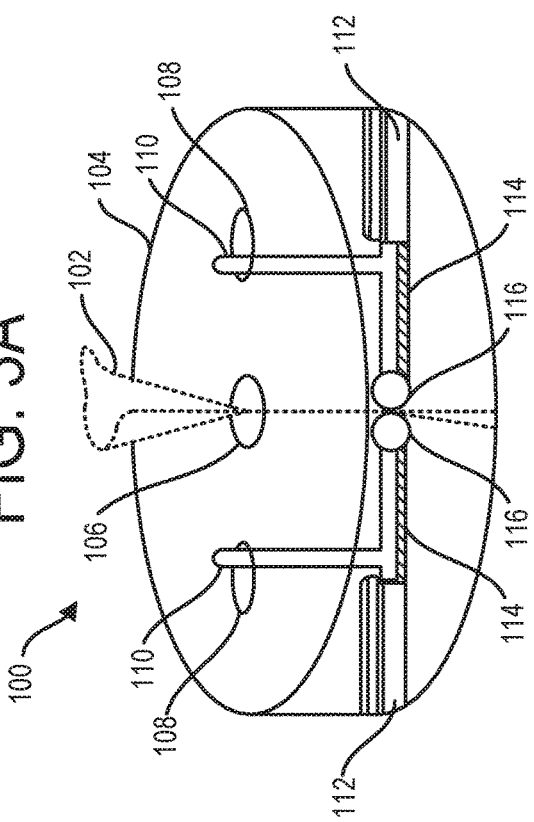
FIG. 3B is the device of FIG. 3A where the applicator is in a second configuration.

FIGS. 3A-3B illustrate an implementation of a device having a direct contact applicator. The canister dispenser may contain a separate reservoir containing an indicator composition that the disinfectant article is pulled through in order to be dispensed, thus soaking the disinfectant article with the indicator composition. In one embodiment, a roller or brush containing the indicator composition applies an amount of the indicator composition to the disinfectant article as it is dispensed through the lid. The roller preferably dispenses the disinfectant article in a flat sheet-form in order to uniformly impart the indicator composition onto the disinfectant article. Another example is a ball-bearing device inside the lid that continually applies the indicator composition to the disinfectant article as it is dispensed. FIGS. 3A-3B illustrate an example of such a ball-bearing device lid. In this implementation, the device is a ball-bearing device lid 100 comprises a lid 104, which attaches to housing containing disinfectant articles 102 that are pulled through lid opening 106. Lid 104 contains slot 108 which allows shaft 110 to be toggled. Shaft 110 is connected to reservoir 114 and held within casing 112. Casing 112 is attached to lid 104 to stabilize the device. Ball-bearing 116 is attached at the end of reservoir 114. FIG. 3A shows the ball-bearing device lid 100 in a first configuration and FIG. 3B shows the ball-bearing device lid 100 in a second configuration. Ball-bearing device lid 100 in FIG. 3B illustrates the device when shaft 110 is toggled and ball-bearing 116 is held against disinfectant article 102. As disinfectant article 102 is pulled through lid opening 106, ball-bearing 116 rolls the indicator composition onto the disinfectant article, thereby imbuing it with color. The color will fade after a pre-selected period of time after being applied to a surface. Another example includes a device or component whereby the pulling action of dispensing a disinfectant article triggers the spraying of an indicator composition from a separate reservoir onto the disinfectant article (see, for example, FIGS. 11A-11B). Yet another example is a device or component whereby the pulling action triggers the release of an indicator composition from a separate reservoir into the chamber containing the disinfectant article in order to soak it with colorant. Another device or component is a stamp or sponge treated with an indicator composition that makes contact with the disinfectant article as it is dispensed, thus imparting color onto the disinfectant article.

Figure 4D:
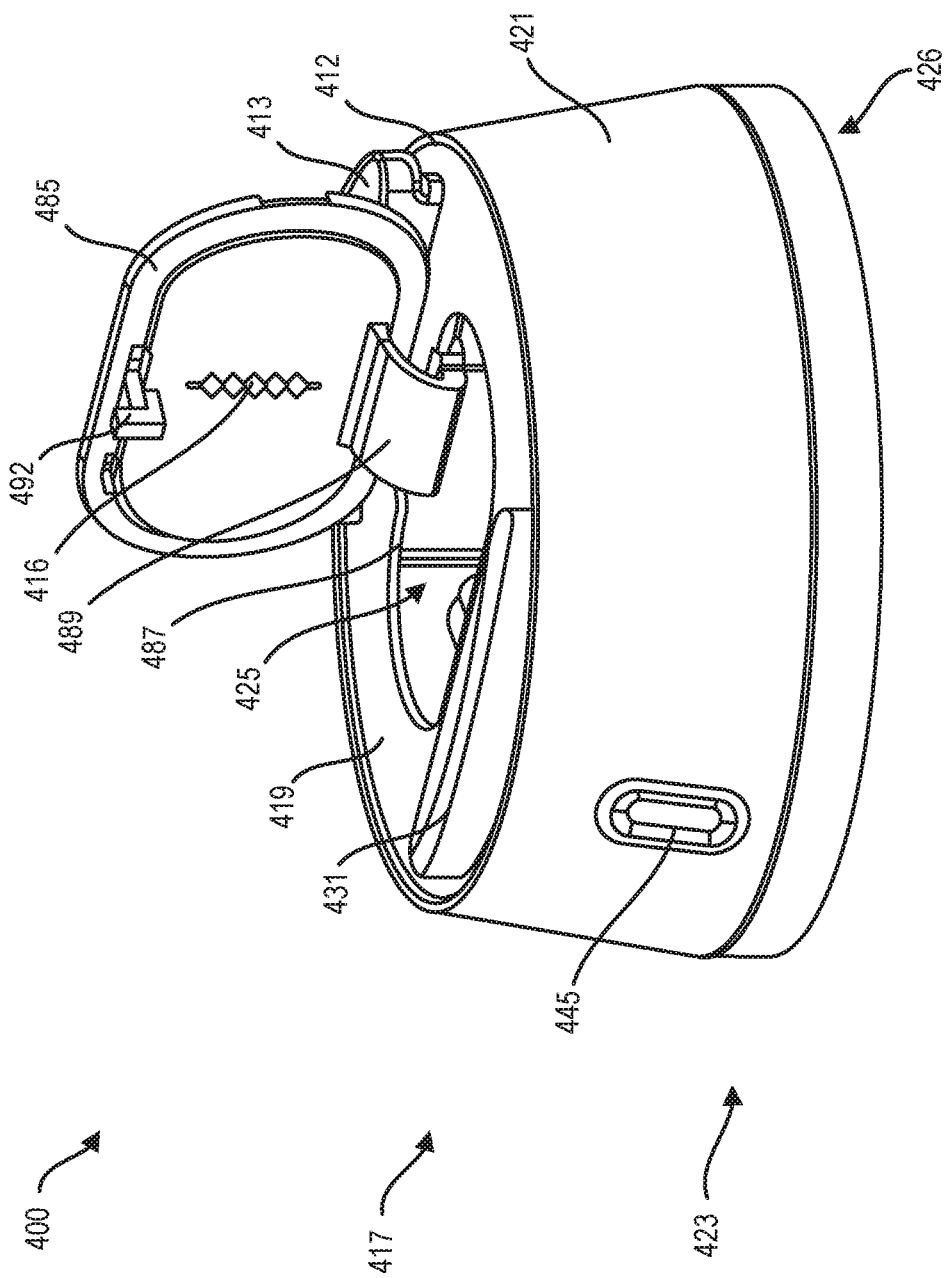
FIG. 4D is a perspective view of the device of FIG. 4A exposing an interior of the device housing.
Figure 4E:
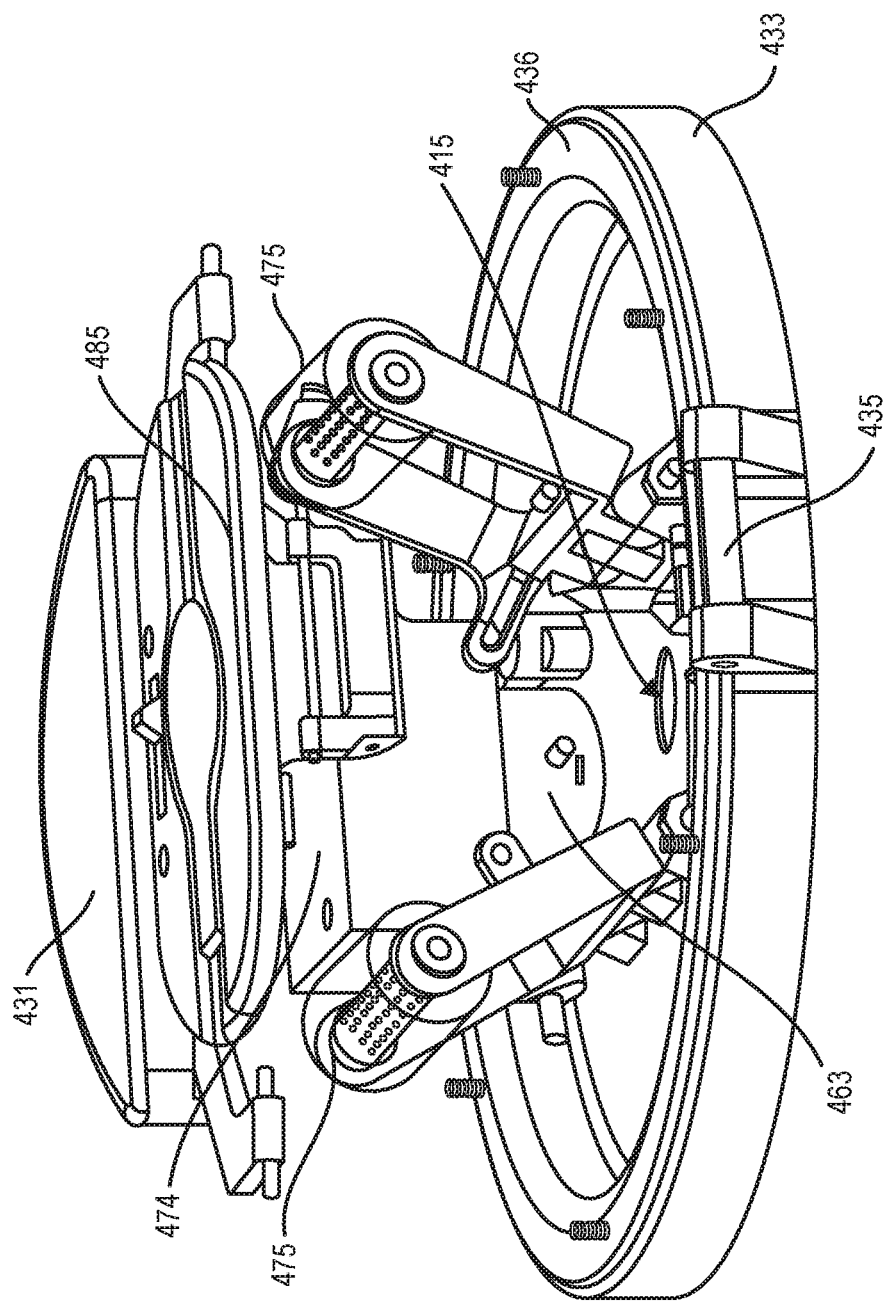
FIG. 4E is an exploded, partial perspective view of the device of FIG. 4A.
Figure 4H:
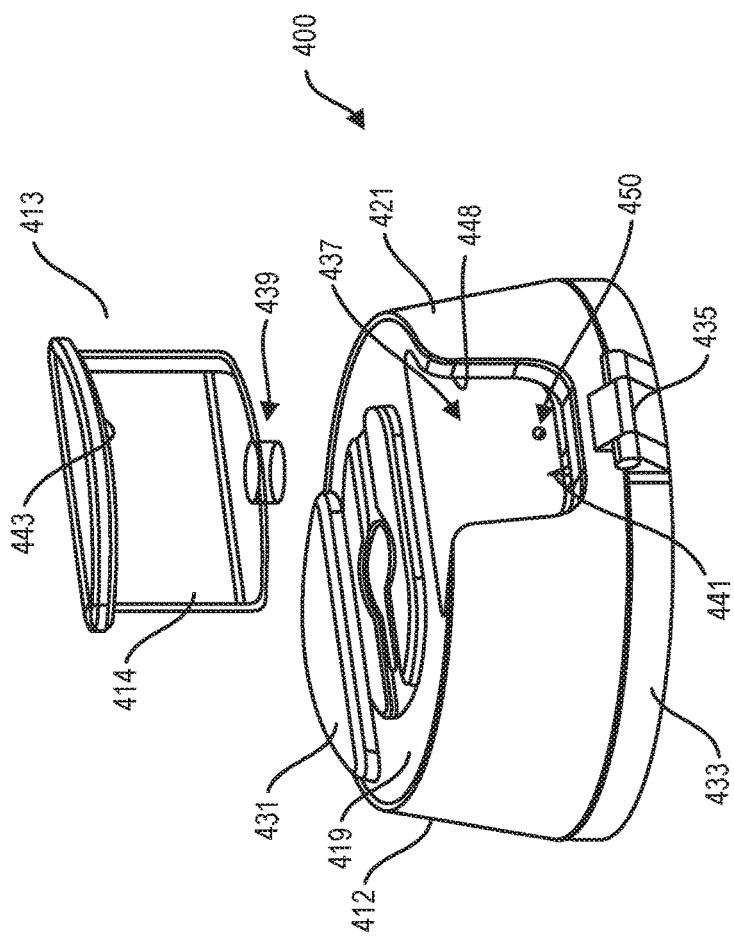
FIG. 4H is a partially exploded view of the device of FIG. 4G with a cartridge removed from the housing.
Figure 4G:
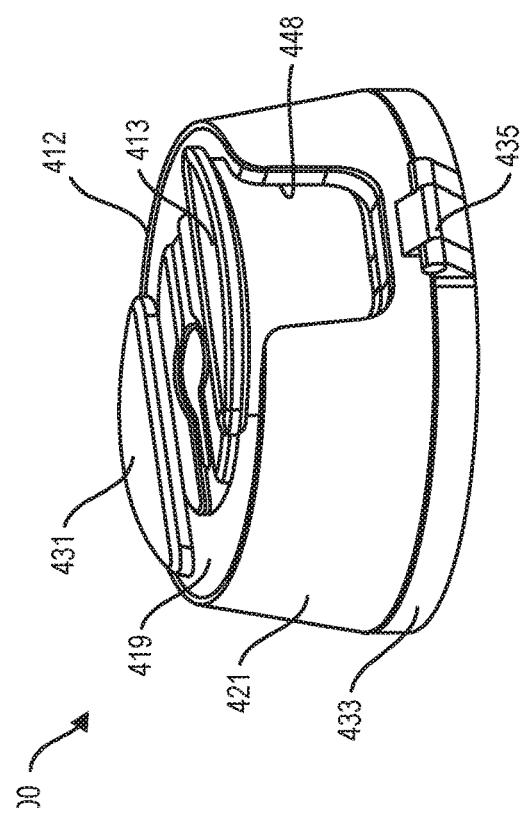
FIG. 4G is a perspective view of the device of FIG. 4A.
Figure 4I:
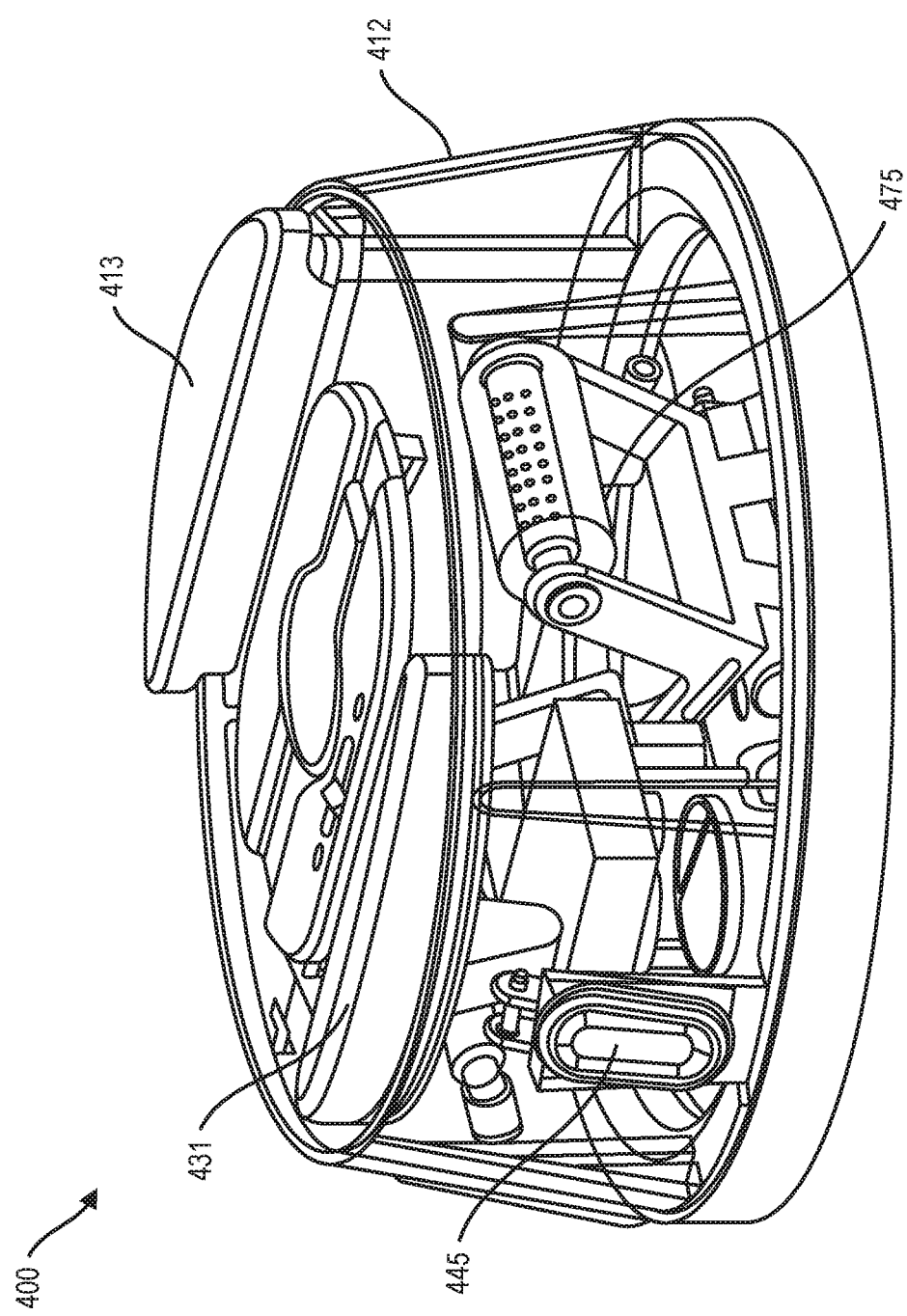
FIG. 4I is a perspective view of the device of FIG. 4A in which the housing is transparent.
Figure 4J:
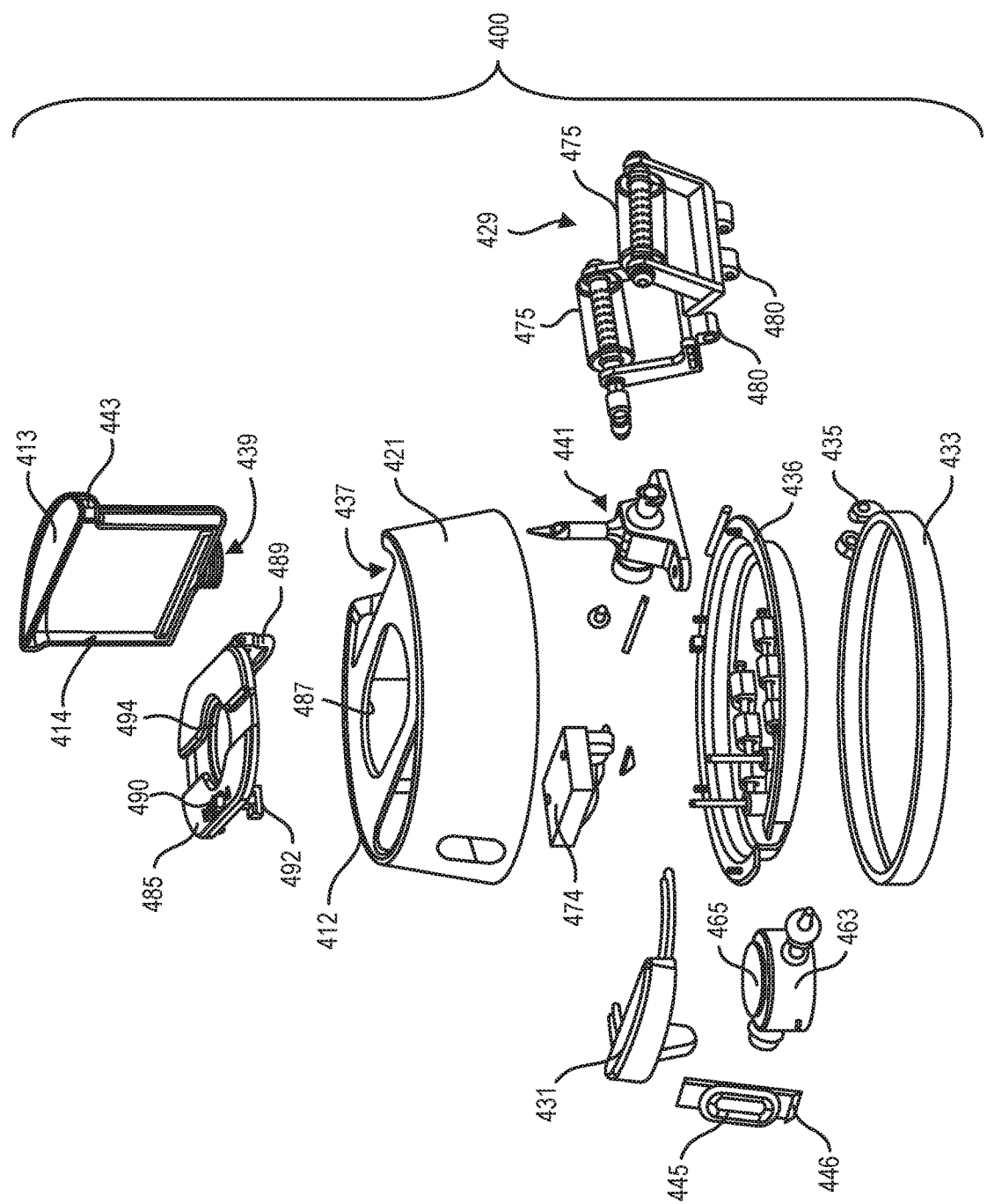
FIG. 4J is an exploded view of the device of FIG. 4A.
Figure 4K:
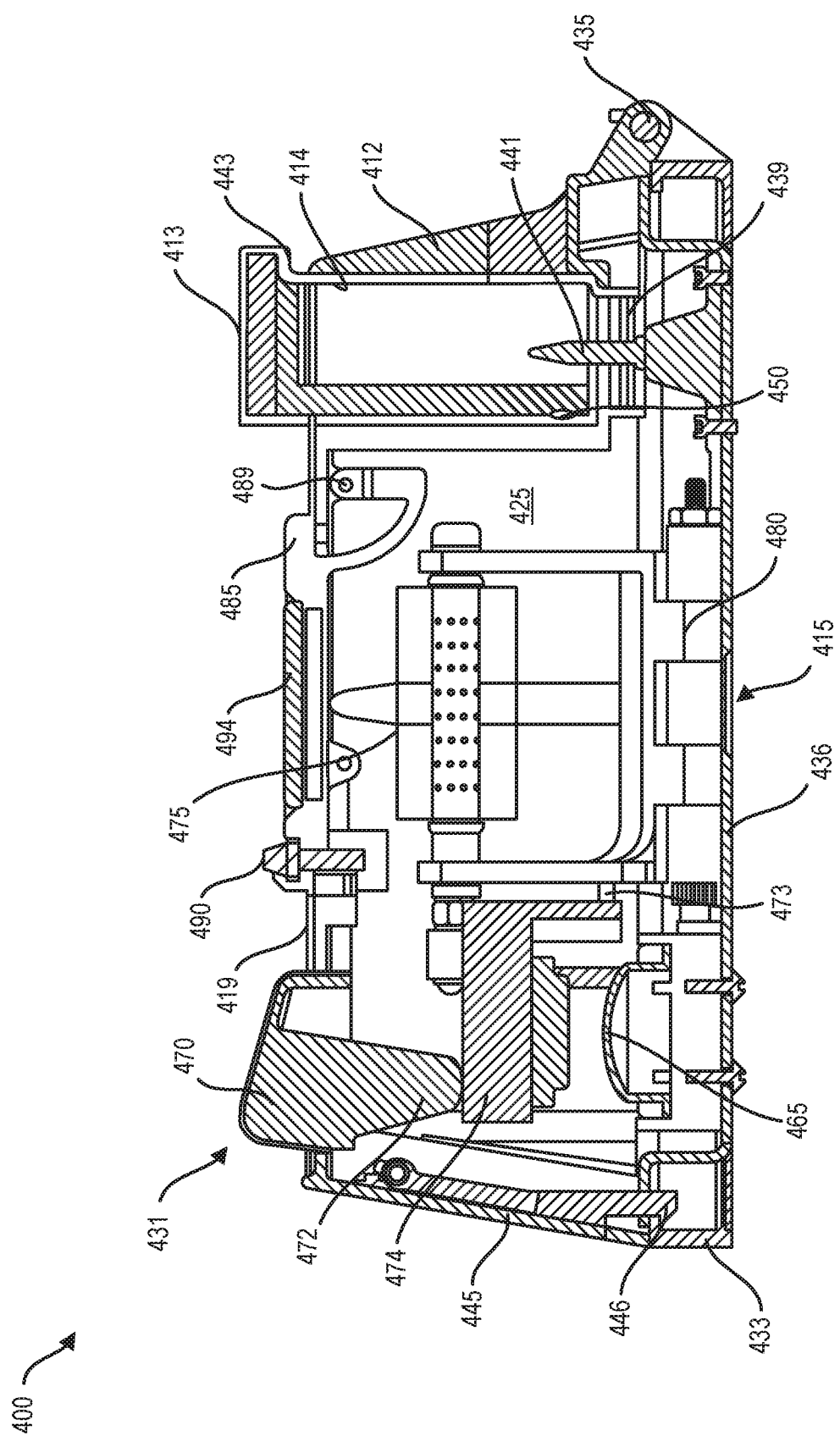
FIGS. 4K-4M are cross-sectional views of the device of FIG. 4A.
Figure 4L:
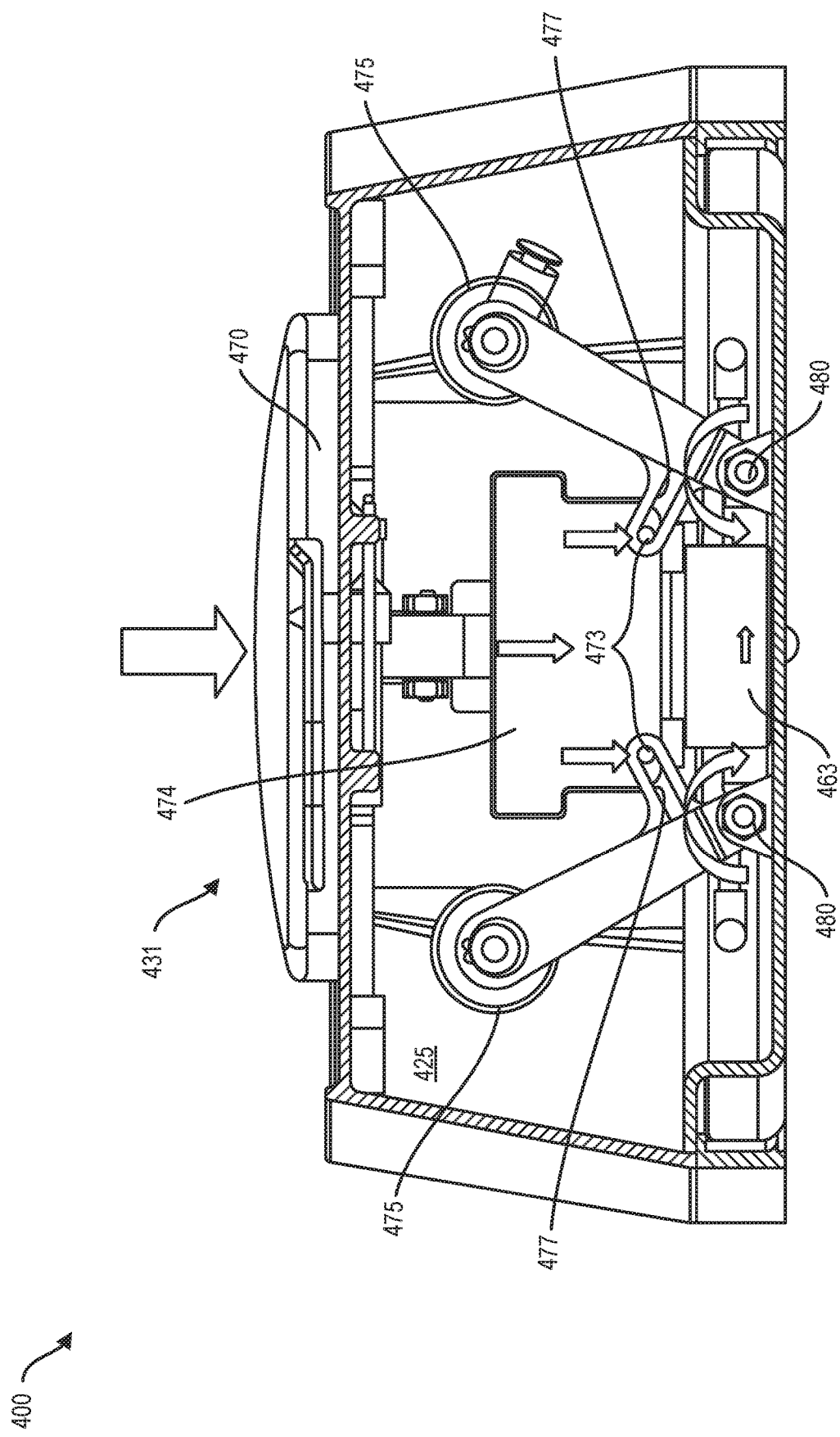
Figure 4M:
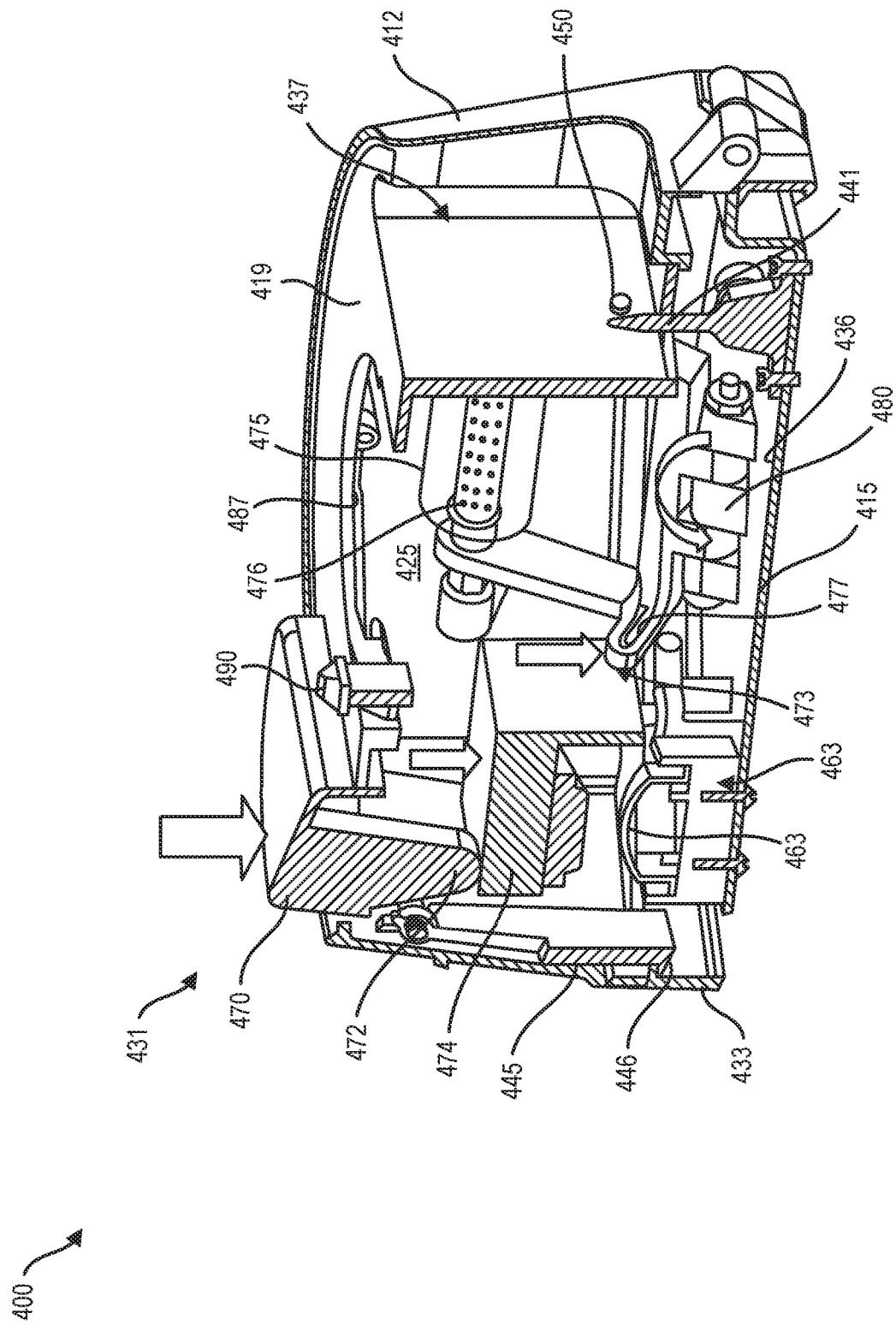
Figure 4N:
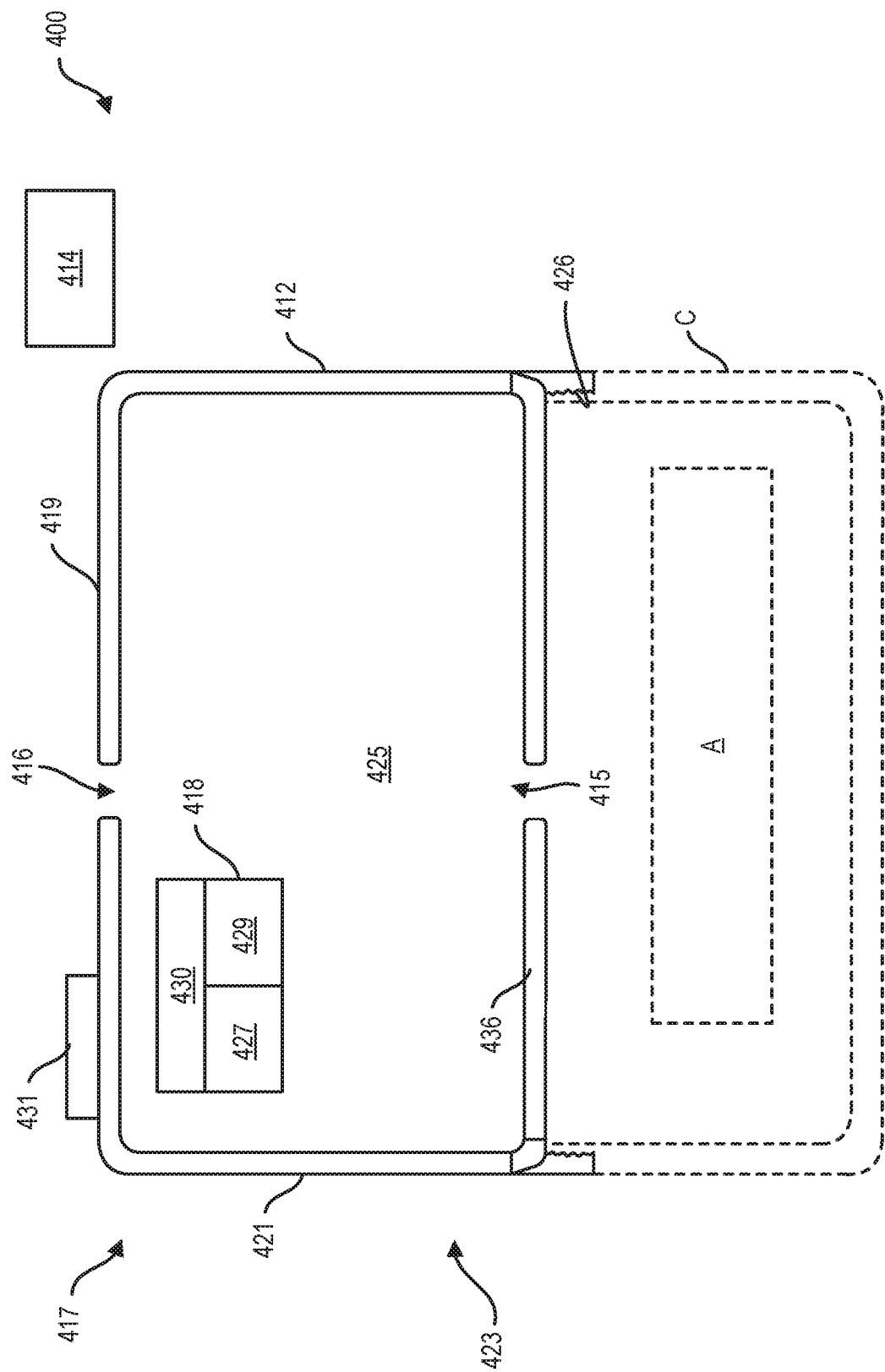
FIG. 4N is a schematic view of the device of FIG. 4A.

FIGS. 4A-4N illustrate an interrelated implementation of a device having a direct contact applicator. As with other implementations described herein, the device 400 can include a housing 412 having a dispensing aperture 416, a reservoir 414, and an application mechanism 418, each of which will be described in more detail below.

The housing 412 can include an interior volume 425 and can define a dispensing aperture 416 extending through a wall of the housing 412. In some implementations, the dispensing aperture 416 can extend through an upper surface 419 of the housing 412 (see FIG. 4D) although it should be appreciated that the dispensing aperture 416 can extend through a side surface 421. A lower end region 423 of the housing 412 can define an internal aperture or opening 415 (FIG. 4E). When the housing 412 is coupled to a region of a canister C of disinfectant articles A, the article A stored within the interior of the canister C can be drawn into the interior 425 of the housing 412 through the opening 415. The disinfectant article A can be fed through the interior 425 towards the dispensing aperture 416 in the upper end region 417 of the housing 412.

The dispensing aperture 416 can be configured to allow single or multiple articles A to be dispensed through it. The dispensing aperture 416 can be a slit having a rectangular, cross, x, flower petal, or zig-zag shape. The size and shape of the dispensing aperture 416 can vary depending on whether the device 400 is configured for manual dispensing or automatic dispensing. For example, the device 400 can include a dispensing mechanism 430 that is an automatic dispensing mechanism or manual. The dispensing aperture 416 for the automatic dispensing mechanism 430 can be a rectangular-shaped dispensing aperture 416 whereas the manually dispensed configuration may incorporate a zig-zag shaped dispensing aperture 416. The size and shape of the dispensing aperture 416 can be selected to assist in separating the articles A from one another. Disinfectant articles A can be packaged such that they are stacked in interlocking folds or are arranged such that each sheet is connected to the other and separated by perforations. Depending on the overall configuration of the dispensing aperture 416, a plurality of flaps can be formed that are configured to compress the article A as it extends through the dispensing aperture 416. This can provide more or less volume of indicator composition to be applied to the article A, or leave more or less volume of disinfectant composition impregnated on article A, as it is dispensed. The larger the space between the flaps of the dispensing aperture 416 the greater the volume of indicator composition maintained on the article A and vice versa.

Figure 5B:
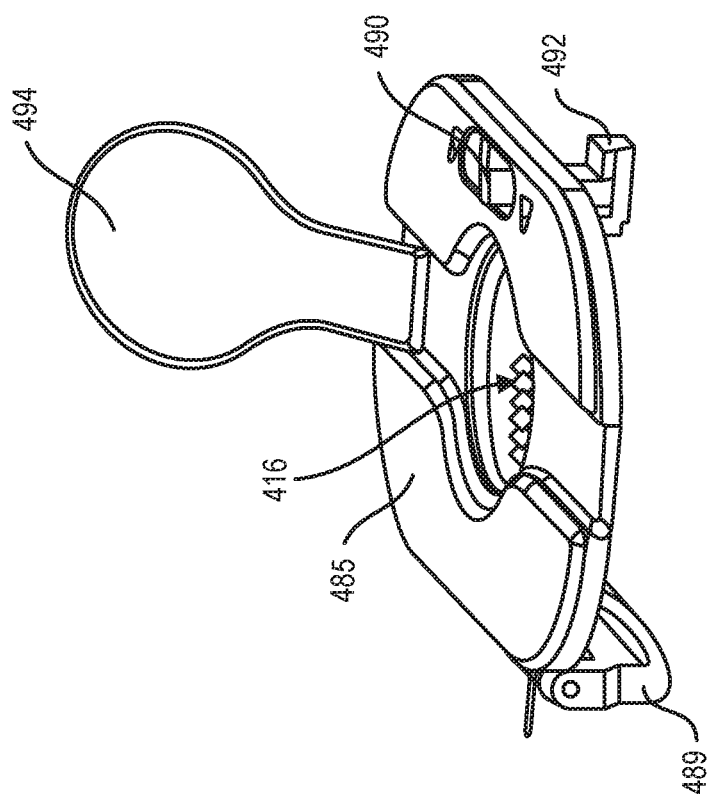
FIGS. 5A-5B are various views of a dispensing aperture in a cap of the device of FIG. 4A.
Figure 5A:
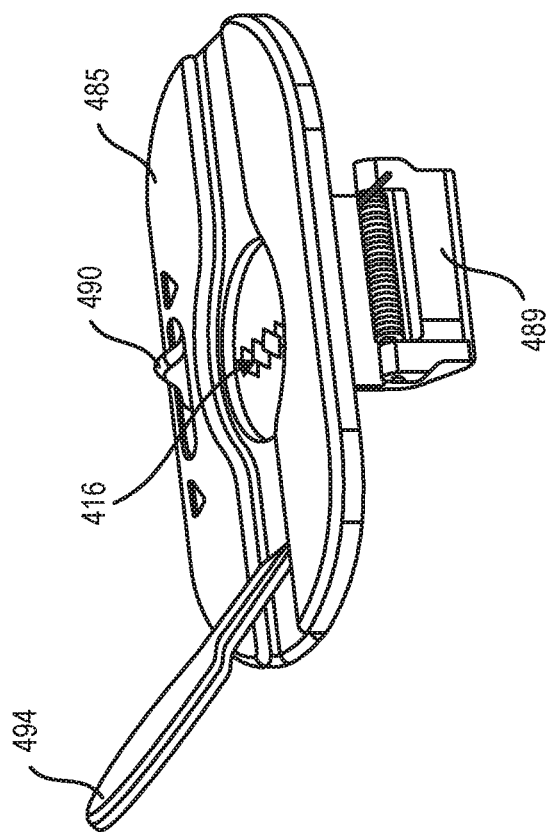

In some implementations, the dispensing aperture 416 extends through a cap 485 movably coupled to an upper surface 419 of the housing 412 (see FIG. 4B, 4C, 4D, and also FIGS. 5A-5B). The upper surface 419 of the housing 412 can define an opening 487 that is covered by the cap 485. The cap 485 can be coupled to the upper surface 419 of the housing 412 by a hinge 489 such that the cap 485 can be opened revealing an interior 425 of the housing 412 through the opening 487. The cap 485 can also include a locking element 490 having a latch 492 that can be toggled between a locked configuration keeping the cap 485 in the closed position over the opening 487 and unlocked configuration allowing the cap 485 to hinge open revealing the interior 425 through the opening 487. Opening the cap 485 can be helpful, for example, to thread the first disinfectant article A into the device 400. The cap 485 can additionally include a cover 494 over the dispensing aperture 416 to avoid inadvertent drying out of the disinfectant articles A in their canister C. The cover 494 can be hinged such that the cover 494 can be manually or mechanically opened. For example, the cover 494 can include a spring-loaded hinge that opens when an actuator is pushed. In some implementations, actuator 431 can simultaneously release the cover 494, activate the transfer element 427 to pump indicator fluid towards the applicator 429, and activate the applicator 429 to apply the transferred indicator composition to the article A. The actuator 431 can also simultaneously activate any gripper, pincher elements so that the indicator-saturated article A is released and ready for use. The cover 494 can also automatically close (and the gripper automatically released) when the actuator 431 is released to prevent the articles A within the canister C from drying out. Consolidating the various mechanisms into a single actuation simplifies use of the device 400 such that it can be used with a single hand. It should be appreciated, however, that the various components can also include their own actuator and/or be configured for manual use.

The device 400 can be configured to connect to the canister C such that the device 400 functions as a lid on an end of the canister C. The device 400 can be used to replace an existing lid on the canister C. Again with respect to FIG. 4A, a lower end region 423 of the housing 412 can incorporate one or more connecting features 426 configured to removably or detachably couple the device 400 to a canister C. The connecting feature 426 can include a thread corresponding to a thread of the canister C, a snap-fit connection, fitting, fastener, or coupling feature sized to fit a region of the canister C. The connecting feature 426 can include a bottom ring 433 sized to surround and engage with an upper rim of the canister C of the disinfectant articles A (see FIG. 4F). The bottom ring 433 can include one or more grooves, threads, snap-fit feature, or other coupling features that allows the device 400 to be attached to the canister C. In some implementations, the bottom ring 433 is a universal coupler that allows it to be attached to canisters C of various sizes. Still with respect to FIG. 4F, the bottom ring 433 can be coupled by a hinge element 435 to an upper plate 436 affixed to a lower end region 423 of the housing 412. The upper plate 436 defines the internal opening 415 through which the article A extends into the interior 425 of the device 400. A release button 445 can be incorporated that when actuated releases a latch 446 engaging the bottom ring 433. Actuation of the release button 445 moves the latch 446 thereby releasing engagement between the lower end region 423 of the housing 412 and the bottom ring 433. This allows the housing 412 to be opened and hinge relative to the bottom ring 433 when the device 400 is coupled to a canister C. This exposes the upper end of the canister C through the aperture 415 without removing the entire device 400 from the canister C. Hinging the device 400 into an opened position in this way may be helpful when a user needs to assist with priming the first article A into the device 400, which will be described in more detail below.

Figure 6B:
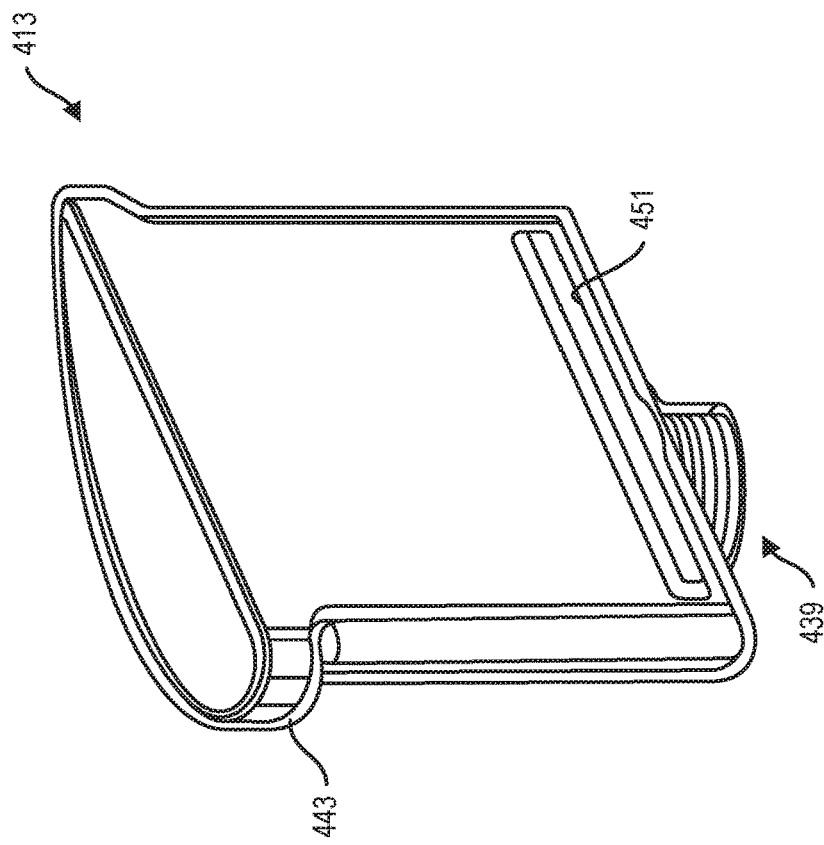
FIGS. 6A-6B are perspective views of a cartridge of the device of FIG. 4A.
Figure 6A:
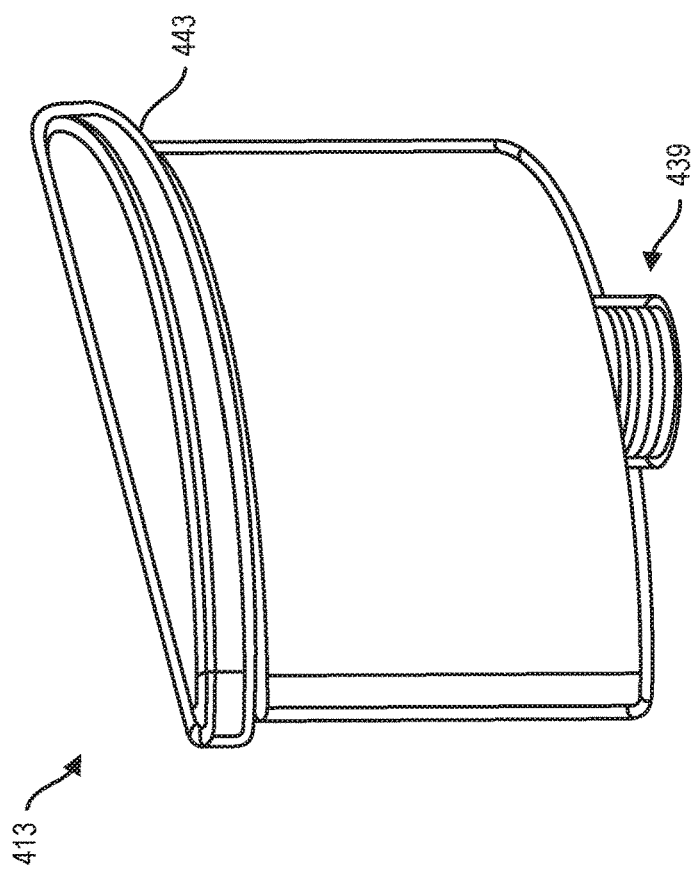

As mentioned above, the device 400 also includes a reservoir 414 having at least one reservoir chamber sized to contain an amount of indicator composition. The reservoir 414 can be located at least partially within the housing 412. The reservoir 414 can be refillable and/or removable from the housing 412. As best shown in FIGS. 4G-4H and also FIGS. 6A-6B, the reservoir 414 can be contained within a cartridge 413 configured to removably couple with a region of the housing 412. In some implementations, the housing 412 can include a receptacle region such as a slot 437 sized and shaped to receive at least a portion of the cartridge 413. The cartridge 413 can slide with the slot 437 from the top surface 419 of the housing 412 such that a coupling feature 439 of the cartridge 413 engages with a corresponding coupling feature 441 within the slot 437 of the housing 412. Engagement between the coupling features 439, 441 can result in the interior of the reservoir 414 being placed in fluid communication with at least a portion of the application mechanism 418. In some implementations, the coupling feature 439 of the cartridge 413 includes a septum or other penetrable barrier and the coupling feature 441 within the slot 437 of the housing includes a spike or other element configured to penetrate the septum. The slot 437 can also include one or more alignment features 450 configured to engage with a corresponding surface feature 451 on the cartridge 413. Engagement between the alignment feature 450 and the surface feature 451 provides a snap-in feel so the user is aware the cartridge 413 is properly in place within the slot 437 (see FIGS. 6A-6B). It should be appreciated that the cartridge 413 can engage with the housing 412 in various ways and is not limited to sliding. For example, the cartridge 413 can snap onto an exterior wall of the housing 412, can be threaded relative to the housing 412, or can be dropped into a fully enclosed channel into the interior 425 of the housing 412.

Still with respect to FIGS. 4G-4H, the reservoir 414 of the cartridge 413 can be pre-filled with indicator composition prior to use. The cartridge 413 can be a single-use disposable element or can be refilled upon emptying. The cartridge 413 can be filled in various ways. For example, the cartridge 413 can be filled through the septum of the coupling feature 439. The volume of the reservoir 414 contained within the cartridge 413 can vary, but generally, the volume is sufficient to accommodate the number of articles A provided by a single canister C. The cartridge 413 can include a fill line or other metering system visible from an exterior of the device 400 so a user can easily ascertain the remaining volume of indicator composition in the reservoir 414 of the cartridge 413. In some implementations, the side wall 421 of the housing 412 can have a cut-out 448 or other feature that reveals an outer wall of the cartridge 414 through the cut-out 448 from outside the housing 412 when the cartridge 413 is positioned within the slot 437. The cartridge 413 can include a lip 443 near the top that facilitates pulling the cartridge 413 out of the slot 437. The shape of the cartridge 413 can vary, but generally the cartridge 413 is shaped to conform to the overall shape of the housing 412 when engaged with the slot 437. The cartridge 413 can include mechanical interlocking features such that the device 400 can only be used with a specific cartridge 413 keyed to connect with the device 400. The cartridge 413 can include an encoder strip such as a bar code, QR code, RFID chip, or other feature that allows the cartridge 413 to be scanned and read by a reader device. The reader device can be a separate device or a part of the device 400. The encoder strip can also for a user to assess information about the cartridge 413 and its contents as is known in the art.

The cartridge 413 can also include more than a single reservoir 414. For example, the cartridge 413 can include multiple reservoir chambers within a single cartridge 413. The different reservoir chambers can be formed by one or more septa or inner walls extending within the interior of the cartridge 413 separating the interior into individual reservoir chambers configured to contain different compositions or components of a single composition. The different compositions in the different chambers can then be dispensed simultaneously from their respective chambers. As discussed above, the different compositions may include a disinfectant composition and an indicator composition (which may be in the form of a single part, or two parts which are combined to form the indicator).

The reservoir 414 and the application mechanism 418 are arranged to work in concert to apply an amount of the disinfectant composition and/or indicator composition stored within the reservoir 414 to a disinfectant article A as it is dispensed from its canister C through the dispensing aperture 416 of the device 400. As with respect to other implementations described herein, the article A can be dispensed from the device 400 manually such as by a user pulling the article A through the dispensing aperture 416 in the top surface 419. The article A may also be dispensed through the device 400 by an automatic feed system that includes a powered motor. The application mechanism 418 of the device 400 can include a transfer element 427 and at least one applicator 429. The transfer element 427 is configured to transfer an amount of the disinfectant composition and/or indicator composition from the reservoir 414 to the applicator 429, which in turn is configured to apply the amount of disinfectant composition and/or indicator composition to the disinfectant article A dispensed through the dispensing aperture 416 of the device 400. The transfer element 427 drives the amount of disinfectant composition and/or indicator composition in a direction towards the applicator 429. The transfer element 427 can create a pressure differential between the inside of the reservoir 414 where the disinfectant composition and/or indicator composition is stored and a region outside the reservoir 414. The pressure differential can be created by the transfer element 427 due to creation of a positive pressure within the reservoir 414 pushing the amount of disinfectant composition and/or indicator composition towards the applicator 429. The pressure differential can be created by the transfer element 427 due to creation of a negative pressure outside of the reservoir 414 pulling the amount of disinfectant composition and/or indicator composition towards the applicator 429. The transfer element 427 can create the pressure differential by a pumping action, either a manual pumping action or by an electric- or battery-powered motor to create the pumping action. In some implementations, a battery can be coupled to the cartridge 413 and/or the reservoir 414 contained in the cartridge 413 to drive a motor to create the pumping action. In the case of a manually-created pumping action, the transfer element 427 can include a trigger, button, or other actuator 431 that creates the pressure differential relative to the interior of the reservoir chamber 414 directly when pressed, squeezed, or otherwise manually actuated. In some implementations, the transfer element 427 can include a pumping element 463 that is electrically-powered by a motor to create the pressure differential relative to the interior of the reservoir chamber 414 upon actuation of a trigger, button, or other actuator 431, which will be described in more detail below.

The actuator 431 can cause the transfer element 427 and the applicators 429 to engage such that disinfectant composition and/or indicator composition can be applied to the disinfectant article A being dispensed through the device 400. The configuration of the at least one applicator 429 of the application mechanism 418 can vary. The applicator 429 can apply disinfectant composition and/or indicator composition to the disinfectant article A by directly contacting the disinfectant article A. In this implementation, the applicator 429 can be one or more rollers, brushes, ball-bearings, or other direct contact element known in the art.

Figure 7C:
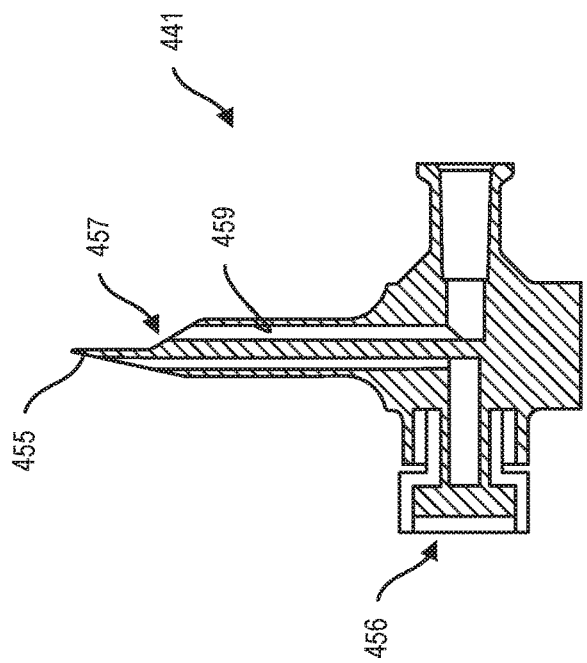
FIGS. 7A-7C are various views of a pneumatic tap of the device of FIG. 4A.
Figure 7B:
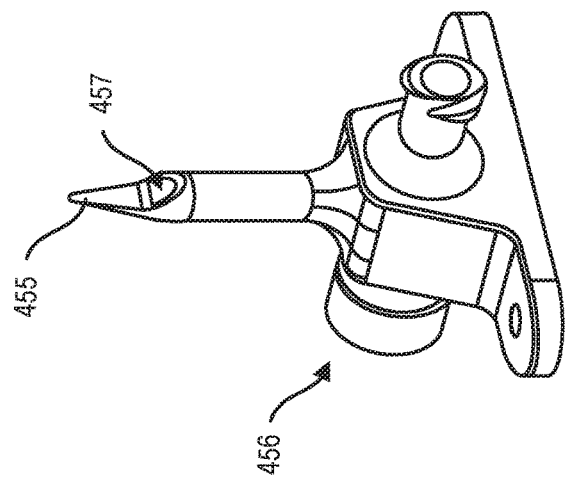
Figure 7A:
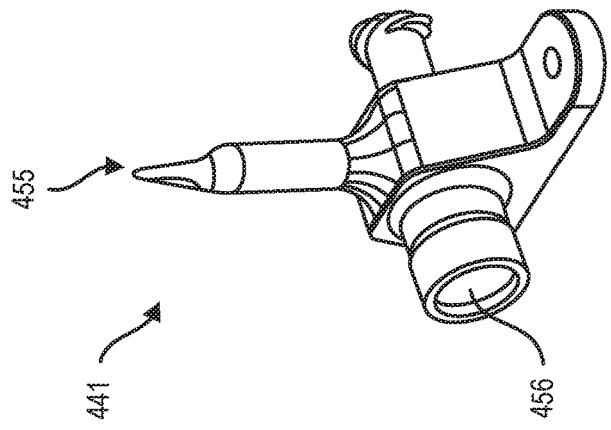

As mentioned above, the slot 437 within which the cartridge 413 is received by the housing 412 can include a coupling feature 441 configured to penetrate a lower end region of the cartridge 413. As best shown in FIGS. 7A-7C, the coupling feature 441 can be a pneumatic tap 455 having an end configured to penetrate the coupling feature 439 of the cartridge 413. The tap 455 can include at least one opening 457 into a lumen 459 extending through the tap 455 such that when the tap 455 inserts through the septum of the coupling feature 439 on the cartridge 413, the interior of the reservoir 414 is put into fluid communication with the lumen 459 of the tap 455 through the at least one opening 457. The lumen 459 of the tap 455 is configured to be in fluid communication with a conduit 461 leading to the applicator 429. A pumping element 463 can be activated to urge the indicator solution from the reservoir 414 towards the applicator 429 through the conduit 461, as will be described in more detail below. The tap 455 can also include a vent 456 or other feature to allow equilibration of pressure within the reservoir 414 upon displacement of fluid by the pumping element 463.

Figure 8B:
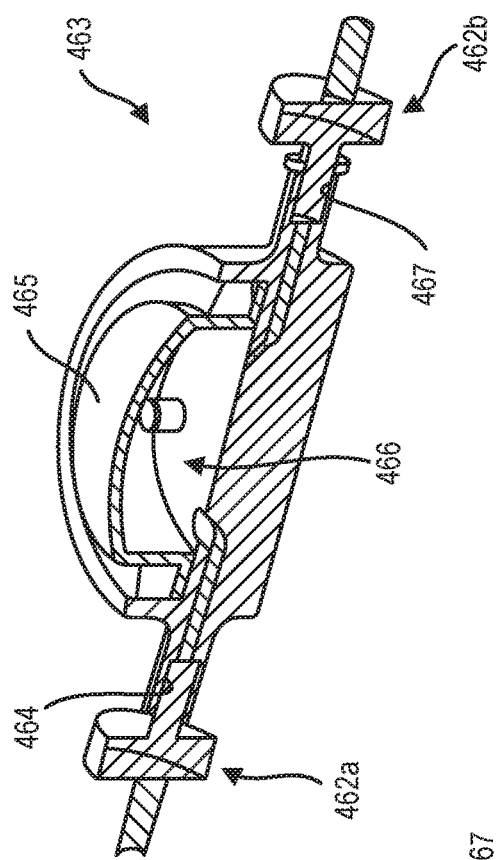
FIGS. 8A-8B are perspective and cross-sectional views, respectively, of the pumping element of the device of FIG. 4A.
Figure 8A:
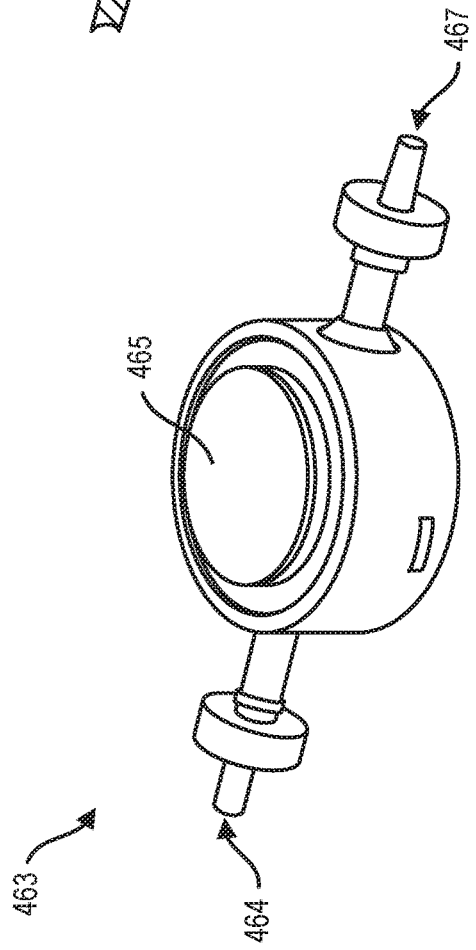
Figure 9:
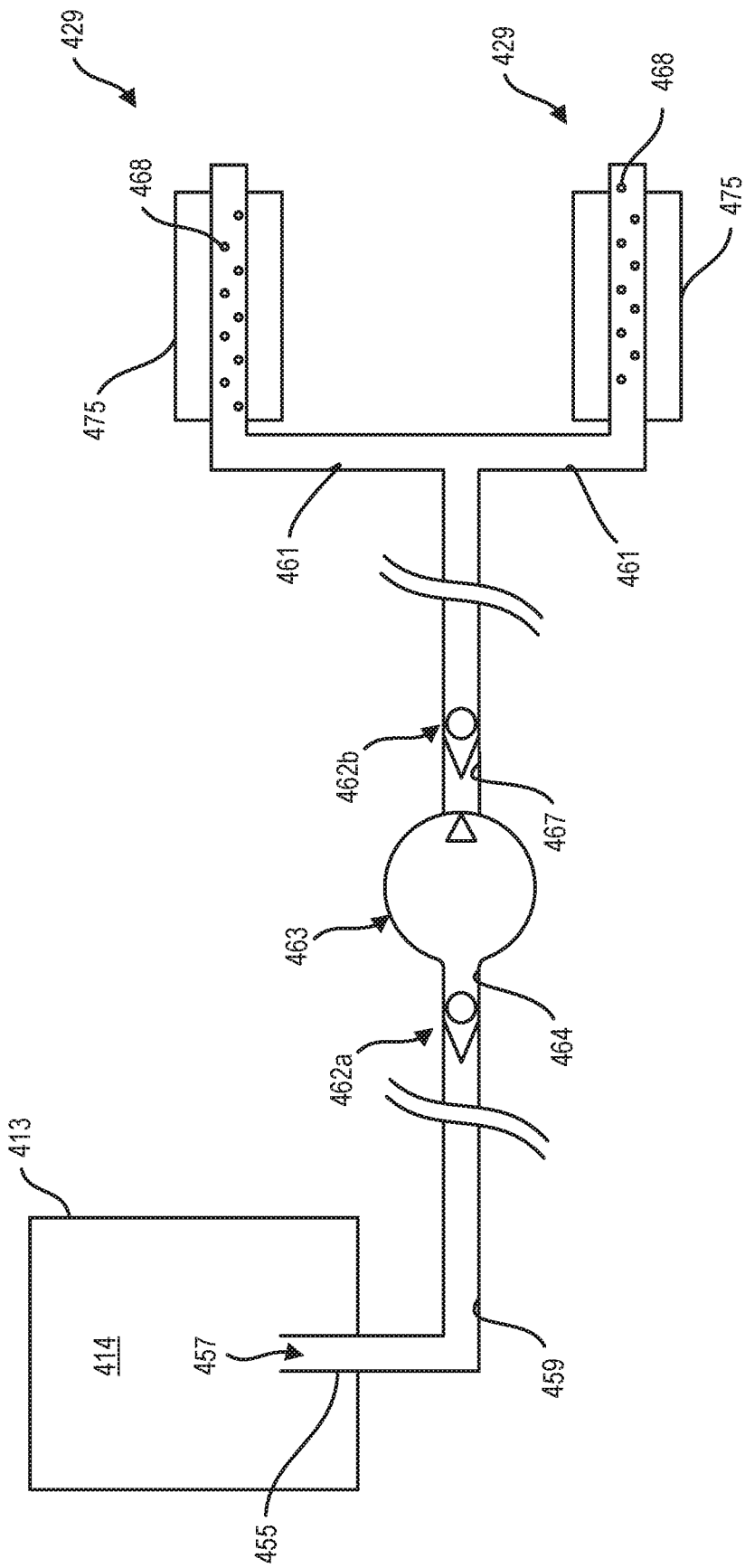
FIG. 9 is a schematic of the fluid flow through the device of FIG. 4A.

The configuration of the pumping element 463 can vary. The pumping element 463 can be a positive displacement, reciprocating, rotary, piston, diaphragm, peristaltic, dynamic, centrifugal, hydraulic, valved-gravity feed, or other pump type. The pumping element 463 can urge fluid from the reservoir 414 by positive or negative pressure. The pumping element 463 can incorporate a dosed valve that allows for gravity feed of the indicator solution towards the applicator 429. FIGS. 8A and 8B illustrate one implementation of a pumping element 463 that can cause fluid displacement from the reservoir 414 towards the applicator 429. The pumping element 463 can include a diaphragm 465, an internal chamber 466, an inlet conduit 464 leading toward the internal chamber 466, and an outlet conduit 467 leading from the internal chamber 466. The pumping element 463 can include a one-way valve 462a upstream from the internal chamber 466 within the inlet conduit 464 as well as a one-way valve 462b downstream from the internal chamber 466 within the outlet conduit 467 (see FIG. 9). The one-way valves 462a, 462b can ensure unidirectional fluid flow from the reservoir 414 towards the applicator 429. The configuration of the valves 462a, 462b can vary. In some implementations, the valves 462a, 462b are check valves. The cartridge 413 can be coupled to the device 400 such that the lumen 459 of the tap 455 is placed into fluid communication with the interior of the reservoir 414 via opening 457. As the diaphragm 465 of the pumping element 463 is displaced inward, a pressure differential is created that draws fluid from the reservoir 414 into lumen 459 via the opening 457. The fluid is directed past one-way valve 462a into the inlet conduit 464 leading to the internal chamber 466 of the pumping element 463. Fluid is ejected from the internal chamber 466 through outlet conduit 467 past one-way valve 462b toward conduit 461 leading to the one or more applicators 429. The applicator 429 can include at least one outlet 468 through which the amount of disinfectant composition and/or indicator composition displaced from the reservoir 414 is released.

Figure 10:
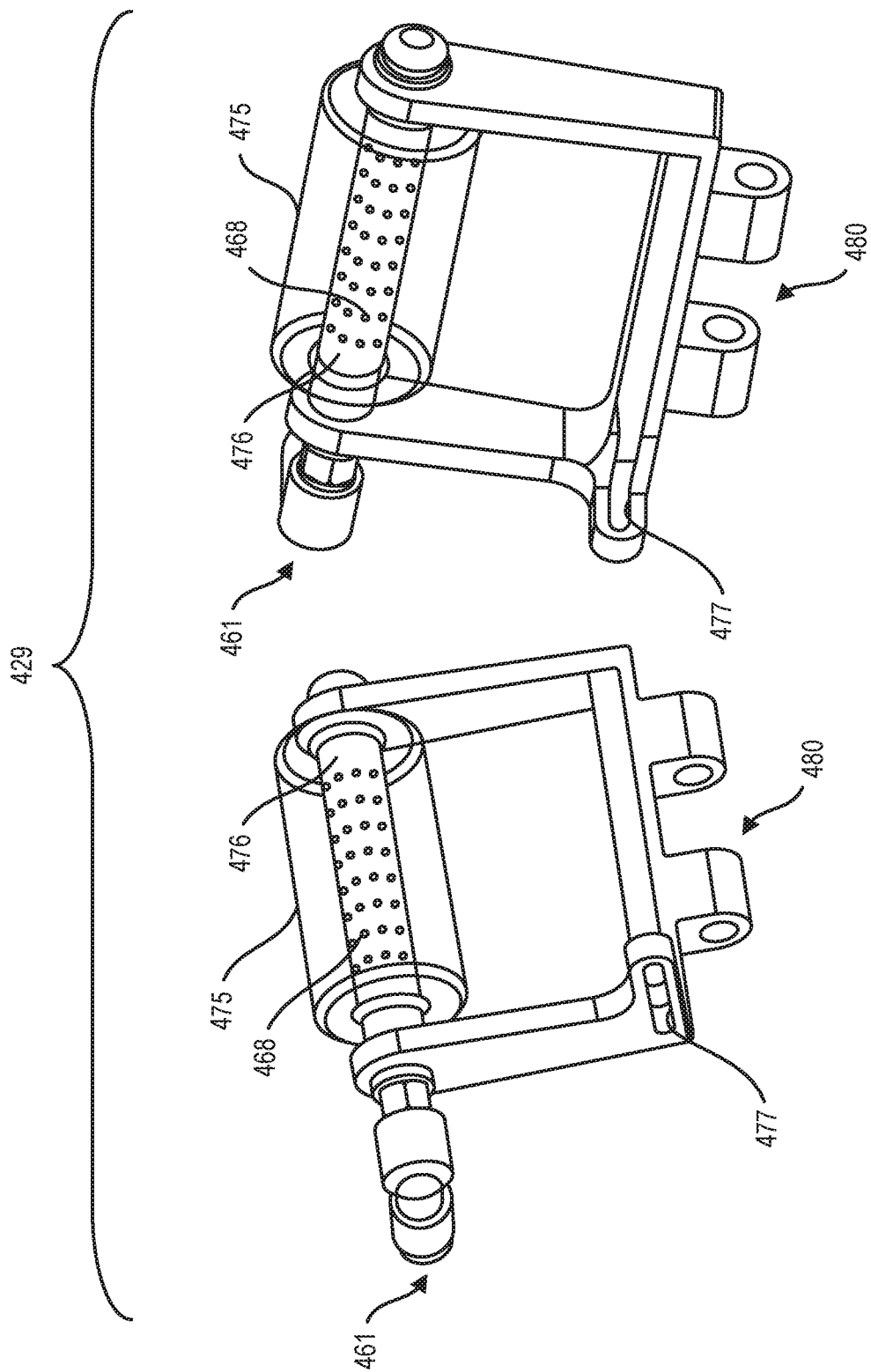
FIG. 10 is a perspective view of a pair of applicators of the device of FIG. 4A.

The device 400 can include a pair of applicators 429 (see FIG. 10). The pair of applicators 429 allows for two-sided application of the disinfectant composition and/or indicator composition to the article A. Each applicator 429 can include a roller 475 near an upper end and a hinge element 480 at a lower end. The hinge element 480 allows the applicator 429 to be moved as will be described in more detail below. In some implementations, the hinge element 480 can be shoulder bolts and include a pair of knuckles configured to receive a pin. The roller 475 can surround an inner shaft 476 through which the conduit 467 extends leading to the one or more outlets 468 formed in a wall of the inner shaft 476. As disinfectant composition and/or indicator composition is directed through the conduit 467 and out the outlets 468, the material of the roller 475 is saturated with the disinfectant composition and/or indicator composition. The material of the roller 475 can vary. Generally, the material has wicking and transfer properties and is relatively durable. The material can be relatively durable even in oxidizing or reducing environments such as in the presence of bleach. The material can have a relative high coefficient of friction with the article A. The material of the roller 475 can include foam rubber, knit, sponge formed of one or more of melamine-, polyester-, polyurethane-, polyimide-, polyethylene-, vinyl-, and polyolefin-based materials. The material of the roller 475 can include Essentra PT X-6981C, Essentra Cloth, CAPUCELL, and Magic Sponge. The material of the roller 475 can include ethylene propylene diene monomer (EPDM) foam rubber as well as various other foams such as polyimide foam, polyethelene foam, vinyl foam, Viton foam, silicone foam, ionomer foam, natural gum foam, ECH foam, and neoprene. The material of the roller 475 can include cellulose sponge, polyester wrapped fibers. The material of the roller 475 can include a coating to improve its transfer and wicking properties such as a hydrophilic coating. In some implementations, the material of the roller 475 is EPDM with a hydrophilic coating. In some implementations, the roller 475 can be a two-part roller in which an inner core of highly absorbent material, such as foam, is wrapped with a thin cloth-like material that can transfer fluid well while being very durable and have a coefficient of friction that is higher than a coefficient of friction of the article A.

As described above, the actuator 431 can simultaneously activate or move the applicators 429 and activate the transfer element 427 to pump fluid toward the applicators 429. The mechanism by which the actuator 431 engages the transfer element 427 and applicators 429 can vary. In some implementations and as shown in FIGS. 4K-4M, the actuator 431 can have an outer portion 470 that extends outside the interior 425 of the housing 412, such as through the upper surface 419 of the housing 412, and an inner portion 472 that resides within the interior 425 of the housing 412. The actuator 431 can be biased in an upward position. The actuator 431 returns to its initial upward position after being depressed by a user to a downward position and released. The inner portion 472 of the actuator 431 can lie adjacent to a slider 474 that engages both the applicators 429 and the pumping element 463. The actuator 431 is urged against an upper surface of the slider 474 or otherwise moves the slider 474 when it is depressed by a user. The slider 474 can be coupled to the applicator 429 so that the actuator 431, the slider 474, and the applicator 429 move in concert with one another. The slider 474 also activates the pumping element 463 as it is moved. This arrangement moves the rollers 475 together and pumps fluid towards the applicator 429 with a single depression of the actuator 431. It should be appreciated that the activation of the applicators 429 and/or transfer element 427 need not be mechanical and can incorporate electrical circuitry to activate the various components of the device 400.

In some implementations, the slider 474 has a pin 473 configured to insert through and slide within an elongate slot 477 of the applicator 429 (see FIGS. 4K-4M). As mentioned above, each applicator 429 can include a roller 475 at an upper end and a lower end movably coupled to the plate 436 by a hinge element 480. The pair of applicators 429 can be coupled to the plate 436 on opposite sides of the internal opening 415 through which a disinfectant article A can extend into the interior 425 of the housing 412. The applicators 429 are movably coupled to the plate 436 via their hinge element 480. The rollers 475 can be moved in a rocking motion toward and away from each other depending on whether the actuator 431 is depressed. The actuator 431 and the applicators 429 are biased into a first position where the actuator 431 is urged upward and the rollers 475 are angled outward and separated a distance away from one another. Upon depressing the actuator 431, the inner portion 472 of the actuator 431 is urged downwards against the slider 474, which in turn moves it downwards. The pin 473 slides within the slot 477 of the applicator 429 as the slider 474 is urged downwards. This causes the applicators 429 to rock from the first position in which the rollers 475 are angled outward away from one another to a second position in which the rollers 475 rock towards one another above the opening 415. As described above, the disinfectant article A extends from its canister C through the opening 415 into the interior 425 of the device 400. The rollers 475 rocked into the second position thereby contact the article A therebetween in order to transfer or imbue indicator solution onto the disinfectant article A as the article A is advanced past the rollers 475. The actuator 431 is depressed as the article A is advanced through the interior 425 and out the dispensing aperture 416. A single article A can be advanced or multiple articles A can be advanced with a single actuation of actuator 431. As mentioned elsewhere herein, the article A can be advanced manually such as by pulling action or can be advanced by a power feed system, which will be described elsewhere herein. In addition to causing the rollers 475 to rock towards one another, the movement of the actuator 431 and thus, the slider 474 can activate the pumping action of the transfer element 427 to saturate the rollers 475 with the indicator solution stored within the reservoir 414. As mentioned above, the transfer element 427 can include a pumping element 463. In some implementations, the pumping element 463 is a diaphragm pump positioned underneath the slider 474. As the slider 474 is moved downwards and urges the rollers 475 towards one another, the underside of the slider 474 is simultaneously urged against a diaphragm 465 (or otherwise activate the pumping element 463 if another type of pumping element 463). This generates a pressure differential causing fluid to be displaced from the reservoir 414 into the conduit 461 towards the rollers 475 of the applicators 429, which are being rocked towards one another to grab the disinfectant article A therebetween.

As mentioned above, hinging at least a portion of the device 400 into an opened position may be helpful when a user needs to assist with priming the first article A into the device 400. For example, the lead disinfectant article A in the canister C may be primed or engaged with the device 400 by unlocking the release button 445 to expose at least a region of the interior 425. Upon unlocking the release button 445, the upper portion 417 of the housing 412 can be opened by rotating it around the hinge element 435 exposing the opening 415 in the plate 436. The lead article A of the interconnected sheets in the canister C can be pulled through the opening 415 into the interior 425 of the housing 412. The lead article A is then threaded through the interior 425 such that the article A is brought into proximity with the applicator 429 of the application mechanism 418 (e.g. rollers or sprayer in the case of non-contact applicator). Threading the lead article A through the opening 415 can help to limit the angle at which the article A is positioned between the applicators 429, such as the rollers 475 of the applicators 429. The lead article A can be thread up between the pair of applicators 429 without coming into direct contact with the rollers 475. The leading edge of the lead article A is inserted then through the dispensing aperture 416. The locking element 490 can help thread the first or lead article A into the cap 485. After the lead article A is primed, the locking element 490 need not be used again until all the disinfectant articles A in the canister C are depleted and a new lead article A is to be primed.

Non-Contact Applicators

As mentioned above, the devices described herein can include applicators configured to apply the amount of indicator solution transferred by the transfer element to the disinfectant article dispensed through the device. The configuration of the applicators can vary depending on whether the applicator contacts the article directly or avoids coming into contact with the article. Described above are applicators that apply indicator solution to the disinfectant article by directly contacting the article such as with a roller, brush, ball-bearing, or other direct contact device. In an interrelated implementation, the applicator can apply indicator solution to the disinfectant article without the applicator making direct contact with the article, such as with a sprayer head as will be described in more detail below.

FIGS. 11A-11B illustrate an example of an interrelated device that triggers the spraying of colorant (i.e. indicator solution) during the dispensing of a disinfectant article. In one embodiment, trigger-spray device 200 includes a lid 204, which attaches to housing containing disinfectant articles 202 that are pulled through lid opening 206. When disinfectant article 202 is not being pulled, flap 208, which is connected to lid opening 206 via hinge 210, remains in a flat neutral position. Hinge 210 additionally connects flap 208 to lever 212. FIG. 11A shows the trigger-spray device 200 in a first configuration and FIG. 11B shows the trigger-spray device 200 in a second configuration. Trigger-spray device 200 in FIG. 11B illustrates the device when the wipe is pulled through lid opening 206. Flap 208 is pulled up, toggling lever 212 and pushing switch 214. Pressurized air canister 216 is then activated, drawing additive from reservoir 220 and spraying disinfectant article 202 with colorant. Reservoir 220 is stabilized to lid 204 via stabilizer 222. In certain embodiments, the lid provides the ability to switch between an active and inactive configuration. Such lids include devices or components (e.g., openings, switches, buttons) to select whether a disinfectant article should be colored or remain unaugmented. FIGS. 11A-11B demonstrate one such example wherein a manual switch can turn the coloring mechanism on or off. In certain embodiments, this lid can provide two orifices whereby one dispenses colored wipes while the other dispenses unaugmented disinfectant articles.

In certain embodiments, the device can include an external and detachable attachment to canister lids of disinfectant articles. Without limitation to the shape or size of this attachment, the device can impart color onto disinfectant articles as they are pulled through the dispenser. Preferably, the colorant is applied uniformly onto the disinfectant articles as they are dispensed. Any variety of mechanisms or methods to apply the colorant to the disinfectant articles may be used. Examples of external attachments include cones that sit atop the dispensing orifice, a shell that encapsulates the top of the container, and an attachment that clamps around the lid of the container.

FIGS. 12A-12H illustrate an interrelated implementation of a device having a non-contact applicator or an applicator configured to apply the amount of indicator solution to the article without directly contacting the article. As with other implementations described herein, the device 500 can include a housing 512 having a dispensing aperture 516, a reservoir 514, and an application mechanism 518, each of which will be described in more detail below.

The housing 512 can include an interior volume 525 and can define a dispensing aperture 516 extending through a wall of the housing 512. The dispensing aperture 516 can extend through an upper surface 519 or a side surface 521 of the housing 512. In the implementation shown in FIGS. 11A-11B the dispensing aperture is shown in the upper surface of the housing. In the implementation shown in FIGS. 12A-12H the dispensing aperture 516 is shown in a side surface 521 of the housing 512. A lower end region 523 of the housing 512 can define an internal aperture or opening 515. When the housing 512 is coupled to a region of a canister C of disinfectant articles A, the article A stored within the interior of the canister C can be drawn into the interior 525 of the housing 515 through the opening 515. The disinfectant article A can be fed through the interior 525 towards the dispensing aperture 516 in the housing 512.

The dispensing aperture 516 can be configured to allow single or multiple articles A to be dispensed through it. The dispensing aperture 516 can be a slit having a rectangular, cross, x, flower petal, or zig-zag shape. The size and shape of the dispensing aperture 516 can vary depending on whether the device 500 is configured for manual dispensing or automatic dispensing. For example, the device 500 can include a dispensing mechanism 530 that is an automatic dispensing mechanism or manual. The dispensing aperture 516 for the automatic dispensing mechanism 530 can be a generally rectangular-shaped dispensing aperture 516 whereas the manually dispensed configuration may incorporate a zig-zag shaped dispensing aperture 516 although it should be appreciated that other shapes can be used.

In some implementations, the dispensing aperture 516 can include a cover 594 positioned over the dispensing aperture 516 to avoid inadvertent drying out of the disinfectant articles A in their canister C and within the device 500 (see FIG. 12E). The cover 594 can be hinged such that the cover 594 can be manually or mechanically opened. For example, the cover 594 can include a spring-loaded hinge that opens when an actuator is pushed. The actuator 531 can simultaneously release the cover 594, activate the transfer element 527 to pump indicator fluid towards the applicator 529, and activate the applicator 529 to apply the transferred indicator solution to the article A. The actuator 531 can also simultaneously activate any gripper, pincher elements 532 so that the indicator-saturated article A is released and ready for use. The cover 594 can also automatically close (and the gripper automatically released) when the actuator 531 is released to prevent the articles A within the canister C from drying out. Consolidating the activation of the various mechanisms into a single actuation simplifies use of the device 500 such that it can be used with a single hand. It should be appreciated, however, that the various components can also include their own actuator and/or be configured for manual use.

The device 500 can be configured to connect to the canister C such that the device 500 functions as a lid on an end of the canister C. The device 500 can be used to replace an existing lid on the canister C. Again with respect to FIGS. 12A-12H, a lower end region 523 of the housing 512 can incorporate one or more connecting features 526 configured to detachably couple the device 500 to a canister C. The connecting feature 526 can be sized to surround and engage with an upper rim of the canister C of the disinfectant articles A as described above with respect to FIG. 4F in which the connecting feature 526 includes a bottom ring having one or more grooves, threads, snap-fit feature, or other coupling features that allows the device 500 to be attached to the canister C. Still with respect to FIG. 12A-12H, the housing 512 can include a lower end region 523 and an upper end region 517. The upper end region 517 can be coupled by a hinge element 535 to the lower end region 523 of the housing 512. The lower end region 523 can include a plate 536 that defines the internal opening 515 through which the article A extends into the interior 525 of the device 500. A release button can be incorporated that when actuated, releases engagement of the lower end region 523 and the upper end region 517 such that the device 500 can be opened to access the interior 525. The housing 512 can be opened to access the interior 525 even when the device 500 is coupled to a canister C. This exposes the upper end of the canister C without removing the entire device 500 from the canister C. Hinging the device 500 into an opened position in this way may be helpful when a user needs to assist with priming the first article A into the device 500.

As mentioned above, the device 500 also includes a reservoir 514 having at least one reservoir chamber sized to contain an amount of indicator composition. The reservoir 514 can also contain multiple separate chambers to hold multiple separate compositions as described above. The reservoir 514 can be located at least partially within the housing 512. The reservoir 514 can be refillable and/or removable from the housing 512. As best shown in FIG. 12A, the reservoir 514 can be contained within a cartridge 513 configured to removably couple with a region of the housing 512. The housing 512 can include a receptacle region such as a slot sized and shaped to receive at least a portion of the cartridge 513. The cartridge 513 can slide or be threaded into the slot from a surface of the housing 512 such that a coupling feature of the cartridge 513 engages with a corresponding coupling feature within the slot of the housing 512. Engagement between the coupling features can result in the interior of the reservoir 514 being placed in fluid communication with the transfer element 527. In some implementations, the coupling feature of the cartridge 513 is a septum or other penetrable barrier and the coupling feature within the slot of the housing 512 is a spike or other element configured to penetrate the septum, which will be described in more detail below. The slot can also include one or more alignment features configured to engage with a corresponding surface feature on the cartridge 513. Engagement between the alignment feature and the surface feature provides a snap-in feel so the user is aware the cartridge 513 is properly in place within the slot. Engagement between the housing 512 and the cartridge 513 can vary as is described elsewhere herein.

Still with respect to FIG. 12A, the reservoir 514 of the cartridge 513 can be pre-filled with indicator composition prior to use. The cartridge 513 can be a single-use disposable element or can be refilled upon emptying. The cartridge 513 can be filled in various ways. For example, the cartridge 513 can be filled through a septum or other feature configured to be penetrated or opened for filling. The volume of the reservoir 514 contained within the cartridge 513 can vary, but generally, the volume is sufficient to accommodate the number of articles A provided by a single canister C. The cartridge 513 can include a fill line or other metering system 511 visible from an exterior of the device 500 when the cartridge 513 is engaged with the housing 512 so a user can easily ascertain the remaining volume of indicator solution in the reservoir 514 of the cartridge 513.

The reservoir 514 and the application mechanism 518 are arranged to work in concert to apply an amount of the indicator composition stored within the reservoir 514 to a disinfectant article A as it is dispensed from its canister C through the dispensing aperture 516 of the device 500. Also as described with respect to other implementations, the application mechanism 518 can include a transfer element 527 and at least one applicator 529. The transfer element 527 is configured to transfer an amount of the indicator composition from the reservoir 514 to the applicator 529, which in turn is configured to apply the amount of indicator composition to the disinfectant article A dispensed through the device 500. The transfer element 527 drives the amount of indicator composition in a direction towards the applicator 529. The transfer element 527 can create a pressure differential between the inside of the reservoir 514 where the indicator composition is stored and a region outside the reservoir 514. The pressure differential can be created by the transfer element 527 due to creation of a positive pressure within the reservoir 514 pushing the amount of indicator composition towards the applicator 529. The pressure differential can be created by the transfer element 527 due to creation of a negative pressure outside of the reservoir 514 pulling the amount of indicator solution towards the applicator 529. The transfer element 527 can create the pressure differential by a pumping action, either a manual pumping action or by an electric- or battery-powered motor to create the pumping action. In some implementations, a battery can be coupled to the cartridge 513 and/or reservoir 514 contained within the cartridge 513 to drive a motor to create the pumping action. In the case of a manually-created pumping action, the transfer element 527 can include a trigger, button, or other actuator 531 that creates the pressure differential relative to the interior of the reservoir chamber 514 directly when pressed, squeezed, or otherwise manually actuated. In some implementations, the transfer element 527 can include a pumping element (not shown) that is electrically-powered by a motor to create the pressure differential relative to the interior of the reservoir chamber 514 upon actuation of a trigger, button, or other actuator 531, which will be described in more detail below.

The actuator 531 can cause the transfer element 527 and the applicators 529 to engage such that indicator composition can be applied to the disinfectant article A being dispensed through the device 500. The configuration of the at least one applicator 529 of the application mechanism 518 can vary. The applicator 529 can apply indicator composition to the disinfectant article A without contacting the disinfectant article A directly. In this implementation, the one or more applicators 529 can include a sprayer, or other non-contact configuration, which will also be described in more detail below. The transfer element 527 and applicators 529 work in concert with one another and with the reservoir 514 to control flow of indicator composition from the reservoir 514 to the article A.

The one or more applicators 529 of the device 500 can allow for one-sided or two-sided application of the indicator composition to the article A. The applicator 529 can include a conduit 561 having at least one outlet 568 through which the amount of indicator composition displaced from the reservoir 514 is released through the applicator 529. The applicator 529 can include any of a variety of sprayers, including the liquid sprayers described in U.S. Pat. No. 8,602,386, WO 2006/101730, and WO 2009/085175, which are each incorporated by reference herein.

The applicator 529 can be arranged relative to the dispensing aperture 516 such that spray from the outlet 568 can be directed toward the disinfectant article being dispensed through the dispensing aperture 516. In some implementations, the applicator 529 includes a spray diverter 569 positioned across from the outlet 568. The spray diverter 569 can include a surface shaped to re-direct the sprayed indicator composition exiting from the outlet 568 onto a surface of a disinfectant article A being dispensed or fed through the dispensing aperture 516. In some implementations, the spray diverter 569 is arranged above the disinfectant article A such that the spray diverter 569 re-directs the sprayed indicator composition downward onto an upper surface of the article A. The surface of the spray diverter can re-direct the sprayed indicator solution directly onto the disinfectant article A or at an angle such as by incorporating a spray diverter 569. The spray diverter 569 can allow for an even distribution of the indicator composition onto the article A. The spray diverter 569 can re-direct the sprayed indicator along any number of angles such that it drips down onto the article A. In some implementations, the angle of re-direction is between 45 degrees and 90 degrees relative to an axis of the spray discharge from the outlet 568. In other implementations, the angle of re-direction is less than 45 degrees relative to an axis of the spray discharge or greater than 90 degrees relative to an axis of the spray discharge from the outlet 568. The spray diverter 569 can have a curved surface configured to receive indicator composition from the outlet 568 against an upper region of the curved surface such that the indicator composition drips down or waterfalls along the curved surface onto the article A to achieve a more even distribution than could potentially be achieved by spraying directly onto article A. In other embodiments, outlet 568 can be coupled with a diffuser to achieve a more even distribution with or without spray diverter 568. The upper surface of the article A and the applicator 529 can be positioned generally parallel to each other and horizontal relative to the plate 536 of the device 500. An overflow container 564 can be positioned below the disinfectant article A and sized to collect excess indicator composition that is not imbued into the article A.

As mentioned above, the slot within which the cartridge 513 is received by the housing 512 can include a coupling feature configured to penetrate a lower end region of the cartridge 513. The coupling feature can include be a pneumatic tap having an end configured to penetrate the coupling feature of the cartridge 513 as described above with respect to FIGS. 4A-4N. The tap can include at least one opening into a lumen extending through the tap such that when the tap inserts through the septum of the coupling feature on the cartridge 513, the interior of the reservoir 514 is put into fluid communication with the lumen of the tap through the at least one opening. The lumen of the tap is configured to be in fluid communication with a conduit 561 leading to the applicator 529. The transfer element 527 can include a pumping element configured to urge the indicator solution from the reservoir 514 towards the outlet 568 of the applicator 529 through the conduit 561 due to creation of a pressure differential relative to the reservoir 514. The pumping element can urge fluid from the reservoir 514 by positive and/or negative pressure. The tap can also include a vent or other feature to allow equilibration of pressure within the reservoir 514 upon displacement of fluid by the pumping element. The configuration of the pumping element can vary. The pumping element can be a positive displacement, reciprocating, rotary, piston, diaphragm, peristaltic, dynamic, centrifugal, or other pump type. The pumping element can incorporate a dosed valve that allows for gravity feed of the indicator solution towards the applicator 529. The pumping element can include a manual spray mechanism that pumps the indicator solution from the reservoir 514 towards the applicator 529 by user depression of the actuator 531, such as like a manual spray bottle mechanism. For example, a user pushing on the actuator 531, such as a lever or other manual mechanism, can trigger the sprayer applicator 529 mechanically that pumps/sprays the indicator solution from the reservoir 514 onto the disinfectant article A. Additional pushes of the actuator 531 result in additional amounts of the indicator solution being transferred and applied as it is pulled out from the upper surface 519 or side surface 521.

As mentioned above, the device 500 can have a dispensing mechanism 530 that is configured for a user to manually pull the disinfectant article through the dispensing aperture 516 and/or a dispensing mechanism 530 that includes an automatic feed system having a powered drive motor 534 and a plurality of gear rollers 538. The gear rollers 538 are configured to capture and direct the disinfectant article A through the interior 525 of the device 500 towards the dispensing aperture 516. As shown in FIG. 12D, the disinfectant article A can extend from its canister C through the opening 515 into the interior 525 of the device 500. At least a first gear roller 538 of the automatic dispensing mechanism 530 can contact the article A and direct it toward one or more additional gear rollers 538 towards the dispensing aperture 515.

The application mechanism 518 of the device 500 can also incorporate a powered motor, such as a battery powered motor sprayer system. The drive motor 534 for the dispensing mechanism 530 and the motor for the application mechanism 518 can be powered by a controller 595. Any of the devices described herein can include a controller 595. The controller 595 can include at least one processor, memory, and connective circuitry or other data conduits as is known in the art to perform certain tasks and provide system logic. A power storage cell in the form of a battery that may be rechargeable may also be disposed within the housing 512, may be contained within cartridge 513, or otherwise coupled to the device. The motors and batteries of the device may be operatively coupled to the controller 595.

Regardless whether the article A is advanced using a manual dispensing mechanism 530 or an automatic or powered dispensing mechanism 530, the device 500 can include one or more grippers 532. The gripper 532 allows for a user to more easily tear the article A after dispensing. The gripper 532 can be formed of a gripper lift arm 533 and a gripper blade 537. The gripper lift arm 533 can be spring-loaded and actuated by the actuator 531. Depressing the actuator 531 can release the gripper lift arm 533 from engagement with the article A releasing it from being trapped between the gripper lift arm 533 and the gripper blade 537. The gripper blade 537 can hold the article A once a spray cycle is complete thereby preventing a user from inadvertently pulling multiple articles A through the dispensing aperture 516.

The actuator 531 can simultaneously activate the application mechanism 518, the dispensing mechanism 530, and the gripper 532. The user upon depressing the actuator 531 can advance (e.g. manually pulling or by powered gear rollers 538) the article A out the dispensing aperture 516 as indicator solution is sprayed onto the article A. Upon releasing the actuator 531, the gripper lift arm of the gripper 532 is released to return to its starting position engaged with the article A allow for easy tearing off of the article A from the remainder of the sheets.

The actuator 531 can activate the application mechanism 518, including the transfer element 527 to pump fluid toward the applicators 529, and simultaneously activate the dispensing mechanism 530 (if applicable). The mechanism by which the actuator 531 activates the application mechanism 518 and the dispensing mechanism 530 can vary. The spraying rate of the applicators 529 can be linked to the feed rate of the dispensing mechanism 530 such that the device 500 provides consistent spray volumes to the article A. The transfer element 527 can also include one or more valves, such as a piston pump with check valves that allow for consistent spray volumes. Thus, the device 500 can be a battery-powered motorized sprayer that allows for control of the amount of indicator composition applied to each disinfectant article A being dispensed. Depressing the actuator 531 activates the applicators 529 of the application mechanism 529 and also the transfer element 527 such that the spraying of indicator composition is initiated. Depressing the actuator 531 also releases the gripper 532. This allows the articles A to be pulled (or advanced automatically by motor 534) horizontally through the dispensing aperture 516 to get coated in indicator composition. When the actuator 531 is released, the gripper lift arm 533 is allowed to travel down towards the article A to clamp the article A against the gripper blade 537 such that the lead article A extending beyond the dispensing aperture 516 can be torn off or released entirely. Thus, the device 500 can be fully automated with a push of a button and without any manual pulling of the wipe. Activation of the device 500 also need not include mechanical actuation and can incorporate electrical circuitry to activate any of the various components of the device 500. The actuator 531 need not be a mechanical actuator or button that is physically depressed by a user. For example, the actuator 531 (as well as any of the actuators described herein) can be a motion sensor such that upon waving of a hand over the sensor the actuator 531 is electronically actuated in a "touchless" manner. The device 500 can additionally incorporate one or more locks to prevent inadvertent dispensing and/or application. For example, the system can incorporate an actuation lock to prevent oversaturation of the applicator 529 and/or the disinfectant article A due to excessive pumping when an article A is not removed from the device 500.

Hinging the housing 512 of the device 500 into an open position may be helpful when a user needs to assist with priming the lead or first article A into the device 500. For example, the upper end region 517 of the housing 512 can be coupled by a hinge element 535 to the lower end region 523 of the housing 12 (see FIG. 12C). The upper end region 517 can hinge open by and the lead disinfectant article A in the canister C may be primed or engaged with the device 500. Upon unlocking a release button, for example, the upper portion 517 of the housing 512 can be opened by rotating it around the hinge element 535 exposing the opening 515 in the plate 536. The lead article A of the interconnected sheets in the canister C can be pulled through the opening 515 into the interior 525 of the housing 512. The lead article A is then threaded through the interior 525 such that the article A is brought into proximity with the applicator 529 of the application mechanism 518 by threading the article A through the plurality of guide rollers 538 so that the article A lies horizontally underneath the flow diverter 569 such that the diverter directs the solution onto the article A (see FIG. 12D). The leading edge of the lead article A is inserted then through the dispensing aperture 516.

Indicator Compositions and Methods for Disinfecting a Surface

The indicator compositions described here are adapted to impart a color to the disinfectant solution that is visible after its application to a surface for a pre-defined period of time, for example from 5 to 120 seconds, or from 2-5 minutes, or from 5-10 minutes, or from 10-30 minutes. Compositions are provided that are optimized for post-application color duration in order to address the user's requirements. For example, a user decontaminating a large surface area may require a longer color duration in order to avoid areas that have already been treated while ensuring complete coverage of the entire area. In another example, the color duration may be chosen to correspond to the contact time needed to inactivate a pathogen, such as a 0.5% sodium hypochlorite solution requiring 3 minutes to kill *Clostridium difficile.*

In embodiments, the disclosure provides methods for disinfecting a surface by applying a solution of a disinfectant and an indicator composition via a disinfecting article as described herein and waiting for a period of time until the color of the solution has faded to clear, thereby disinfecting the surface. In embodiments, the surface may be porous or nonporous surface. In embodiments, the surface may be concrete, steel, wood, ceramic, polypropylene, plastics, glass, metals, granite, etc. In embodiments, the surface may be a fabric. In embodiments, the surface may be skin.

The indicator compositions described here are formulated to provide a defined post-application color duration, also referred to herein as a 'time to fade' meaning the time required for the colored indicator solution to fade to colorless after application to a surface. Various combinations of ingredients are utilized to 'tune' the color duration of the compositions depending on the nature of the disinfectant solution, its concentration, and the desired duration of color following application to a surface. For example, the presence of an alkaline builder, either alone or in combination with a surfactant, increases the pH of the solution to slow down the oxidation of the pigment, thereby slowing its de-colorization. In embodiments, the alkaline builder is present in sufficient amounts to increase the pH of the solution to a range between about pH 9 to about pH 14. For certain disinfectants, such as sodium hypochlorite or calcium hypochlorite, the addition of an alkaline builder as a dye stabilizer functions by shifting the equilibrium of active chemical species towards the less reactive species. For example, sodium hypochlorite (NaOCl) in aqueous solution contains different chlorine species that have different reactivities. HOCl predominates at acidic pH and is roughly 1000 times more reactive than the other species, $OCl^-$, which predominates at basic pH. By incorporating an alkaline builder into a colored disinfectant like sodium or calcium hypochlorite, the ratio of $OCl^-$ to HOCl will increase, resulting in less reactivity towards the dye in solution. Without wishing to be bound by theory, it is believed that upon application of an indicator composition as described here to a surface and its exposure to air, acidic carbon dioxide in the air will neutralize the alkalinity of the indicator composition, thereby initiating decolorization of the dye.

In embodiments, further additives, such as a rheology modifier (also referred to as a thickening agent), may be included in the indicator composition to modulate the color-fading reaction, for example by slowing acidification upon exposure to atmospheric carbon dioxide and thereby slowing the decolorization of the dye.

In general, the workable ranges of the oxidizable pigment, and any optional additional ingredients such as surfactant, alkaline builder, etc., will vary depending on both the strength of the oxidizing solution and the desired period of time to fade after the solution is applied to a surface. Illustrative embodiments of how the compositions described here can be adapted for different disinfecting agents, provide different times of color persistence in the bulk solution, and take different times to fade after application to a surface are described in the embodiments below, and in the Examples. In general, for the same disinfecting agent of a different strength, the same compositions as described below may be used, but more or less of the composition will be added to the disinfecting solution, depending on whether it is more or less dilute than the illustrative embodiments provided here.

As discussed in more detail in the following sections, the disclosure provides indicator compositions adapted to the type of dye combined with the type of disinfectant in order to provide for a colorized disinfectant solution that fades within a predetermined period of time after application to a surface via a disinfecting article. For example, in embodiments where the indicator is applied to a disinfectant article saturated with sodium hypochlorite, the indicator is a single aqueous solution of a dye and one or more additional components such as an alkaline builder, hydrotrope, rheology modifier, or surfactant serve to modulate the fade time. In these compositions, the dye reacts directly with the sodium hypochlorite and begins to fade. The other ingredients serve to adjust the rate of fade and thereby reduce or extend the time to fade for a particular composition.

In other embodiments, for example, where the indicator is applied to a disinfectant article saturated with a quaternary ammonium/alcohol disinfectant, the disclosure provides two separate solutions, A and B, which are mixed upon application to the disinfectant article immediately prior to use. Quaternary ammonium compounds and alcohols are not strong oxidizing agents like sodium hypochlorite, so for these compositions a separate agent, such as an oxidizing agent or a reducing agent, is introduced to decolorize the pigment. In exemplary embodiments, solution A contains a pigment and an optional catalyst such as HTAB, ferrous sulfate, copper (II) sulfate, or copper (II) sulfide caved superstructures, and solution B contains the decolorizing agent. When the solutions are combined to form the indicator, the decolorization of the pigment is initiated. Exemplary oxidizing agents for use as decolorizing agents include peracetic acid, sodium perchlorate, hydrogen peroxide, and bismuth silver oxide; and exemplary reducing agents include ascorbic acid and sodium sulfite.

In yet other embodiments, the indicator is a pH-dependent pigment such as thymolpthalein, which begins to fade on its own upon exposure to an acidic environment like the wiped surface or atmospheric carbon dioxide. In accordance with this embodiment, an alkaline builder may be employed to modulate the rate of fade. For example, in embodiments, the indicator composition comprises an aqueous solution of 1-8 w/w thymolpthalein and 0.5-4 w/w alkaline builder such as sodium hydroxide. In accordance with these embodiments, the fade time of the indicator solution following its application to a surface via a disinfectant article saturated with 0.55% sodium hypochlorite, 0.65% sodium hypochlorite, 0.3% quat/21% alcohol, 0.5% quat/55% alcohol, or 70% alcohol is from about 5-15 minutes. The amount of the indicator composition applied to the disinfectant article is about 0.0015 ml/cm$^2$. See e.g., Example 1.

Further exemplary embodiments of the indicator compositions are provided in the following sections.

Indicator Compositions for Hypochlorite-Based Disinfectants

In embodiments, the disclosure provides an indicator solution comprising a water-soluble pigment, and optionally one or more of a surfactant, an alkaline builder and a rheology modifier, suitable for colorizing a disinfectant article pre-soaked with a disinfectant solution of 0.2-1% sodium hypochlorite or calcium hypochlorite. In embodiments, the disinfectant solution is 0.4-0.7% sodium hypochlorite, or 0.525%, 0.55%, or 0.63% sodium hypochlorite. In embodiments, the disinfectant solution is 0.55% or 0.65% sodium hypochlorite.

In embodiments, the indicator is suitable for application to a disinfectant article saturated with a 0.2-1% sodium hypochlorite solution, and the indicator further comprises one or more surfactants and optionally an alkaline builder or a rheology modifier, or both. In embodiments, the pigment is FD&C Blue 1.

In embodiments, the water soluble pigment is selected from FD&C Blue 1, Acid Green 50, Acid Green 25, Patent Blue V, FD&C Yellow 6, Fast Green FCF, Indigo Carmine, Acid Blue 80, Remazol Brilliant Blue R, Coomassie Brilliant Blue, Crystal Violet Lactone, Thymolphthalein, Bromothymol Blue, Methylene Blue, FD&C Red 2, and mixtures thereof.

In embodiments, the pigment is FD&C Blue 1 in an amount of 0.1-5 wt %. In embodiments, the FD&C Blue 1 is present in the indicator solution in an amount of 0.25 wt %, 0.5 wt %, 0.75 wt %, 1 wt %, 1.25 wt %, 1.5 wt %, 1.75 wt %, 2 wt %, or 2.5 wt %. In embodiments, the pigment is Acid Green 50 in an amount of 0.1-5 wt %. In embodiments, the Acid Green 50 is present in the indicator solution in an amount of 0.25 wt %, 0.5 wt %, 0.75 wt %, 1 wt %, 1.25 wt %, 1.5 wt %, 1.75 wt %, 2 wt %, or 2.5 wt %.

In embodiments, the surfactant is selected from one or more of sodium dodecyl sulfate (SDS), sodium xylene sulfonate (SXS), sodium laureth sulfate (SLES), sodium myreth sulfate (SMS), sodium cholate, an acetylenic diol (e.g., Surfynol™ 104S), alkyldiphenyloxide disulfonate (e.g., DOWFAX™ 2A1), or sodium toluene sulfonate (STS). In embodiments, the surfactant is selected from SXS and SDS, and mixtures thereof. In embodiments, the surfactant, or mixture of surfactants, is present in the indicator solution in an amount of from 0.05-5 wt %, or from 0.1-3 wt %, or from 0.15-8 wt %. In embodiments, the surfactant, or mixture of surfactants, is present in the indicator solution in an amount of from 0.5-2 wt %.

In embodiments, the alkaline builder is selected from sodium hydroxide (NaOH), calcium hydroxide (Ca(OH)$_2$), potassium hydroxide (KOH), lithium hydroxide (LiOH), and mixtures thereof. In embodiments, the indicator solution does not contain an alkaline builder.

In embodiments, the rheology modifier is selected from sodium alginate, glycerol, guar gum, locust bean, dextran, cellulose, carrageenan (lambda, iota, kappa), sodium carbonate, fumed silica, alkali swellable emulsions, hydrophobically modified alkali swellable emulsions, hydrophobically modified polyurethanes, sodium polyacrylate, and mixtures thereof. In embodiments, the rheology modifier is lambda carrageenan. In embodiments, the rheology modifier is present in the indicator solution in an amount of from 0.05-5 wt %, or from 0.2-0.4 wt %. In embodiments, the rheology modifier is present in the indicator solution in an amount of 0.2 wt %, 0.3 wt %, 0.4 wt %, or 0.5 wt %. In embodiments, the indicator solution does not contain a rheology modifier.

In embodiments, the composition optionally further comprises one or more of a catalyst and a perfume. In embodiments, the catalyst is a reactive oxygen species generating catalyst selected from sodium nitrate, potassium nitrate, sodium nitrite, and titanium dioxide. In embodiments, the total amount of catalyst in the composition, if present, is 3-40% w/w, preferably 3-10% w/w, based on total weight of the composition. In embodiments, the ratio of catalyst to water-soluble pigment in the composition is from 0.50:1 to 5:1. In embodiments, the perfume is selected from citric acid, benzoic acid, and acetic acid. In embodiments, the total amount of perfume in the composition, if present, is 2-30% w/w, preferably 2-10% w/w, based on total weight of the composition. In embodiments, the ratio of perfume to water-soluble pigment in the composition is from 0.25:1 to 20:1, preferably from 0.5:1 to 4:1.

In embodiments, the indicator composition comprises 0.1-5% w/w FD&C Blue 1, preferably about 1.5% w/w FD&C Blue 1, and optionally 0.05-5% w/w SXS, preferably about 0.75% w/w SXS, wherein the SXS is present either alone or in combination with 0.1-3% w/w SDS, preferably about 0.3% w/w SDS, or in combination with 0.05-5% w/w lambda carrageenan, preferably about 0.4% w/w lambda carrageenan. In one embodiment, the indicator solution comprises 1.2-2% FD&C Blue 1 in deionized water, without additional additives. In accordance with any of these embodiments, the fade time of the indicator solution following its application to a surface via a disinfectant article is from about 2-5 minutes. The amount of the indicator composition applied to the disinfectant article is about 0.0015 ml/cm$^2$. See e.g., Examples 7, 8.

In embodiments, the indicator composition comprises an aqueous solution of 0.75-1.5% w/w FD&C Blue 1 and a surfactant selected from 0.25-0.5 w/w SXS, 0.25-0.75% w/w SDS, and combinations of SXS and SDS, wherein the total amount of surfactant is a range of from about 0.6-0.8% w/w. In accordance with these embodiments, the fade time of the indicator solution following its application to a surface via a disinfectant article is from about 2-3 minutes. The amount of the indicator composition applied to the disinfectant article is about 0.0015 ml/cm$^2$. See e.g., Example 2.

In embodiments, the indicator composition comprises an aqueous solution of 0.75-1.5% w/w FD&C Blue 1, 0.5-1% w/w alkaline builder, such as sodium hydroxide, and, optionally, 0.25-0.75% w/w SDS as a surfactant. In accordance with these embodiments, the fade time of the indicator solution following its application to a surface via a disinfectant article is from about 3-4 minutes. The amount of the indicator composition applied to the disinfectant article is about 0.0015 ml/cm$^2$. See e.g., Example 3.

In embodiments, the indicator composition comprises an aqueous solution of 0.75-1.5% w/w FD&C Blue 1, 0.5-1% w/w alkaline builder, such as lithium hydroxide, and, optionally, 0.25-0.75% w/w SDS as a surfactant. In accordance with these embodiments, the fade time of the indicator solution following its application to a surface via a disinfectant article is from about 3-4 minutes. The amount of the indicator composition applied to the disinfectant article is about 0.0015 ml/cm$^2$. See e.g., Example 4.

In embodiments, the indicator composition comprises an aqueous solution of 0.75-1.5% w/w Acid Green 50 and a surfactant selected from 0.25-0.5% w/w SXS, 0.25-0.75% w/w SDS, and combinations of SXS and SDS, wherein the total amount of surfactant is a range of from about 0.6-0.8% w/w. In accordance with these embodiments, the fade time of the indicator solution following its application to a surface via a disinfectant article is from about 1-3 minutes. The amount of the indicator composition applied to the disinfectant article is about 0.0015 ml/cm$^2$. See e.g., Example 5.

In embodiments, the indicator composition comprises an aqueous solution of 0.5-2.5% w/w FD&C Blue 1, 0.25-1% w/w surfactant, such as SDS, and optionally 0.2-5% w/w lambda carrageenan. In accordance with these embodiments, the fade time of the indicator solution following its application to a surface via a disinfectant article is from about 1-5 minutes. The amount of the indicator composition applied to the disinfectant article is about 0.0015 ml/cm$^2$. See e.g., Example 6.

Indicator Compositions for Alcohol-Based Disinfectants

In embodiments, the disclosure provides an indicator solution comprising a water-soluble pigment, and optionally one or more of a surfactant, an alkaline builder and a rheology modifier, suitable for colorizing a disinfectant article pre-soaked with an alcohol-based disinfectant solution such as an ethanol-based disinfectant solution or an isopropyl alcohol-based disinfectant solution. In embodiments, the disinfectant solution is 70% ethanol or 63% isopropyl alcohol.

In another embodiment, the indicator is suitable for application to a disinfectant article saturated with an alcohol, such as 70% ethanol or 63% isopropyl alcohol, and the pigment is selected from thymolphthalein, methylene blue, and 3,3-bis-(4-hydroxy-3-ethylphenyl)-1-(3H)-isobenzonfuranone. In accordance with these embodiments the indicator may optionally also include a reducing agent such as sodium sulfite or ascorbic acid.

In embodiments, the indicator composition comprises from about 0.1-10% w/w, preferably about 0.5% w/w, thymolphthalein in a solution of either 70% ethanol or 63% isopropyl alcohol and provides a fade time of from about 5-30 seconds or from 15-60 seconds, respectively.

In embodiments, the indicator composition comprises from about 0.1-10% w/w, preferably about 0.16% w/w, thymolphthalein in a solution of 1.5M NaOH and either 70% ethanol or 63% isopropyl alcohol, wherein the ratio of NaOH to alcohol is about 70:30, and the composition provides a fade time of from about 15-60 seconds.

In embodiments, the indicator composition comprises from about 0.1-20% w/w, or preferably about 0.5% w/w 3,3-bis-(4-hydroxy-3-ethylphenyl)-1-(3H)-isobenzonfuranone in a solution of either 70% ethanol or 63% isopropyl alcohol and the composition provides a fade time of from about 0.5-5 minutes.

In embodiments, the indicator composition comprises from about 0.25-1% w/w, or preferably about 0.5% w/w methylene blue and from about 10-33%, or preferably about 27% sodium sulfite, with the remainder being deionized water, and the composition provides a fade time of from about 15-120 seconds, and wherein the composition is suitable for application to human skin.

Indicator Compositions for Quaternary Ammonium/Alcohol Based Disinfectants

In embodiments, the indicator is suitable for application to a disinfectant article saturated with 0.2-1% of a quaternary ammonium compound and 5-75% alcohol. In embodiments, the disinfectant article is saturated with 0.3% of a quaternary ammonium compound and 21% alcohol, or 0.5% of a quaternary ammonium compound and 55% alcohol.

In embodiments, the indicator composition is an aqueous solution comprising a water-soluble pigment and one or more of a catalyst, peracetic acid, and hydrogen peroxide. In embodiments, the pigment may be selected from methylene blue, malachite green, indigo carmine, Acid Green 25, Acid Green 50, FD&C Blue 1, pinacyanol chloride, rhodamine B, alpha naphthol orange, azo violet, and thymolphthalein. Preferably, the catalyst is a reactive oxygen species generating catalyst such as hexadecyltrimethylammonium bromide (HTAB), ferrous sulfate sodium nitrate, potassium nitrate, sodium nitrite, copper (II) sulfate pentahydrate, copper (II) sulfide caved superstructures, iron (III) nitrate nonahydrate, copper (II) sulfide, and iron (II) sulfate.

In embodiments, the indicator solution is an aqueous solution comprising a water-soluble pigment and one or more of an alkaline builder, such as sodium hydroxide (NaOH), a reducing agent, such as ascorbic acid or sodium sulfite, a pH modifier, and an oxidizing agent, such as sodium persulfate or bismuth silver oxide.

In one embodiment, the indicator composition comprises from about 0.5-5% w/w, or preferably about 1% w/w thymolphthalein in a solution of 70% ethanol, and 1-5% w/w of an alkaline builder, for example NaOH.

In embodiments, the disclosure provides an article of manufacture adapted for use with the devices described here, which contains an indicator composition in the form of two separate solutions which, upon mixing, form the indicator. In embodiments, the article of manufacture comprises a reservoir as described herein, the reservoir having two chambers for holding the two separate solutions, A and B. In an embodiment, the separate solutions, A and B, are each applied to a separate member of a pair of the applicator element of a device described here. In embodiments, each member of the pair is a roller or a spray device. The two solutions are combined upon actuation of the device to trigger the applicator element to apply each solution, A and B, to the disinfectant article such that the disinfectant article contains a mixture of A and B. In general, an amount of each of solutions A and B is applied to the disinfectant article to achieve about 0.011 ml of each of A and B per square centimeter of the disinfectant article. For example, approximately 3 milliliters of each solution is applied to a disinfectant article that is 6×6.75 inches (15.24×17.15 cm, or approximately 261.4 cm$^2$).

Exemplary embodiments of solutions A and B which may be combined to form an indicator composition as described here are provided in the table below. In each formula, the remainder of the weight percentage of the composition is provided by deionized water, ethanol, and/or comparable solvents.

In embodiments, solution A comprises 0.25-1% w/w methylene blue in water and solution B comprises one or more of ascorbic acid, sodium sulfite, sodium carbonate, sodium perchlorate, and sodium hydroxide, as provided in Table 1. Additional embodiments are shown in Example 10-14.

In embodiments, solution A comprises 0.1-5% w/w malachite green in water and solution B comprises 1-5% w/w of an alkaline builder, such as sodium hydroxide. Additional embodiments are shown in Example 9.

In embodiments, solution A comprises 0.1-5% w/w of a pigment selected from indigo carmine, Acid Green 50, Acid Green 25, FD&C Blue 1, and pinacyanol chloride, an optional catalyst, such as ferrous sulfate and HTAB, and an optional surfactant, such as sodium dodecyl sulfate; and solution B is a 35% aqueous solution of hydrogen peroxide or peracetic acid.

In embodiments, solution A comprises 0.1-5% w/w rhodamine B, alpha naphthol orange, or azo violet in water and solution B comprises bismuth silver oxide or sodium sulfite.

TABLE 1

Exemplary Formulations for Quaternary Ammonium/Alcohol based Disinfectants

| Formula | Solution A (w/w) | | Solution B (w/w) | | Fade Time (min) |
|---|---|---|---|---|---|
| 1 | Methylene Blue | | Ascorbic Acid | | 2.5-5 |
| Preferred | 0.25 | | 0.5 | | |
| Range | 0.25-1 | | 0.5-30 | | |
| 2 | Methylene Blue | | Ascorbic Acid | Sodium Sulfite | 3-6 |
| Preferred | 0.25 | | 0.15 | 27 | |
| Range | 0.25-1 | | 0.5-5 | 10-33 | |
| 3 | Methylene Blue | | Sodium Sulfite | Sodium Carbonate | 4-8 |
| Preferred | 0.25 | | 13.5 | 28 | |
| Range | 0.25-1 | | 10-33 | 20-32 | |
| 4 | Methylene Blue | | Sodium Perchlorate | | 10-30 |
| Preferred | 0.25 | | 55 | | |
| Range | 0.25-1 | | 20-55 | | |
| 5 | Methylene Blue | | Sodium Sulfite | Sodium Hydroxide | 2.5-5 |
| Preferred | 0.25 | | 27 | 0.05 | |
| Range | 0.25-1 | | 10-33 | 0.02-1 | |
| 6 | Methylene Blue | | Sodium Sulfite | | 5-10 |
| Preferred | 0.25 | | 27 | | |
| Range | 0.25-1 | | 10-33 | | |
| 7 | Methylene Blue | | Sodium Hydroxide | | 1-4 |
| Preferred | 0.25 | | 4 | | |
| Range | 0.25-1 | | 1-5 | | |
| 8 | Malachite Green | | Sodium Hydroxide | | 0.5-8 |
| Preferred | 1.5 | | 4 | | |
| Range | 0.1-5 | | 1-5 | | |
| 9 | Indigo Carmine | Ferrous Sulfate | Hydrogen Peroxide (35%) | | 0.5-5 |
| Preferred | 0.5 | 0.5 | 100 | | |
| Range | 0.1-5 | 0.1-5 | | | |
| 10 | Acid Green 50 | | Peracetic Acid (35%) | | 0.1-5 |
| Preferred | 0.5 | | 100 | | |
| Range | 0.1-5 | | | | |
| 11 | FD&C Blue 1 | HTAB | Peracetic Acid (35%) | | 0.5-5 |
| Preferred | 0.5 | 1 | 100 | | |
| Range | 0.1-5 | 0.5-3 | | | |
| 12 | Indigo carmine | HTAB | Peracetic Acid (35%) | | 0.5-2 |
| Preferred | 0.5 | 1 | 100 | | |
| Range | 0.1-5 | 0.5-3 | | | |
| 13 | Acid Green 25 | HTAB | Peracetic Acid (35%) | | 0.1-2 |
| Preferred | 0.5 | 1 | 100 | | |
| Range | 0.1-5 | 0.5-3 | | | |
| 14 | Pinacyanol Chloride | Sodium dodecyl sulfate | Hydrogen peroxide (35%) | | 1-8 |
| Preferred | 0.25 | 1 | 100 | | |
| Range | 0.1-5 | 0.5-3 | | | |
| 15 | Rhodamine B | | Bismuth silver oxide | | 1-8 |
| Preferred | 0.25 | | 0.5 | | |
| Range | 0.1-5 | | 0.1-5 | | |

TABLE 1-continued

| Exemplary Formulations for Quaternary Ammonium/Alcohol based Disinfectants | | | | |
|---|---|---|---|---|
| Formula | Solution A (w/w) | | Solution B (w/w) | Fade Time (min) |
| 16<br>Preferred<br>Range | Alpha naphthol<br>orange<br>0.25<br>0.1-5 | | Sodium<br>sulfite<br>27<br>10-33 | 5-8 |
| 17<br>Preferred<br>Range | Azo violet<br>0.25<br>0.1-5 | | Sodium<br>sulfite<br>27<br>10-33 | 5-8 |
| 18<br>Preferred<br>Range | Methylene Blue<br>0.25<br>0.1-1 | Copper II<br>sulfide caved<br>superstructure<br>40<br>5-80 | Hydrogen<br>Peroxide (35%)<br>100 | 3-8 |
| 19<br>Preferred<br>Range | Indigo Carmine<br>0.5<br>.01-5 | Copper II<br>sulfate<br>0.5<br>0.1-5 | Hydrogen<br>Peroxide (35%)<br>100 | 3-8 |

EXAMPLES

The following non-limiting examples are provided to further illustrate embodiments of the invention disclosed herein. It will be appreciated by those of skill in the art that the techniques disclosed in the examples that follow represent approaches that have been found to function well in the practice of the invention and thus can be considered to constitute examples of modes for its practice. However, those of skill in the art will, in light of the present disclosure, appreciate that many changes can be made in the specific embodiments that are disclosed and still obtain a like or similar result without departing from the spirit and scope of the invention.

Example 1

A liquid composition consisting of:

| | % Wt./Wt. | | | | |
|---|---|---|---|---|---|
| Ingredient | Comp. A | Comp. B | Comp. C | Comp. D | Comp. E |
| Thymolpthalein | 2.86 | 3.74 | 1.21 | 7.33 | 6.86 |
| Ethanol | 95.24 | 93.46 | 97.81 | 88.99 | 91.43 |
| Alkaline builder (NaOH) | 1.90 | 2.80 | 0.98 | 3.68 | 1.71 |

When compositions A, B, C, D and E are applied directly onto a wipe impregnated with 0.55% sodium hypochlorite, 0.65% sodium hypochlorite, 0.3% quat/21% alcohol, 0.5% quat/55% alcohol, or 70% alcohol, upon wiping a surface, a blue trace is left behind that fades away in 10, 12, 6, 15, and 6 minutes, respectively.

Example 2

A liquid composition consisting of:

| | % Wt./Wt. | | | | |
|---|---|---|---|---|---|
| Ingredient | Comp. A | Comp. B | Comp. C | Comp. D | Comp. E |
| FD&C Blue 1 | 0.75 | 1.00 | 1.25 | 1.50 | 1.50 |
| Surfactant (SXS) | 0.50 | 0.35 | 0.50 | 0.25 | 0.00 |
| Surfactant (SDS) | 0.00 | 0.30 | 0.25 | 0.50 | 0.75 |
| Deionized Water | 98.75 | 98.35 | 98.00 | 97.75 | 97.75 |

When compositions A, B, C, D and E are applied directly onto a wipe impregnated with 0.55% or 0.65% sodium hypochlorite, upon wiping a surface, a blue trace is left behind that fades away in 2, 3, 2, 3, and 3 minutes, respectively.

Example 3

A liquid composition consisting of:

| | % Wt./Wt. | | | | |
|---|---|---|---|---|---|
| Ingredient | Comp. A | Comp. B | Comp. C | Comp. D | Comp. E |
| FD&C Blue 1 | 0.75 | 1.00 | 1.25 | 1.50 | 1.50 |
| Alkaline builder (NaOH) | 0.50 | 0.75 | 1.00 | 1.00 | 1.00 |
| Surfactant (SDS) | 0.00 | 0.25 | 0.35 | 0.50 | 0.75 |
| Deionized Water | 98.75 | 98.00 | 97.40 | 97.00 | 96.75 |

When compositions A, B, C, D and E are applied directly onto a wipe impregnated with 0.55% or 0.65% sodium hypochlorite, upon wiping a surface, a blue trace is left behind that fades away in 3, 3, 3, 4, and 4 minutes, respectively.

Example 4

A liquid composition consisting of:

| Ingredient | % Wt./Wt. | | | | |
|---|---|---|---|---|---|
| | Comp. A | Comp. B | Comp. C | Comp. D | Comp. E |
| FD&C Blue 1 | 0.75 | 1.00 | 1.25 | 1.50 | 1.50 |
| Alkaline builder (LiOH) | 0.50 | 0.75 | 1.00 | 1.00 | 1.00 |
| Surfactant (SDS) | 0.00 | 0.25 | 0.35 | 0.50 | 0.75 |
| Deionized Water | 98.75 | 98.00 | 97.40 | 97.00 | 96.75 |

When compositions A, B, C, D and E are applied directly onto a wipe imbued with 0.55% sodium hypochlorite, upon wiping a surface, a blue trace is left behind that fades away in 3, 3, 3, 4, and 4 minutes, respectively.

Example 5

A liquid composition consisting of:

| Ingredient | % Wt./Wt. | | | | |
|---|---|---|---|---|---|
| | Comp. A | Comp. B | Comp. C | Comp. D | Comp. E |
| Acid Green 50 | 0.75 | 1.00 | 1.25 | 1.50 | 1.50 |
| Surfactant (SXS) | 0.50 | 0.35 | 0.50 | 0.25 | 0.00 |
| Surfactant (SDS) | 0.00 | 0.30 | 0.25 | 0.50 | 0.75 |
| Deionized Water | 98.75 | 98.35 | 98.00 | 97.75 | 97.75 |

When compositions A, B, C, D and E are applied directly onto a wipe impregnated with 0.55% or 0.65% sodium hypochlorite, upon wiping a surface, a blue trace is left behind that fades away in 1, 2, 1, 2, and 3 minutes, respectively.

Example 6

A liquid composition consisting of:

| Ingredient | % Wt./Wt. | | | | |
|---|---|---|---|---|---|
| | Comp. A | Comp. B | Comp. C | Comp. D | Comp. E |
| FD&C Blue 1 | 0.50 | 0.75 | 1.25 | 1.50 | 2.50 |
| Surfactant (SXS) | 0.25 | 0.35 | 0.50 | 0.75 | 1.00 |
| Lambda Carrageenan | 0.00 | 0.30 | 0.25 | 0.35 | 0.50 |
| Deionized Water | 99.25 | 98.60 | 98.00 | 97.40 | 96.00 |

When compositions A, B, C, D and E are applied directly onto a wipe impregnated with 0.55% or 0.65% sodium hypochlorite, upon wiping a surface, a blue trace is left behind that fades away in 1, 2, 3, 4, and 5 minutes, respectively.

Example 7

A liquid composition consisting of:

| Ingredient | % Wt./Wt. | | | | |
|---|---|---|---|---|---|
| | Comp. A | Comp. B | Comp. C | Comp. D | Comp. E |
| FD&C Blue 1 | 0.75 | 1.00 | 1.25 | 1.50 | 1.50 |
| Surfactant (SXS) | 0.50 | 0.35 | 0.50 | 0.25 | 0.00 |
| Water | 98.75 | 98.65 | 98.25 | 98.25 | 98.50 |

When compositions A, B, C, D and E are applied directly onto a wipe impregnated with 0.55% or 0.65% sodium hypochlorite, upon wiping a surface, a blue trace is left behind that fades away in 2, 3, 4, 3, and 2 minutes, respectively.

Example 8

A liquid composition consisting of:

| Ingredient | % Wt./Wt. | | | | |
|---|---|---|---|---|---|
| | Comp. A | Comp. B | Comp. C | Comp. D | Comp. E |
| FD&C Blue 1 | 0.75 | 1.00 | 1.25 | 1.50 | 2.00 |
| Water | 99.25 | 99.00 | 98.75 | 98.50 | 98.00 |

When compositions A, B, C, D and E are applied directly onto a wipe impregnated with 0.55% or 0.65% sodium hypochlorite, upon wiping a surface, a blue trace is left behind that fades away in 2, 3, 3, 4, and 5 minutes, respectively.

Example 9

A liquid composition, Solution A, consisting of:

| Ingredient | % Wt./Wt. | | | | |
|---|---|---|---|---|---|
| | Comp. A | Comp. B | Comp. C | Comp. D | Comp. E |
| Malachite Green | 0.50 | 0.75 | 1.25 | 1.50 | 2.50 |
| Deionized Water | 99.50 | 99.25 | 98.75 | 98.50 | 97.50 |

A liquid composition, Solution B, consisting of:

| Ingredient | % Wt./Wt. | | | | |
|---|---|---|---|---|---|
| | Comp. A | Comp. B | Comp. C | Comp. D | Comp. E |
| Alkaline builder (NaOH) | 0.50 | 0.75 | 1.25 | 1.50 | 2.50 |
| Deionized Water | 99.50 | 99.25 | 98.75 | 98.50 | 97.50 |

When compositions A, B, C, D and E from solution A are combined with compositions A, B, C, D, and E from solution B respectively and are applied directly onto a wipe impregnated with 0.3% quat/21% alcohol, 0.5% quat/55% alcohol, or 70% alcohol, upon wiping a surface, a green trace is left behind that fades away in 1, 2, 3, 4, and 5 minutes, respectively.

Example 10

A liquid composition, Solution A, consisting of:

| Ingredient | % Wt./Wt. | | | | |
|---|---|---|---|---|---|
| | Comp. A | Comp. B | Comp. C | Comp. D | Comp. E |
| Methylene Blue | 0.13 | 0.15 | 0.25 | 0.75 | 0.53 |
| Deionized Water | 99.87 | 99.85 | 99.75 | 99.25 | 99.47 |

A liquid composition, Solution B, consisting of:

| Ingredient | % Wt./Wt. | | | | |
|---|---|---|---|---|---|
| | Comp. A | Comp. B | Comp. C | Comp. D | Comp. E |
| Sodium Sulfite | 27.00 | 33.00 | 27.00 | 33.00 | 15.00 |
| Deionized Water | 73.00 | 67.00 | 73.00 | 67.00 | 85.00 |

When compositions A, B, C, D and E from solution A are combined with compositions A, B, C, D, and E from solution B respectively and applied directly onto a wipe impregnated with 0.3% quat/21% alcohol, 0.5% quat/55% alcohol, or 70% alcohol, upon wiping a surface, a blue trace is left behind that fades away in 4, 4, 6, 10, and 20 minutes, respectively.

Example 11

A liquid composition, Solution A, consisting of:

| Methylene Blue | 0.25 | 0.20 | 0.75 | 0.50 | 0.30 |
|---|---|---|---|---|---|
| Deionized Water | 99.75 | 99.80 | 99.25 | 99.50 | 99.70 |

A liquid composition, Solution B, consisting of:

| Sodium Sulfite | 13.50 | 13.50 | 13.50 | 13.50 | 27.00 |
|---|---|---|---|---|---|
| Sodium Carbonate | 13.50 | 23.00 | 28.00 | 28.00 | 5.00 |
| Deionized Water | 73.00 | 63.50 | 58.50 | 58.50 | 68.00 |

When compositions A, B, C, D and E from solution A are combined with compositions A, B, C, D, and E from solution B respectively and applied and applied directly onto a wipe impregnated with 0.3% quat/21% alcohol, 0.5% quat/55% alcohol, or 70% alcohol, upon wiping a surface, a blue trace is left behind that fades away in 5, 5, 5, 7, and 2 minutes, respectively.

Example 12

A liquid composition, Solution A, consisting of:

| Ingredient | % Wt./Wt. | | | | |
|---|---|---|---|---|---|
| | Comp. A | Comp. B | Comp. C | Comp. D | Comp. E |
| Methylene Blue | 0.50 | 0.75 | 1.25 | 1.50 | 2.50 |
| Deionized Water | 99.25 | 98.60 | 98.00 | 97.40 | 96.00 |

A liquid composition, Solution B, consisting of:

| Ingredient | % Wt./Wt. | | | | |
|---|---|---|---|---|---|
| | Comp. A | Comp. B | Comp. C | Comp. D | Comp. E |
| Sodium Sulfite | 0.50 | 0.75 | 1.25 | 1.50 | 2.50 |
| Sodium Carbonate | | | | | |
| Deionized Water | 99.25 | 98.60 | 98.00 | 97.40 | 96.00 |

When compositions A, B, C, D and E from solution A are combined with compositions A, B, C, D, and E from solution B respectively and applied and applied directly onto a wipe impregnated with 0.55% or 0.65% sodium hypochlorite, upon wiping a surface, a blue trace is left behind that fades away in 1, 2, 3, 4, and 5 minutes, respectively.

Example 13

A liquid composition, Solution A, consisting of:

| Ingredient | % Wt./Wt. | | | | |
|---|---|---|---|---|---|
| | Comp. A | Comp. B | Comp. C | Comp. D | Comp. E |
| Methylene Blue | 0.25 | 0.20 | 0.75 | 0.50 | 0.30 |
| Deionized Water | 99.75 | 99.80 | 99.25 | 99.50 | 99.70 |

A liquid composition, Solution B, consisting of:

| Ingredient | % Wt./Wt. | | | | |
|---|---|---|---|---|---|
| | Comp. A | Comp. B | Comp. C | Comp. D | Comp. E |
| Sodium Sulfite | 13.50 | 13.50 | 13.50 | 13.50 | 27.00 |
| Sodium Carbonate | 13.50 | 23.00 | 28.00 | 28.00 | 5.00 |
| Deionized Water | 73.00 | 63.50 | 58.50 | 58.50 | 68.00 |

When compositions A, B, C, D and E from solution A are combined with compositions A, B, C, D, and E from solution B respectively and applied directly onto a wipe impregnated with 0.3% quat/21% alcohol, 0.5% quat/55% alcohol, or 70% alcohol, upon wiping a surface, a blue trace is left behind that fades away in 5, 5, 5, 7, and 2 minutes, respectively.

Example 14

A liquid composition, Solution A, consisting of:

| Ingredient | % Wt./Wt. | | | | |
|---|---|---|---|---|---|
| | Comp. A | Comp. B | Comp. C | Comp. D | Comp. E |
| Methylene Blue | 0.75 | 0.25 | 0.52 | 0.75 | 0.57 |
| Deionized Water | 99.25 | 99.75 | 99.48 | 99.25 | 99.43 |

A liquid composition, Solution B, consisting of:

| Ingredient | % Wt./Wt. | | | | |
| --- | --- | --- | --- | --- | --- |
| | Comp. A | Comp. B | Comp. C | Comp. D | Comp. E |
| Ascorbic Acid | 30.00 | 0.50 | 30.00 | 0.55 | 15.00 |
| Deionized Water | 70.00 | 99.50 | 70.00 | 99.45 | 85.00 |

When compositions A, B, C, D and E from solution A are combined with compositions A, B, C, D, and E from solution B respectively and applied directly onto a wipe impregnated with 0.3% quat/21% alcohol, 0.5% quat/55% alcohol, or 70% alcohol, upon wiping a surface, a blue trace is left behind that fades away in 4, 3, 1, 3, and 5 minutes, respectively.

Example 15

A series of tests was conducted to evaluate the performance of different materials for the roller element of certain implementations of the device described here. The results are shown in the table below.

Performance of various materials as the roller element

| Material Name | Wicking | Durability (in bleach) | Transfer |
| --- | --- | --- | --- |
| Essentra ™ PTX-6981C | very good | very good | good |
| Melamine | very good | very good | good |
| Polyester Knit (Essentra Cloth) | very good | very good | good |
| Treated polyurethane (Capucell) | very good | very poor | good |
| Polyurethane | good | poor | good |
| Clark A ™ | good | poor | good |
| Clark C ™ | good | poor | good |
| Polyimide foam | good | very poor | good |
| Clark B ™ | poor | poor | N/A |
| Polyurethane | poor | very poor | N/A |
| Polyethylene foam | poor | N/A | N/A |
| EPDM foam | very poor | N/A | N/A |
| Vinyl Foam | very poor | N/A | N/A |
| Viton Foam | very poor | N/A | N/A |
| Soft Neoprene/EPDM/SBR Foam 5-9 PSI Firmness | very poor | N/A | N/A |
| Silicone Foam | very poor | N/A | N/A |
| Ionomer Foam | very poor | N/A | N/A |
| Natural Gum Foam | very poor | N/A | N/A |
| ECH Foam | very poor | N/A | N/A |
| Extra Soft Neoprene/EPDM/SBR Foam 2-5 PSI Firmness | very poor | N/A | N/A |
| Cellulose Sponge | very good | good | very poor |
| Polyester, wrapped fibers | very good | good | good |
| Polyolefin, die-cut | very good | very good | good |

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

What is claimed is:

1. A device for applying an indicator composition and, optionally, a disinfectant composition, to at least one of a plurality of articles dispensed through the device, the device comprising:
   a housing at least partially surrounding an interior volume and having (i) an exterior wall defining a dispensing aperture extending through the exterior wall, the exterior wall forming an upper surface of the device or a side surface of the device, and (ii) a lower end region sized to couple to a canister holding the article, the lower end region of the housing comprising an opening through which the at least one of the plurality of articles is drawn from the canister into a dispensing mechanism positioned within the interior volume of the housing, and one or more connecting features configured to removably couple the lower end region to the canister;
   the dispensing mechanism positioned within the interior volume of the housing comprising a plurality of rollers configured to capture and direct the at least one of the plurality of articles through the interior volume of the housing towards the dispensing aperture;
   an optionally removable cartridge containing a penetrable barrier extending through a portion of a cartridge housing, the cartridge housing defining an interior volume of a reservoir, the removable cartridge being coupled, optionally removably coupled, to the device housing, the interior volume of the reservoir comprising at least one chamber sized to contain the indicator composition and, optionally, a second chamber sized to contain the optional disinfectant composition or a component of the indicator composition; and
   an application mechanism positioned within the interior volume of the housing relative to the dispensing aperture, the application mechanism comprising at least one applicator and a transfer element which includes a pump element, wherein at least a portion of the application mechanism is placed in fluid communication with the reservoir of the optionally removable cartridge; and
   an optional actuator configured to simultaneously activate the pump element of the application mechanism and the dispensing mechanism to apply an amount of the indicator composition, and optionally an amount of the optional disinfectant composition or the component of the indicator composition, from the reservoir to the at least one of the plurality of articles as it dispenses through the dispensing aperture.

2. The device of claim 1, wherein when the device is removably coupled to the canister, an interior of the canister is in fluid communication with the interior volume of the housing through the opening.

3. The device of claim 2, wherein the device forms a removable lid for the canister.

4. The device of claim 1, wherein the transfer element transfers the amount of the indicator composition from the reservoir towards the at least one applicator.

5. The device of claim 4, wherein the transfer element creates a pressure differential relative to an interior of the reservoir to transfer the amount.

6. The device of claim 1, comprising the actuator.

7. The device of claim 6, further comprising an automatic dispensing mechanism comprising a motor and a plurality of gear rollers.

8. The device of claim 7, wherein the plurality of gear rollers are configured to capture and direct the article through the interior volume of the housing towards the dispensing aperture.

9. The device of claim 8, wherein the actuator activates the motor.

10. The device of claim 1, further comprising a removable cover positioned over the dispensing aperture.

11. The device of claim 10, wherein the actuator opens the cover exposing the dispensing aperture.

12. The device of claim 11, further comprising one or more grippers configured to engage the article during dispensing allowing for easy removal of the article from the device.

13. The device of claim 12, wherein the actuator activates the one or more grippers.

14. The device of claim 12, wherein the actuator activates one or more of the transfer element, the at least one applicator, the motor, the cover, and the grippers simultaneously.

15. The device of claim 1, wherein the pumping element is manually actuated upon actuation of the actuator to create a pressure differential relative to an interior of the reservoir.

16. The device of claim 1, wherein the transfer element includes a pumping element that is powered by an electric motor upon actuation of the actuator to create a pressure differential relative to an interior of the reservoir.

17. The device of claim 16, wherein the electric motor is powered by a battery coupled to the reservoir.

18. The device of claim 1, wherein the pumping element is a positive displacement pump, reciprocating pump, rotary pump, piston pump, diaphragm pump, peristaltic pump, dynamic pump, centrifugal pump, or hydraulic pump.

19. The device of claim 1, wherein the at least one applicator is configured to apply the amount of indicator composition to the article by directly contacting the article.

20. The device of claim 19, wherein the at least one applicator comprises a roller, brush, or ball-bearing device.

21. The device of claim 19, wherein the at least one applicator comprises a roller surrounding an inner shaft through which a conduit extends leading to one or more outlets.

22. The device of claim 21, wherein the roller comprises a material having wicking and transfer properties.

23. The device of claim 21, wherein the roller comprises one or more of melamine-, polyester-, polyurethane-, polyimide-, polyethylene-, vinyl-, and polyolefin-based materials.

24. The device of claim 21, wherein the roller comprises ethylene propylene diene monomer (EPDM) foam rubber.

25. The device of claim 24, wherein the roller has a hydrophilic coating.

26. The device of claim 21, wherein the roller has an inner core of absorbent material surrounded by a material having a higher coefficient of friction than a coefficient of friction of the article.

27. The device of claim 1, wherein the at least one applicator is configured to apply the amount of indicator composition to the article without directly contacting the article.

28. The device of claim 27, wherein the at least one applicator comprises a sprayer.

29. The device of claim 28, wherein the sprayer comprises an outlet and a spray diverter positioned across from the outlet.

30. The device of claim 29, wherein the spray diverter comprises a surface shaped to re-direct the amount of indicator composition exiting the outlet onto a surface of the article being dispensed through the dispensing aperture.

31. The device of claim 30, wherein the surface of the spray diverter re-directs the indicator composition at an angle that is between 45 degrees to 90 degrees relative to an axis of a spray discharge from the outlet.

32. The device of claim 30, wherein the re-directed indicator composition drips down along a curve of the surface onto an upper surface of the article.

33. The device of claim 1, wherein the application mechanism provides for one-sided or two-sided application of the amount of the indicator composition to the article.

34. The device of claim 1, wherein the reservoir is refillable.

35. The device of claim 1, wherein the reservoir is contained within a cartridge that is removably coupled to the housing.

36. The device of claim 1, further comprising a switch to toggle the device into active and inactive configurations.

37. The device of claim 1, wherein the interior volume of the reservoir comprises a single chamber.

38. The device of claim 1, wherein the interior volume of the reservoir comprises two chambers.

* * * * *